(12) United States Patent
Chen et al.

(10) Patent No.: US 9,181,162 B2
(45) Date of Patent: Nov. 10, 2015

(54) COMPOSITIONS AND METHODS FOR GLUCOSE TRANSPORT INHIBITION

(75) Inventors: Xiaozhuo Chen, Athens, OH (US); Stephen Bergmeier, Athens, OH (US)

(73) Assignee: Ohio University, Athens, OH (US)

( * ) Notice: Subject to any disclaimer, the term of this patent is extended or adjusted under 35 U.S.C. 154(b) by 27 days.

(21) Appl. No.: 13/071,386

(22) Filed: Mar. 24, 2011

(65) Prior Publication Data

US 2012/0121536 A1 May 17, 2012

Related U.S. Application Data

(60) Provisional application No. 61/317,062, filed on Mar. 24, 2010.

(51) Int. Cl.

| | |
|---|---|
| C07C 211/48 | (2006.01) |
| C07C 235/56 | (2006.01) |
| C07C 39/367 | (2006.01) |
| C07C 43/23 | (2006.01) |
| C07C 209/08 | (2006.01) |
| C07D 231/12 | (2006.01) |
| C07D 233/64 | (2006.01) |
| C07D 235/18 | (2006.01) |
| C07D 249/08 | (2006.01) |
| C07D 319/20 | (2006.01) |
| C07D 209/08 | (2006.01) |

(52) U.S. Cl.
CPC ............... *C07C 43/23* (2013.01); *C07C 39/367* (2013.01); *C07C 211/48* (2013.01); *C07C 235/56* (2013.01); *C07D 209/08* (2013.01); *C07D 231/12* (2013.01); *C07D 233/64* (2013.01); *C07D 235/18* (2013.01); *C07D 249/08* (2013.01); *C07D 319/20* (2013.01)

(58) Field of Classification Search
CPC ...... C07C 39/06; C07C 39/367; C07C 43/23; C07C 43/205; C07C 43/2055; C07C 211/48; C07C 211/51; C07C 235/56; A61K 31/05; A61K 31/085; A61K 31/09; A61K 31/137; C07D 209/08; C07D 231/12; C07D 233/64; C07D 235/18; C07D 249/08; C07D 319/20
See application file for complete search history.

(56) References Cited

U.S. PATENT DOCUMENTS

2009/0311249 A1  12/2009  Gianni et al.

FOREIGN PATENT DOCUMENTS

WO        2011119866 A1    9/2011

OTHER PUBLICATIONS

Belaid et. al., Journal of Inorganic Biochemistry, 2008, Elsevier, vol. 102, pp. 63-69.*
Kagwanja et. al., CAS STN Abstracts, Polyhedron, 1994, Pergamon, vol. 13, issue 18, pp. 2615-2627.*
Beger et. al., World Journal of surgery, 2003, Societe Internationale de Chirurgie, vol. 27, pp. 1075-1084.*
Chabner et. al., Nature Reviews Cancer, 2005, Nature Publishing Group, vol. 5, pp. 65-72.*
Leaf, Fortune, Mar. 9, 2004, Time Inc., pp. 1-13.*
International Search Report for PCT/US2011/029843, mailed Jun. 2, 2011, in 2 pages.
Written Opinion of the International Searching Authority for PCT/US2011/029843, mailed Jun. 2, 2011, in 5 pages.
Bauer, et al., "ATP citrate lyase is an important component of cell growth and transformation", Oncogene, (2005), vol. 24, No. 41, pp. 6314-6322.
Bergmeier, et al. "Inhibitors of basal glucose transport as anticancer agents," Abstract No. MEDI 363, American Chemical Society, Division of Medicinal Chemistry, Scientific Abstracts for the 239th National Meeting and Exposition, Mar. 21-25, 2010, San Francisco, CA, published Feb. 22, 2010.
Boehm, et al., "Antiangiogenic therapy of experimental cancer does not induce acquired drug resistance," Nature, (1997), vol. 390, pp. 404-407.
Browder, et al., "Antiangiogenic scheduling of chemotherapy improves efficacy against experimental drug-resistant cancer," Cancer Res., (2000), vol. 60, pp. 1878-1886.
Burt, et al., "Using Positron Emission Tomography with [18F]FDG to Predict Tumor Behavior in Experimental Colorectal Cancer", Neoplasia, (2001), vol. 3, No. 3, pp. 189-195.
Cairns, et al., "Metabolic targeting of hypoxia and HIF1 in solid tumors can enhance cytotoxic chemotherapy", Proc. Natl. Acad. Sci. U.S.A., (2007), vol. 104, No. 22, pp. 9445-9450.
Chan, et al., "Targeting GLUT1 and the Warburg Effect in Renal CellCarcinoma by Chemical Synthetic Lethality," Science Translational Medicine, (Aug. 3, 2011), vol. 3, 94ra70, pp. 1-9.
Elstrom, et al., "Akt stimulates aerobic glycolysis in cancer cells", Cancer Res., (2004), vol. 64, pp. 3892-3899.
Fantin, et al., "Attenuation of LDH-A expression uncovers a link between glycolysis, mitochondrial physiology, and tumor maintenance", Cancer Cell, (Jun. 13, 2006), vol. 9, No. 6, pp. 425-434.
Fantin, et al. "Mitochondriotoxic compounds for cancer therapy", Oncogene, (2006), vol. 25, pp. 4787-4797.

(Continued)

*Primary Examiner* — Sarah Pihonak
(74) *Attorney, Agent, or Firm* — Calfee, Halter & Griswold LLP

(57) ABSTRACT

Glucose deprivation is an attractive strategy in cancer research and treatment. Cancer cells upregulate glucose uptake and metabolism for maintaining accelerated growth and proliferation rates. Specifically blocking these processes is likely to provide new insights to the role of glucose transport and metabolism in tumorigenesis, as well as in apoptosis. As solid tumors outgrow the surrounding vasculature, they encounter microenvironments with a limited supply of nutrients leading to a glucose deprived environment in some regions of the tumor. Cancer cells living in the glucose deprived environment undergo changes to prevent glucose deprivation-induced apoptosis. Knowing how cancer cells evade apoptosis induction is also likely to yield valuable information and knowledge of how to overcome the resistance to apoptosis induction in cancer cells. Disclosed herein are novel anticancer compounds that inhibit basal glucose transport, resulting in tumor suppression and new methods for the study of glucose deprivation in animal cancer research.

11 Claims, 21 Drawing Sheets

(56) References Cited

OTHER PUBLICATIONS

Folkman, et al., "Cancer without disease," Nature, (2004), vol. 427, p. 787.
Gatenby, et al., "Why do cancers have high aerobic glycolysis?", Nat. Rev. Cancer, (2004), vol. 4, pp. 891-899.
Gottlieb, E. "What Does Bioenergetics Have to Do with Cancer?" Am. Assoc. Cancer Res. Edu. Book, (2006), pp. 341-344.
Gottschalk, et al., "Conversion between two cytochalasin B-binding states of the human GLUT1 glucose transporter," Eur. J. Biochem., (2000), vol. 267, pp. 6875-6882.
Herman, et al., "Glucose transport and sensing in the maintenance of glucose homeostasis and metabolic harmony," J. Clin. Invest., (2006), vol. 116, pp. 1767-1775.
"Higashi, et al., ""FDG Uptake, GLUT-1 Glucose Transporter andCellularity in Human Pancreatic Tumors""", J. Nucl. Med., (1998), vol. 39, No. 10, pp. 1727-1735."
Katagiri, et al., "Role of tryptophan-388 GLUT1 glucose transporter in glucose-transport activity and photo-affinity labelling with forskolin," Biochem. J., (1993), vol. 291, pp. 861-867.
Kim, et al., "Cancer's molecular sweet tooth and the Warburg effect", Cancer Res., (2006), vol. 66, pp. 8927-8930.
Klein, et al., "Antidiabetes and anti-obesity activity of *Lagerstroemia speciosa*," Evidence-Based Complementary and Alternative Medicine, (2007), vol. 4, pp. 401-407.
Ko, et al., "Advanced cancers: eradication in all cases using 3-bromopyruvate therapy to deplete ATP", Biochem. Biophys. Res. Commun., (2004), vol. 324, No. 1, pp. 269-275.
Krupka, R. M. "Asymmetrical Binding of Phloretin to the Glucose Transport System of Human Erythrocytes," The Journal of Membrane Biology, (1985), vol. 83, Nos. 1-2, pp. 71-80.
Liu, et al. "Small compound inhibitors of basal glucose transport inhibit cell proliferation and induce apoptosis in cancer cells via glucose-deprivation-like mechanisms", Cancer Lettters, (2010), vol. 298, pp. 176-185.
Ramanathan, et al., "Perturbational profiling of a cell-line model of tumorigenesis by using metabolic measurements", Proc. Natl. Acad. Sci. U.S.A., (2005), vol. 102, No. 17, pp. 5992-5997.
Rastogi, et al., "Glut-1 antibodies induce growth arrest and apoptosis in human cancer cell lines", Cancer Lett., (2007), vol. 257, pp. 244-251.
Ren, et al., "Evidence from transgenic mice that glucose transport is rate-limiting for glycogen deposition and glycolysis in skeletal muscle," J. Biol. Chem., (1993), vol. 268, pp. 16113-16115.
Saito, et al., "Chemical genomics identifies the unfolded protein response as a target for selective cancer cell killing during glucose deprivation", Cancer Res., (2009), vol. 69, pp. 4225-4234.
Semenza, G., "Intratumoral hypoxia, radiation resistance, and HIF-1," Cancer Cell, (2004), vol. 5, pp. 405-406.
Tobak, A. T. "Construction of the 3D Structure of the MTOR Kinase-Domain and Discovery of Novel MTOR Inhibitors", Doctoral Thesis, Rutgers: The State University of New Jersey, (2007), pp. 1-95.
Ulanovskaya, et al., "A Pairwise Chemical Genetic Screen Identifies New Inhibitors of Glucose Transport," Chemistry and Biology, (Feb. 25, 2011), vol. 18, No. 2, pp. 222-230.
Vera, et al., "Genistein Is a Natural Inhibitor of Hexose and Dehydroascorbic Acid Transport through the Glucose Transporter, GLUT1", The Journal of Biological Chemistry, (Apr. 12, 1996), vol. 271, No. 15, pp. 8719-8724.
Wood, et al., "A novel inhibitor of glucose uptake sensitizes cells to FAS-induced cell death", Molecular Cancer Therapeutics, (2008), vol. 7, pp. 3546-3555.
Younes, et al., "Overexpression of the human erythrocyte glucose transporter occurs as a late event in human colorectal carcinogenesis and is associated with an increased incidence of lymph node metastases," Clin. Cancer Res., (1996), vol. 2, pp. 1151-1154.
Yu, et al., "Apoptosis-inducing factor mediates poly(ADP-ribose) (PAR) polymer-induced cell death", Proc. Natl. Acad. Sci. USA, (2006), vol. 103, pp. 18314-18319.
Zhang, et al. "Inhibitors of basal glucose transport as anticancer agents," American Chemical Society 239th National Meeting & Exposition, Mar. 21-25, 2010, San Francisco, CA, Poster Presentation made on Mar. 24, 2010.
Zhang, et al. "Novel inhibitors of basal glucose transport as potential anticancer agents", Bioorganic and Medicinal Chemistry Letters, (2010), vol. 20, pp. 2191-2194.
Zhou, et al. "Akt substrate TBC1 D1 regulates GLUT1 expression through the MTOR pathway in 3T3-L1 adipocytes", Biochemical Journal, (2008), vol. 411, pp. 647-655.
Invitation pursuant to Rule 63(1) EPC for EP Application No. 11760242.5, dated Aug. 14, 2013.
Supplementary European Search Report and Opinion for EP Application No. 11760242.5, dated Dec. 2, 2013.
Effenberger et al., "Nucleophile Substitution von Nitrit in Nitrobenzolen, Nitrobiphenylen and Nitronaphtalien," Chemische Berichte, VCH, vol. 124, pp. 163-173 (Jan. 1, 1990).
Bahr et al., "Dendritic, 1,1'-binaphthalene-derived cleft-type receptors (Dendroclefts) for the molecular recognition of pyranosides," Hevletica Chimica Acta (2000), vol. 83, No. 7, pp. 1346-1376.
Sala et al., "Depsidone Synthesis. Part 16. Benzophenone-Grisa-3'5'-Diene-2'3'-Depsidone Interconversion: A New Theory of Depsidone Biosynthesis," Journal of the Chemical Society, Perkin Transactions 1, Chemical Society, Letchworth, GB; (1981), No. 3, pp. 855-869.
Majumdar et al., "Palladium Mediated bis- and tris-biaryl Heck Coupling for the Synthesis of Heterocycles," Tetrahedron Letters (May 19, 2008), vol. 49, No. 21, pp. 3419-3422.
Smith et al., "Two step synthesis of C2 symmetric 2,6-diarylalkyloxybenzaldehydes—a Mitsunobu approach," Tetrahedron: Asymmetry (1997), vol. 8. No. 20, pp. 3415-3420.
Zhang, Weihe. "Design and Synthesis of Potential Anticancer Agents," Nov. 2010, XP055074386; retrieved from the Internet: URL: https://etd.ohiolink.edu/ap:10:0::NO:10:P10_ACCESSION_NUM:ohiou1288896777.
Notice of Division of Application for Chinese Patent Application No. 201180025712.3, dated Sep. 27, 2013.
English Translation of First Office Action for Chinese Patent Application No. 201180025712.3, dated Jan. 13, 2014.
Second Office Action in Chinese Patent Application No. 201180025712.3 dated Nov. 15, 2014 (9 pages).

* cited by examiner

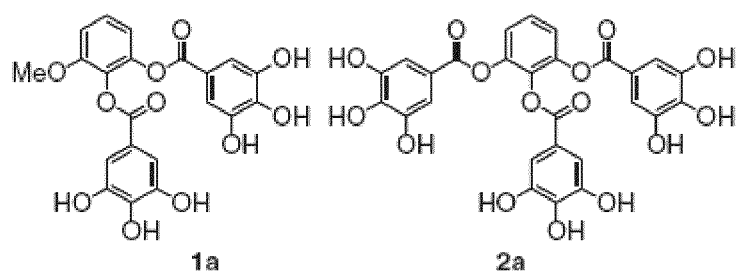
Figure 1
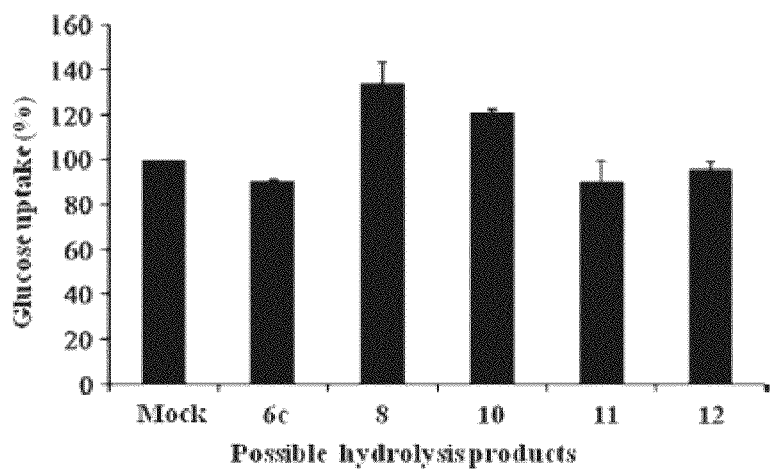
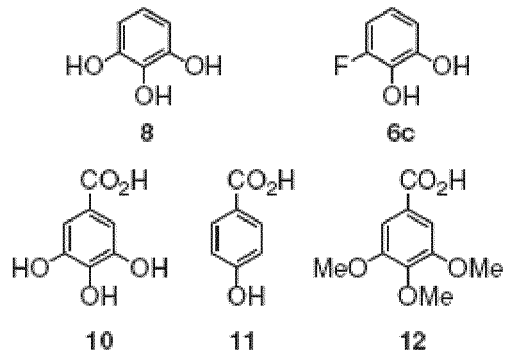
Figure 2

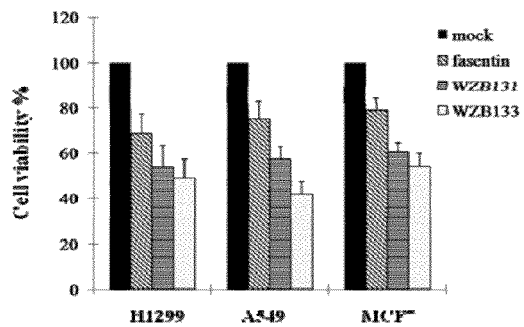

Figure 22B

| Developmental Therapeutics Program | NSC: 750937 / 1 | Conc: 1.00E-5 Molar | Test Date: Aug 17, 2009 |
|---|---|---|---|
| One Dose Mean Graph | Experiment ID: 0908OS22 | | Report Date: Oct 15, 2009 |

| Panel/Cell Line | Growth Percent | Panel/Cell Line | Growth Percent |
|---|---|---|---|
| Leukemia | | Ovarian Cancer | |
| CCRF-CEM | 29.50 | IGROV1 | 27.92 |
| HL-60(TB) | 30.20 | OVCAR-3 | 22.49 |
| K-562 | 73.81 | OVCAR-4 | 60.64 |
| MOLT-4 | 47.49 | OVCAR-5 | 95.10 |
| RPMI-8226 | 61.50 | OVCAR-8 | 54.18 |
| Non-Small Cell Lung Cancer | | NCI/ADR-RES | 43.39 |
| A549/ATCC | 50.57 | SK-OV-3 | 80.03 |
| EKVX | 80.29 | Renal Cancer | |
| HOP-62 | 50.91 | 786-0 | 49.49 |
| HOP-92 | 65.50 | A498 | 114.14 |
| NCI-H226 | 75.56 | ACHN | 36.80 |
| NCI-H23 | 68.81 | CAKI-1 | 54.81 |
| NCI-H322M | 85.64 | RXF 393 | 74.35 |
| NCI-H460 | 36.97 | SN12C | 33.81 |
| NCI-H522 | 29.42 | TK-10 | 95.62 |
| Colon Cancer | | UO-31 | 33.28 |
| COLO 205 | 63.87 | Prostate Cancer | |
| HCC-2998 | 92.50 | PC-3 | 33.54 |
| HCT-116 | 37.67 | DU-145 | 52.18 |
| HCT-15 | 43.36 | Breast Cancer | |
| HT29 | 97.42 | MCF7 | 75.02 |
| KM12 | 50.82 | MDA-MB-231/ATCC | 66.40 |
| SW-620 | 73.54 | HS 578T | 67.15 |
| CNS Cancer | | BT-549 | 48.17 |
| SF-268 | 30.80 | T-47D | 56.77 |
| SF-295 | 89.49 | MDA-MB-468 | 92.95 |
| SF-539 | 36.71 | | |
| SNB-19 | 67.28 | Mean | 60.11 |
| SNB-75 | 58.61 | Delta | 37.62 |
| U251 | 46.96 | Range | 91.65 |
| Melanoma | | | |
| LOX IMVI | 32.36 | | |
| MALME-3M | 90.75 | | |
| M14 | 53.26 | | |
| MDA-MB-435 | 71.71 | | |
| SK-MEL-2 | 90.66 | | |
| SK-MEL-28 | 61.39 | | |
| SK-MEL-5 | 47.40 | | |
| UACC-257 | 81.10 | | |
| UACC-62 | 74.29 | | |

Figure 23

COMPOSITIONS AND METHODS FOR GLUCOSE TRANSPORT INHIBITION

RELATED APPLICATION

This application claims the benefit of U.S. Provisional Application No. 61/317,062, filed Mar. 24, 2010; the entire content of which is incorporated herein by reference.

STATEMENT REGARDING FEDERALLY SPONSORED RESEARCH

This work was sponsored in part by the National Science Foundation through a Partnership for Innovation Grant (HER-0227907). The United States government may have certain rights in the invention.

BACKGROUND

Cancer has overtaken cardiovascular diseases as the number one killer in America since 2008 and it was estimated that 565,650 Americans died of cancer in 2008 alone. Different theories have been proposed for the cause of cancer and numerous strategies have been formulated and explored for combating the disease. The death rates for some cancers such as breast cancer have significantly reduced in the past three decades primarily due to earlier detection rather than treatments, while those of other cancers, such as lung and pancreatic cancer, actually increased. Novel approaches are absolutely and urgently required for further improvement in existing cancer therapies and for treating those cancers for which there are no effective therapies yet. Glucose deprivation may have the potential to become one such novel and effective anticancer strategy due to recent progress made in understanding of the Warburg Effect, the increased and "addicted" reliance of cancer cells on increased glucose transport and glucose metabolism, primarily glycolysis.

One of the common features of almost all cancers and also potentially one of their common weaknesses is the increased glucose uptake and increased dependence on glucose as either a source of building blocks for cell growth and proliferation, a source for energy, or both. Although cancer is not a single disease, different cancers, particularly solid malignant tumors, do share some common characteristics. One such common characteristic is that they all grow faster than normal cells and hence require more synthetic precursors and more energy to maintain their accelerated growth and proliferation rates. Normal cells can utilize different chemicals, such as amino acids, lipids and glucose as their energy sources.

In contrast to typical cells, the preferred sources for biosynthesis materials and energy for cancer cells is glucose. For example, healthy colonocytes derive 60-70% of their energy supply from short-chain fatty acids, particularly butyrate. Butyrate is transported across the luminal membrane of the colonic epithelium via a monocarboxylate transporter, MCT1. Carcinoma samples displaying reduced levels of MCT1 were found to express the high affinity glucose transporter, GLUT1, indicating that there is a switch from butyrate to glucose as an energy/biosynthesis source in colonic epithelia during transition to malignancy.

The strongest piece of evidence that almost all cancer cells in vivo have increased glucose supply and metabolism as compared with normal cells in the body has been provided by positron emission tomography (PET) scans (FIG. 14). In the PET scan of cancer, $^{18}$F-labeled 2-deoxyglucose (2-DG or FDG) as a non-metabolizable glucose analog was used as a tracer. The regions that light up in the scan are organs, tissues, cells, and cancers that trap more FDG. Brighter spots indicate a higher FDG concentration. This specific PET scan, like many others, reveals that both primary and metastatic cancers (near the lung and armpit) contain higher FDG concentrations than surrounding normal cells, providing strong evidence that cancer cells have increased glucose uptake relative to normal cells. The PET scans on various cancer types, including both primary and secondary metastatic cancers, have shown that almost all of the studied tumors "trapped" significantly more FDG as compared to the normal cells and tissues surrounding the tumors. Furthermore, PET scan studies have consistently correlated poor prognosis and increased tumor aggressiveness with increased glucose uptake and upregulated glucose transporters. Although various theories have been proposed to explain the mechanisms by which glucose is used inside cancer cells, there is a near-unanimous consensus in the field that glucose uptake in almost all malignant tumors is increased regardless of how glucose is used by cancer cells after it is taken up. The increased glucose uptake and its accompanied increased glucose metabolism by cancer cells can be, should be, and has been becoming a general target for intensive basic and clinical research and for developing novel anti-cancer therapies.

In the 1920s, Warburg discovered that, even in the presence of abundant oxygen, cancer cells prefer to metabolize glucose by glycolysis in cytosol than the oxidative phosphorylation in mitochondria as in normal cells. This is seemingly paradoxical as glycolysis is less efficient in generating ATP. It has been suggested that such a switch to glycolysis confers cancer cells some selective advantages for survival and proliferation in the unique tumor microenvironment. Because of accelerated growth rates and insufficient oxygen supply, a significant portion of cancer cells in a nodule are in a hypoxic condition, forcing cancer cells to make a shift toward glycolysis by increasing expression of glucose transporters, glycolytic enzymes, and inhibitors of mitochondrial metabolism. However, the Warburg Effect cannot be explained solely by adaptation to hypoxia, since glycolysis is preferred by cancer cells even when ample oxygen is present. Other molecular mechanisms are likely to be involved.

Recent studies have shown that the phenomena observed in Warburg effect, increase glucose consumption and decreased oxidative phosphorylation, and accompanying drastically increased lactate production can also be found in oncogene activation. Ras, when mutated, was found to promote glycolysis. The activation of Akt was found to increase the rate of glycolysis, partially due to its ability to promote the expression of glycolytic enzymes through HIFα. This was speculated as a major factor contributing to the highly glycolytic nature of cancer cells. Myc, the proto-oncogene and a transcription factor, has also been found to upregulate the expression of various metabolic genes. Tumor suppressors, such as p53, have also been found to be involved in regulation of metabolism. All of these recent findings suggest that the Warburg effect in cancer cells is not simply a result of isolated changes in glycolysis alone, but is a biological consequence of extensive communications made through known and unknown cross-talk network among multiple signaling pathways. These pathways are involved in cell growth, proliferation, and both mitochondrial and glucose metabolism that respond to changes in oxygen and nutrient supply. Understanding such extensive signaling networks in the Warburg effect is essential for both understanding and combating cancer.

Some of the most recent studies have focused on glycolytic enzymes, particular on pyruvate kinase (PK). These studies have shown that increased glucose transport and glycolysis in cancer cells appear to be directed toward the generation of building blocks (biosynthesis of macromolecules) in cancer cells, and making preparations for cell division and proliferation rather than as a means to provide bioenergy (ATP). Although aerobic glycolysis is generally accepted as a metabolic hallmark of cancer, its causal relationship with tumorigenesis is still unclear. Glycolysis genes comprise one of the most upregulated gene sets in cancer. Among genes significantly upregulated in tumors is PK, which regulates the rate-limiting final step of glycolysis. Four isoforms of PK exist in mammals: the L and R isoforms are expressed in liver and red blood cells; the M1 isoform is expressed in most adult tissues; and the M2 isoform is a splice variant of M1 expressed during embryonic development. Notably, it has been reported that tumor tissues exclusively express the embryonic M2 isoform of pyruvate kinase. Because of its almost ubiquitous presence in cancer cells, PKM2 has been designated as tumor specific, and its presence in human plasma is currently being used as a molecular marker for the diagnosis of various cancers. Both normal proliferating cells and tumor cells express PKM2. PKM2 regulates the proportions of glucose carbons that are channeled to synthetic processes (inactive dimeric form) or used for glycolytic energy production (highly active tetrameric form, a component of the glycolytic enzyme complex). In cancer cells, the dimeric form of PKM2 is always predominant. The switch between the tetrameric and dimeric form of PKM2 allows tumor cells to survive in environments with varying oxygen and nutrient supplies. The transition between the two forms regulates the glycolytic flux in tumor cells. These findings suggest that PKM2 is a metabolic sensor which regulates cell proliferation, cell growth and apoptotic cell death in a glucose supply-dependent manner. Nuclear translocation of PKM2 was found to be sufficient to induce cell death that is caspase-independent and isoform-specific. These results show that the tumor marker PKM2 plays a general role in caspase-independent cell death of tumor cells and thereby defines this glycolytic enzyme as a novel target for cancer therapy development.

Two recent studies demonstrate that PKM2 is regulated by binding to phospho-tyrosine motifs, leading to promotion of increased cell growth and tumor development. PKM2 enhances the use of glycolytic intermediates for macromolecular biosynthesis and tumor growth. These findings illustrate the distinct advantages of this metabolic phenotype in cancer cell growth. It appears that the expression of PKM2 and switch from oxidative phosphorylation to aerobic glycolysis is absolutely required for maintaining cancer growth and proliferation. Thus, inhibiting glycolysis as well as PKM2 may constitute a new and effective anticancer strategy. These new findings are significant in that they have almost completely changed our conventional understanding of the biological functions of the Warburg effect in cancer, which was believed to be for biosynthesis of ATP under hypoxic conditions.

Glucose is an essential substrate for metabolism in most cells. Because glucose is a polar molecule, transport through biological membranes requires specific transport proteins. Transport of glucose through the apical membrane of intestinal and kidney epithelial cells depends on the presence of secondary active $Na^+$/glucose symporters, SGLT-1 and SGLT-2, which concentrate glucose inside the cells, using the energy provided by co-transport of $Na^+$ ions down their electrochemical gradient. Facilitated diffusion of glucose through the cellular membrane is otherwise catalyzed by glucose carriers (protein symbol GLUT, gene symbol SLC2 for Solute Carrier Family 2) that belong to a superfamily of transport facilitators (major facilitator superfamily) including organic anion and cation transporters, yeast hexose transporter, plant hexose/proton symporters, and bacterial sugar/proton symporters. Molecule movement by such transport proteins occurs by facilitated diffusion. This characteristic makes these transport proteins energy independent, unlike active transporters which often require the presence of ATP to drive their translocation mechanism, and stall if the ATP/ADP ratio drops too low.

Basal glucose transporters (GLUTs) function as glucose channels and are required for maintaining the basic glucose needs of cells. These GLUTs are constitutively expressed and functional in cells and are not regulated by (or sensitive to) insulin. All cells use both glycolysis and oxidative phosphorylation in mitochondria but rely overwhelmingly on oxidative phosphorylation when oxygen is abundant, switching to glycolysis at times of oxygen deprivation (hypoxia), as it occurs in cancer. In glycolysis, glucose is converted to pyruvate and 2 ATP molecules are generated in the process (FIG. 15). Cancer cells, because of their faster proliferation rates, are predominantly in a hypoxic (low oxygen) state. Therefore, cancer cells use glycolysis (lactate formation) as their predominant glucose metabolism pathway. Such a glycolytic switch not only gives cancer higher potentials for metastasis and invasiveness, but also increases cancer's vulnerability to external interference in glycolysis since cancer cells are "addicted" to glucose and glycolysis. The reduction of basal glucose transport is likely to restrict glucose supply to cancer cells, leading to glucose deprivation that forces cancer cells to slow down growth or to starve. Thompson's group found that activated Akt led to stimulated aerobic glucose metabolism in glioblastoma cell lines and that the cells then died when glucose was withdrawn. This provides direct evidence that cancer cells are very sensitive to glucose concentration change and glucose deprivation could induce death in cancer cells.

In normal cells, as shown in FIG. 15, extracellular glucose is taken up by target cells through one or more basal glucose transporters (GLUTs). GLUTs used by cells depend on cell types and physiological needs. For example, GLUT1 is responsible for low level of basal glucose transport in all cell types. All GLUT proteins contain 12 transmembrane domains and transport glucose by facilitating diffusion, an energy-independent process. GLUT1 transports glucose into cells probably by alternating its conformation. According to this model, GLUT1 exposes a single substrate-binding site toward either the outside or the inside of the cell. Binding of glucose to one site triggers a conformational change, releasing glucose to the other side of the membrane. Results of transgenic and knockout animal studies support an important role for these transporters in the control of glucose utilization, glucose storage and glucose sensing. The GLUT proteins differ in their kinetics and are tailored to the needs of the cell types they serve. Although more than one GLUT protein may be expressed by a particular cell type, cancers frequently over express GLUT1, which is a high affinity glucose transporter, and its expression level is correlated with invasiveness and metastasis potentials of cancers, indicating the importance of upregulation of glucose transport in cancer cell growth and in the severity of cancer malignancy. GLUT1 expression was also found to be significantly higher than that of any other glucose transporters. In one study, all 23 tumors tested were GLUT1-positive and GLUT1 was the major glucose transporter expressed. In addition, both FDG uptake and GLUT1 expression appear to be associated with increased tumor size. In several tumors including NSCLC, colon cancer, bladder cancer, breast cancer, and thyroid cancers, increased GLUT1 expression not only confers a malignant phenotype but also predicts for inferior overall survival. Based on all these observations, it is conceivable that inhibiting cancer growth through basal glucose transport inhibition may be an effective way to block cancer growth and improve on prognosis and survival time.

Evidence indicates that cancer cells are more sensitive to glucose deprivation than normal cells. Numerous studies strongly suggest that basal glucose transport inhibition induces apoptosis and blocks cancer cell growth. First, anti-angiogenesis has been shown to be a very effective way to restrict cancer growth and cause cancer ablation. In essence, the anti-angiogenesis approach is to reduce new blood vessel formation and achieve blood vessel normalization inside and surrounding the tumor nodules. This severely limits the nutrients necessary for tumor growth from reaching the cancer cells. One of the key nutrients deprived by anti-angiogenesis is glucose. In this sense, inhibition of basal glucose transport can be viewed as an alternative approach to anti-angiogenesis therapy in restricting nutrient supply to cancer cells. Thus, the success of the anti-angiogenesis strategy indirectly supports the potential efficacy of limiting glucose supply to cancer cells as a related but novel strategy. Second, inhibitors of various enzymes involved in glycolysis, have been used to inhibit different steps in the glycolysis process, and shown to have significant anti-cancer efficacies. The glycolytic enzymes that have been targeted include: hexokinase, an enzyme that catalyzes the first step of glycolysis; ATP citrate lyase; and more recently pyruvate dehydrogenase kinase (PDK). Among glycolysis inhibitors tested, 3-bromopyruvate and a hexokinase inhibitor were found to completely eradicate advanced glycolytic tumors in treated mice. Compounds targeting mitochondrial glycolytic enzyme lactate dehydrogenase A (LDH-A) have shown significant anti-cancer activity both in vitro and in vivo. This result suggests a strong connection between mitochondrial function and cytosolic glycolysis. 2-DG, the tracer used in PET scans for locating metastasis, has been used as a glucose competitor and a glycolytic inhibitor in anti-cancer clinical trials. These and other related studies have also shown that these inhibitors induced apoptosis in cancer cells as a cancer cell killing mechanism. Two important conclusions can be drawn from all these published studies. (1) The compounds that inhibit various steps of glycolysis reduce cancer cell growth both in vitro and in vivo, and (2) inhibiting one of the various steps of glycolysis induces apoptosis in cancer cells and is an effective anti-cancer strategy. They also strongly suggest that inhibiting glucose transport, the step immediately before glycolysis and the first rate-limiting step for glycolysis and all glucose metabolism inside cells, should produce biological consequences to cancer cells similar to or potentially more severe as glycolysis inhibition. In addition, glucose transport may potentially be a better target than downstream glycolysis targets because 1) glucose transporters are known to be highly upregulated in cancer cells, 2) by restricting the glucose supply at the first step and thus, creating an absolute intracellular glucose shortage, it will prevent any potential intracellular glucose-related compensatory/salvage pathways that cancer cells may use for self-rescue and avoidance of cell death.

For inhibiting basal glucose transport to become a successful anti-cancer strategy, it must kill cancer cells without significantly harming the normal cells. Some experimental observations indicate that this is indeed the case. Because cancer cells favor the use of glucose as the energy source and glycolysis is upregulated in cancer cells, compounds that inhibit glycolysis may kill cancer cells while sparing normal cells, which can use fatty acids and amino acids as alternative energy sources.

It has recently been reported that the addition of anti-GLUT1 antibodies to various lung and breast cancer cell lines significantly reduced the glucose uptake rate and proliferation of cancer cells, leading to induction of apoptosis. Furthermore, the antibodies potentiated the anti-cancer effects of cancer drugs such as cisplatin, paclitaxel and gefitinib. These results clearly indicate that agents that inhibit GLUT1-mediated glucose transport are effective either when working alone or when used in combination with other anti-cancer therapeutics to inhibit cancer cell growth and induce apoptosis in cancer cells. These findings are further supported by two recent publications in which glucose transport inhibitor fasentin was found to sensitize cancer cells to undergo apoptosis induced by anticancer drugs cisplatin or paclitaxel and anticancer compound apigenin was found to down-regulate GLUT1 at mRNA and protein levels. Down-regulation of GLUT1 was proposed as the potential anticancer mechanism for apigenin. All these new findings point to the direction that glucose transport inhibitors are likely to sensitize and synergize with other anticancer drugs to further enhance anticancer efficacy of the drugs. Disclosed herein are compounds and methods that are 2-5 times more potent than either fasentin or apigenin in inhibiting basal glucose transport and induction of apoptosis.

In one recent study using glucose deprivation, cells growing in high concentrations of growth factors were found to show an increased susceptibility to cell death upon growth factor withdrawal. This susceptibility correlated with the magnitude of the change in the glycolytic rate following growth factor withdrawal. To investigate whether changes in the availability of glycolytic products influence mitochondrion-initiated apoptosis, glycolysis was artificially limited by manipulating the glucose levels in cell culture media. Like growth factor withdrawal, glucose limitation resulted in Bax translocation, a decrease in mitochondrial membrane potential, and cytochrome c release to the cytosol. In contrast, increasing cell autonomous glucose uptake by over-expression of GLUT1 significantly delayed apoptosis following growth factor withdrawal. These results suggest that a primary function of growth factors is to regulate glucose uptake and metabolism and thus maintain mitochondrial homeostasis and enable anabolic pathways required for cell growth. It was also found that expression of the three genes involved in glucose uptake and glycolytic commitment, GLUT1, hexokinase 2, and phosphofructokinase 1, was rapidly declined to nearly undetectable levels following growth factor withdrawal. All of these studies suggest that glucose deprivation has been a very valuable and frequently used method for studying cancer. Intracellular glucose deprivation can also be created by inhibition of basal glucose transport. The difference between glucose deprivation resulted from glucose removal from cell culture media and from inhibition of glucose transport/glucose metabolism is that glucose removal generates initially a glucose deprived extracellular environment while inhibition of glucose transport/glucose metabolism generates a glucose deprived intracellular environment without changing or even increasing extracellular glucose concentration. The use of glucose transport inhibitors should be able to supplement and substitute traditional glucose deprivation. Furthermore, traditional glucose deprivation by decreasing extracellular glucose concentration cannot be used in animals while inhibitors of glucose transport can, creating a new approach in studying cancer in vivo and in treating cancer.

BRIEF DESCRIPTION

Disclosed herein are compounds of formula (I), in which $R_1$ is selected from a group consisting of hydrogen, alkyl, benzyl, aryl, and heteroaryl moieties; $R_2$ is selected from the group consisting of hydrogen, alkyl, benzyl, aryl, heteroaryl, and fluorescent tags; $R_3$ is selected from the group consisting of hydrogen, halo, alkyl, benzyl, aryl, heteroaryl, amino, cyano, and alkoxy; or a salt thereof. In some embodiments, the two $R_1$ groups may be independently selected, and hence different as recognized by one of skill in the art. In other embodiments, when the $R_1$ groups are different, $R_1$ may be represents as $R_{1''}$ and $R_{1'''}$ to indicate a difference between $R_1$ moieties.

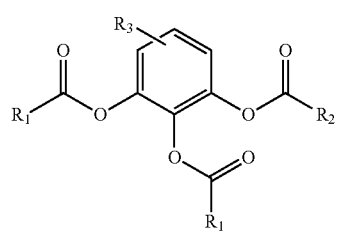

(I)

In some embodiments, the compound of formula (I) may be further defined to include species where $R_1$ is an aryl functionality selected from the group consisting of 2-, 3-, and 4-hydroxyphenyl, 2,3-, 2,4-, 2,5-, 2,6-, 3,4-, and 3,5-dihydroxyphenyl, 2,3,4-, 2,3,5-, 2,3,6-, and 3,4,5-trihydroxyphenyl, 2,3,4,5- and 2,3,4,6-tetrahydroxyphenyl, and perhydroxyphenyl. In other embodiments, the compound of formula (I) may be further defined where $R_2$ is a fluorescent tag selected from the group consisting of coumarins, dansyl, rhodamine, fluorescein, and carboxynaphthofluorescein. In some embodiments, the compound of formula (I) is consisting of a molecule, in which $R_1$ and $R_2$ are equal to 3-hydroxyphenyl and $R_3$ is a hydrogen atom.

Disclosed herein are compounds of formula (II), in which $R_1$ is selected from the group consisting of hydrogen, alkyl, benzyl, aryl, and heteroaryl; $R_2$ is selected from the group consisting of hydrogen, alkyl, benzyl, aryl, and heteroaryl; X is selected from the group consisting of hydrogen, halo, alkyl, benzyl, aryl, heteroaryl, amino, cyano, and alkoxy; Y is selected from the group consisting of hydrogen, halo, alkyl, benzyl, aryl, heteroaryl, amino, cyano, and alkoxy; or a salt thereof.

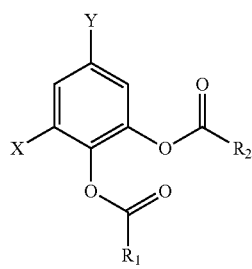

(II)

In some embodiments, the compound of formula (II) may be further defined to include species where $R_1$ is an aryl functionality selected from the group consisting of 2-, 3-, and 4-hydroxyphenyl, 2,3-, 2,4-, 2,5-, 2,6-, 3,4-, and 3,5-dihydroxyphenyl, 2,3,4-, 2,3,5-, 2,3,6-, and 3,4,5-trihydroxyphenyl, 2,3,4,5- and 2,3,4,6-tetrahydroxyphenyl, and perhydroxyphenyl. In other embodiments, the compound of formula (II) is consisting of a molecule in which $R_1$ and $R_2$ are equal to 3-hydroxyphenyl, X is equal to fluorine, and Y is equal to hydrogen.

Disclosed herein is a series of compounds of formula (III), in which $R_1$ is selected from the group consisting of hydrogen, halo, alkyl, benzyl, amino, nitro, cyano, and alkoxy; $R_2$ is selected from the group consisting of hydrogen, halo, alkyl, benzyl, amino, nitro, cyano, and alkoxy; $R_3$ is selected from the group consisting of hydrogen, halo, alkyl, benzyl, amino, nitro, cyano, and alkoxy; X is selected from the group consisting of carbon, oxygen, nitrogen and sulfur; and Y is selected from the group consisting of carbon, oxygen, nitrogen and sulfur; or, a salt thereof

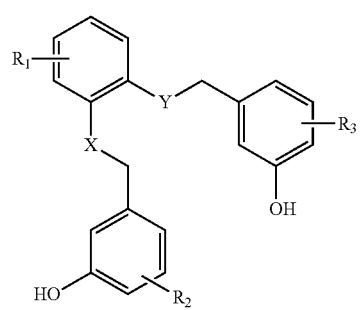

(III)

In some embodiments, the compound of formula (III) may be selected from the group consisting of the following compounds;

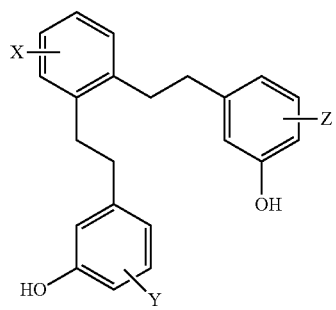

8

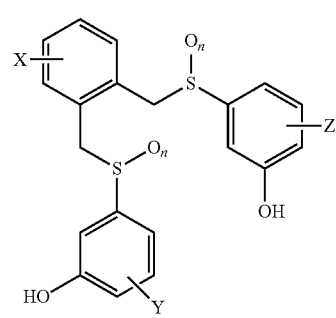

9, n = 0
10, n = 1
11, n = 2

-continued
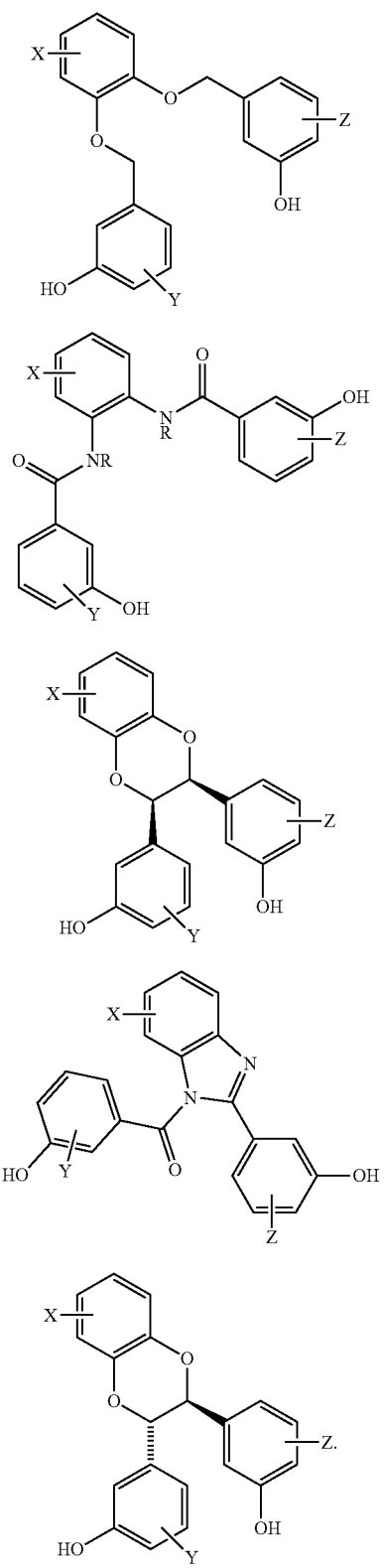
For all compounds X = H, 3-Cl, 3-F, 3-CN, 4-F
4-CN, 4-NO₂, 4-SO₂Me, 4,5-Cl₂
For all compounds Y or Z = H, 2-Cl, 2-F, 2-OMe, 2-CH₂OH
3-CH₂OH
In some embodiments, the compound of formula (III) may be selected from the group consisting of the following compounds;
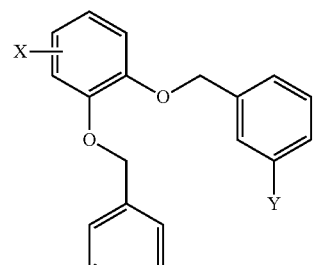
31, Y = NHC(O)CH₃
32, Y = NHS(O)₂CH₃
33, Y = NHCONH₂
34, Y = CH₂OH
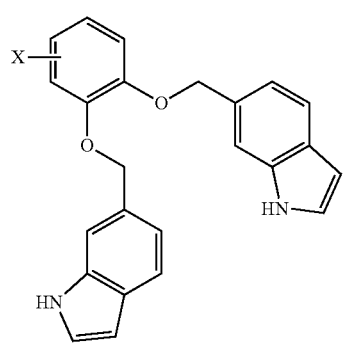
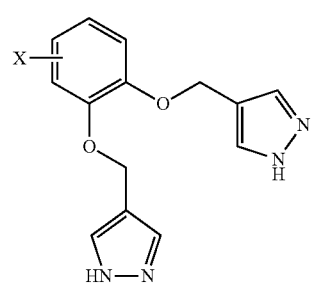
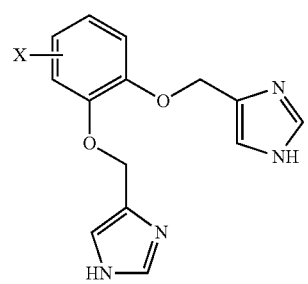

-continued

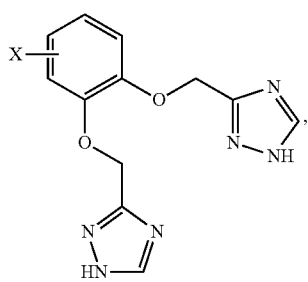
38 and where X is selected from the group consisting of H, 3-Cl, 3-F, 3-CN, 4-F, 4-CN, 4-NO$_2$, 4-SO$_2$Me, and 4,5-Cl$_2$. In other embodiments, the compound of formula (III) is consisting of a molecule in which R$_1$, R$_2$, and R$_3$ are hydrogen, and X and Y are oxygen.

Disclosed herein are compounds of formula (IV), in which R$_1$ is selected from the group consisting of hydrogen, halo, alkyl, benzyl, amino, nitro, cyano, and alkoxy; R$_2$ is selected from the group consisting of hydrogen, alkyl, benzyl, aryl, and heteroaryl; R$_3$ is selected from the group consisting of hydrogen, alkyl, benzyl, aryl, and heteroaryl; or a salt thereof. In some embodiments, the compound of formula (IV) is a molecule, in which R$_1$ is chlorine, and R$_2$ and R$_3$ are 2-nitro-5-hydroxyphenyl groups.

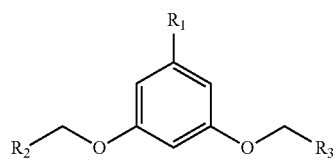
(IV)

Disclosed herein are methods for the treating cancer involving the administration of a therapeutically effective amount of a compound selected from the group consisting of formula 1, 2, 3, and 4 to a subject in need of such treatment.

In some embodiments, the cancer is a solid malignant tumor that upregulates basal glucose transport via a biological shift from oxidative phosphorylation to glycolysis in a process known as the Warburg effect. In some embodiments, administration of the compound to a human subject may be by any method selected from the group consisting of oral, topical, intra-arterial, intrapleural, intrathecal, intraventricular, subcutaneous, intraperitoneal, intraveneous, intravesicular, and gliadel wafers.

In some embodiments, the compound from formulas 1, 2, 3, and 4 may be administered to a human subject or patient in combination with one or multiple chemotherapeutic agents as a means to enhance the efficacy of one or more of the therapeutically useful compounds. In other embodiments, the chemotherapeutic agent that the compound from formulas 1, 2, 3, and 4 may be administered in combination with is selected from the group consisting of methotrexate, doxorubicin hydrochloride, fluorouracil, everolimus, imiquimod, aldesleukin, alemtuzumab, pemetrexed disodium, palonosetron hydrochloride, chlorambucil, aminolevulinic acid, anastrozole, aprepitant, exemestane, nelarabine, arsenic trioxide, ofatumumab, bevacizumab, azacitidine, bendamustine hydrochloride, bexarotene, bleomycin, bortezomib, cabazitaxel, irinotecan hydrochloride, capecitabine, carboplatin, daunorubicin hydrochloride, cetuximab, cisplatin, cyclophosphamide, clofarabine, Ifosfamide, cytarabine, dacarbazine, decitabine, dasatinib, degarelix, denileukin difitox, denosumab, dexrazoxane hydrochloride, docetaxel, rasburicase, epirubicin hydrochloride, oxaliplatin, eltrombopaq olamine, eribulin mesylate, erlotinib hydrochloride, etoposide phosphate, raloxifene hydrochloride, toremifane, fulvestrant, letrozole, filgrastim, fludarabim phosphate, pralatrexate, gefitinib, gemcitabine hydrochloride, gemcitibine-cisplatin, gemtuzumab ozogamicin, imatinib mesylate, trastuzamab, topotecan hydrochloride, ibritumomab tiuxetan, romadepsin, ixabepilone, palifermin, lapatinib ditosylate, lenalidomide, leucovorin calcium, leuprolide acetate, liposomal procarbazine hydrochloride, temozolomide, plerixafor, acetidine, sorafenib tosylate, nilotinib, tamoxifen citrate, romiplostim, paclitaxel, pazopanib hydrochloride, pegaspargase, prednisone, procarbazine hydrochloride, proleukin, rituximab, romidepsin, Talc, sorafenic tosylate, sunitinib malate, thalidomide, temsirolimus, toremifene, trastuzumub, pantiumumab, vinblastine sulfate, vincristine, vorinostat, and zoledronic acid.

Additional features and advantages will be set forth in part in the description that follows, and in part will be obvious from the description, or may be learned by practice of the inventions. The objects and advantages of the inventions will be realized and attained by means of the elements and combinations particularly pointed out in the appended claims.

It is to be understood that both the foregoing general description and the following detailed description are exemplary and explanatory only and not restrictive of the invention, as claimed.

BRIEF DESCRIPTION OF THE SEVERAL VIEWS OF THE DRAWINGS

The accompanying drawings, which are incorporated in and constitute a part of this specification, illustrate some embodiments of the inventions, and together with the description, serve to explain principles of the inventions.

FIG. 1 shows the initial glucose transport inhibitors 1a and 2a.

FIG. 2 shows glucose uptake results for the possible hydrolyzed products from 1p, 9a, and 2a. These possible hydrolyzed products do not show significant inhibition of basal glucose uptake, suggesting that the inhibition was due to the original compounds, not the hydrolyzed products.

FIG. 23 shows an NCI anticancer activity screening results for compound WZB-115 in 59 cancer cell lines. WZB-115 was sent to NCI for anticancer activity screening using 59 cancer cell lines, including 9 cancer types. The test was done at a single concentration: 10 µM. Growth rates of mock treated cancer cells were used as baseline 100%. Any growth rate that is smaller than 100% indicates an inhibition. Because of its promising anticancer activity profile, NCI has recommended that the compound be tested again using five different concentrations to determine its $IC_{50}$s in these cancer cell lines.

DETAILED DESCRIPTION

Figure 3:
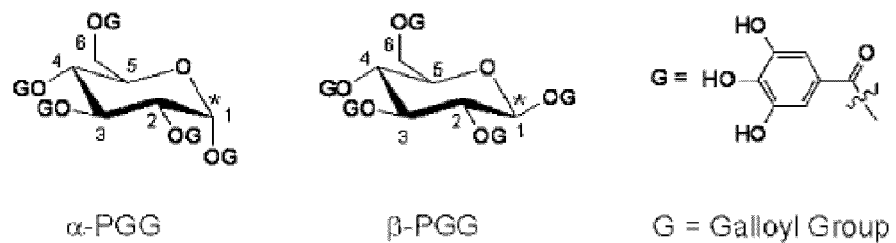
FIG. 3 shows the molecular structures of α-PGG and β-PGG. PGG has a glucose core that is linked to five galloyl groups through ester bonds that are formed between the hydroxyl groups of glucose and gallic acids. α-PGG and β-PGG are structural isomers. α-PGG and its derivatives are hydrophilic and are likely to work extracellularly on cell membrane proteins.
Figure 4:
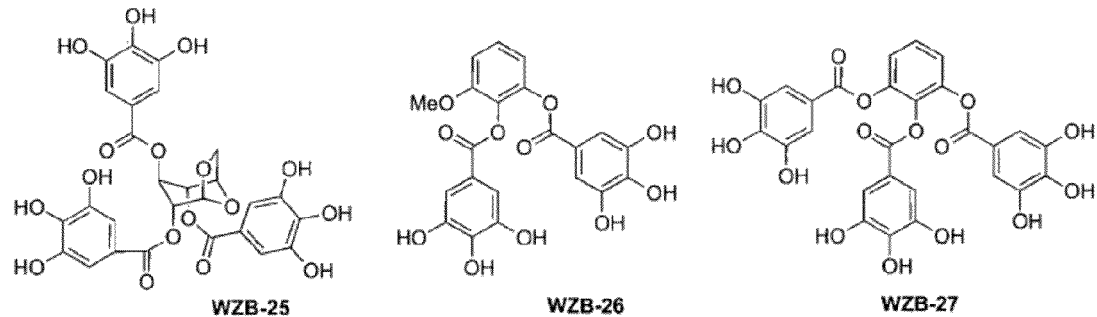
FIG. 4 shows the structure of novel inhibitors of basal glucose transport WZB-25, WZB-26, and WZB-27.

The present inventions will now be described by reference to some more detailed embodiments, with occasional reference to the accompanying drawings. These inventions may, however, be embodied in different forms and should not be construed as limited to the embodiments set forth herein. Rather, these embodiments are provided so that this disclosure will be thorough and complete, and will fully convey the scope of the inventions to those skilled in the art.

Unless otherwise defined, all technical and scientific terms used herein have the same meaning as commonly understood by one of ordinary skill in the art to which these inventions belong. The terminology used in the description of the inventions herein is for describing particular embodiments only and is not intended to be limiting of the inventions. As used in the description of the inventions and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present inventions. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the inventions are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

In addition, where features or aspects of the invention are described in terms of Markush groups or other grouping of alternatives, those skilled in the art will recognize that the invention is also thereby described in terms of any individual member or subgroup of members of the Markush group or other group.

DEFINITIONS

"Alkyl" shall refer to any chemical compound that consists only of the elements hydrogen and carbon, wherein the atoms are linked together exclusively through single bonds. The term alkyl may also be extended to mean any chemical compound that consists only of the elements hydrogen, fluorine, and carbon, wherein the atoms are linked together exclusively through single bonds. This class of fluorinated compounds may also be referred to as "fluoroalkanes," "fluoroalkyl," "fluoroalkyl groups," and "fluorocarbons." Examples of hydrocarbons include, but are not limited to methyl, ethyl, n-propyl, i-propyl, cyclopropyl, n-butyl, sec-butyl, i-butyl, t-butyl, cyclobutyl, n-pentyl, i-pentyl, neo-pentyl, cyclopentyl, n-hexyl, cyclohexyl, thexyl, n-heptyl, n-octyl, n-decyl, and adamantyl. Examples of fluorinated compounds include, but are not limited to fluoromethyl, difluoromethyl, trifluoromethyl, 1,1,1-trifluoroethyl, 2,2-difluoroethyl, and perfluoroethyl.

"Benzyl" shall be used to describe the substituent or molecular fragment possessing a structure related to $RC_6H_4CH_2$— of an organic compound. A substituted benzyl compound may also be described as any aryl or heteroaryl ring system attached to a methylene (—$CH_2$—) subunit. Examples of benzyl groups include, but are not limited to benzyl; 2, 3, and 4-halobenzyl; 2, 3, and 4-alkylbenzyl; 2, 3, and 4-cyanobenzyl; 2, 3, and 4-ketobenzyl; 2, 3, and 4-carboxybenzyl; 2, 3, and 4-aminobenzyl; 2, 3, and 4-nitrobenzyl; 2, 3, and 4-hydroxybenzyl; 2, 3, and 4-alkoxybenzyl; disubstituted benzyl, and trisubstituted benzyl derivatives.

"Aryl" shall mean any functional group on a compound that is derived from a simple aromatic ring. Examples include, but are not limited to phenyl; 2-, 3-, and 4-hydroxyphenyl; 2,3-, 2,4-, 2,5-, 2,6-, 3,4-, and 3,5-dihydroxyphenyl; 2,3,4-, 2,3,5-, 2,3,6-, and 3,4,5-trihydroxyphenyl; 2,3,4,5- and 2,3,4,6-tetrahydroxyphenyl; perhydroxyphenyl; 2, 3, and 4-halophenyl; 2, 3, and 4-alkylphenyl; 2, 3, and 4-cyanophenyl; 2, 3, and 4-ketophenyl; 2, 3, and 4-carboxyphenyl; 2, 3, and 4-aminophenyl; 2, 3, and 4-nitrophenyl; 2, 3, and 4-hydroxyphenyl; 2, 3, and 4-alkoxyphenyl; disubstituted phenyl, and trisubstituted phenyl derivatives.

"Heteroaryl" shall mean any functional group on a compound that is derived from a heteroaromatic ring. Heteroaromatic species contain a heteroatom, or an atom other than hydrogen or carbon, including, oxygen, nitrogen, sulfur, phosphorous, silicon, and boron. Examples include, but are not limited to furans, benzofurans, thiophenes, benzothiophenes, pyrroles, indoles, and borabenzenes.

"Halo" and "halogen" shall refer to any element of the periodic table from Group 17, consisting of fluorine, chlorine, bromine, iodine, and astatine.

"Amine" and "amino" shall refer to any organic compound or functional group that contains a basic nitrogen with a lone pair of electrons. Amines are derived from ammonia and may be primary, secondary, and tertiary. Examples of amines include, but are not limited to ammonia, methylamine, dimethylamine, trimethylamine, ethylamine, diethylamine, triethylamine, ethyldimethylamine, isopropylamine, diisopropylamine, diisopropylethylamine, diphenylamine, dibenzylamine, t-butylamine, analine, and pyridine.

"Cyano" shall be considered synonymous with the organic functionality nitrile, which contains a carbon triple-bonded to a nitrogen atom. Cyanides tend to be highly toxic in nature, and are typically found as salts.

"Alkoxy" shall mean an alkyl group singly bonded to an oxygen. The range of alkoxy groups is great, ranging from methoxy to any number of arylalkoxy groups. Examples of alkoxy groups include, but are not limited to methoxy, ethoxy, n-propoxy, i-propoxy, n-butoxy, t-butoxy, and phenoxy.

"Fluorescent tags," "fluorescent molecule," "fluorophore," and "fluorescent labels" shall mean any portion of a molecule that scientists or researchers have attached chemically to aid in the detection of the molecule to which it has been attached. Examples of fluorescent tags include, but are not limited to coumarins, dansyl, rhodamine, fluorescein, carboxynaphthofluorescein, and fluorescent proteins.

A "salt" shall refer to an ionic species resulting from the pairing of an anionic derivative of one of the compounds from formulas 1, 2, 3, and 4 with a cationic species. The cationic species may include, but is not limited to lithium, sodium, potassium, rubidium, cesium, beryllium, magnesium, calcium, strontium, barium, aluminum, copper, zinc, iron, chromium, manganese, nickel, palladium, platinum, indium, rhodium, and arsenic.

"Therapeutically effective" when used to describe an amount of a compound applied in a method, refers to the amount of a compound that achieves the desired biological effect, for example, an amount that leads to the inhibition of basal glucose transport.

"Inhibit" or "stop" shall mean reduce, inhibit, damage, eliminate, kill, or a combination thereof.

"Lowering" in the context of basal glucose transport shall mean to reduce the efficiency of glucose transport within a cancer cell.

Structure of α-PGG-Derived Generation 1 Compounds; WZB-25, WZB-26, and WZB-27

The methods for the synthesis of compounds WZB-25, WZB-26, and WZB-27 are as follows:

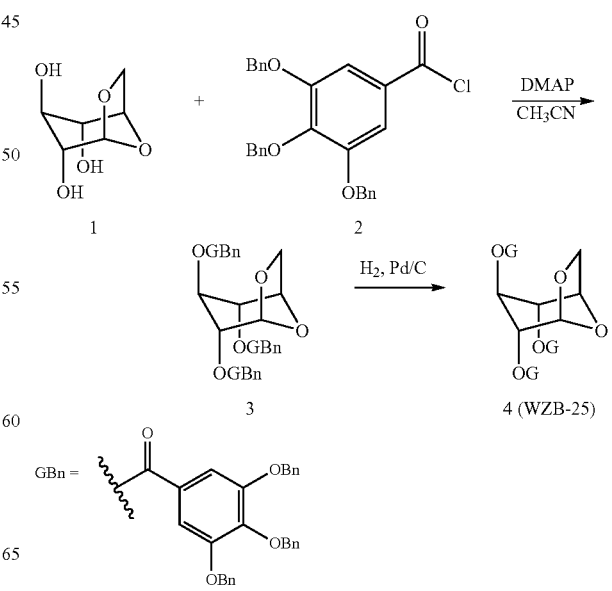

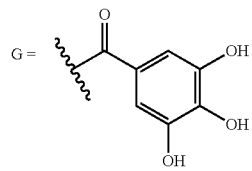

Acid chloride 2 (863 mg, 1.88 mmol) was added to a solution of 1,6-anhydro-β-D-glucose (100 mg, 0.62 mmol) in anhydrous acetonitrile (25 mL) at room temperature. DMAP (241 mg, 1.97 mmol) was added to the reaction mixture after stirred for 30 min at room temperature, the mixture was stirred for 24 h and the solvent was removed, the crude was purified by chromatography on silica gel giving 730 mg of 3 in 83% yield. $^1$H NMR (CDCl$_3$) δ 7.60-7.31 (m, 51H), 5.88 (s, 1H), 5.69 (t, 1H, J=3.0 Hz), 5.29 (d, 3H, J=5.3 Hz), 5.23 (s, 4H), 5.11-5.02 (m, 13H), 4.98 (d, 1H, J=6.2 Hz), 4.28 (d, 1H, J=7.4 Hz), 3.97 (q, 1H, J=6.2, 7.4 HZ).

10% palladium on carbon (21 mg, 0.02 mmol) was added to a solution of 3 (420 mg, 0.29 mmol) in anhydrous THF (20.0 mL), the mixture was stirred under hydrogen gas atmosphere for overnight at room temperature. The mixture was filtered through Celite, the filtrate was diluted with methanol and dichloromethane and filtered through Celite three times until the solution was clear. The solvent was removed and gave crude 4 in 64% yield.

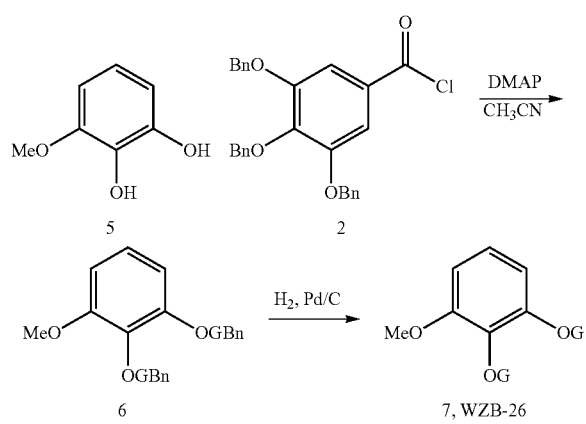

Acid chloride 2 (941 mg, 2.05 mmol) was added to a solution of 3-methoxycatechol (140 mg, 1.00 mmol) in anhydrous acetonitrile (10 mL) at room temperature. DMAP (268 mg, 2.20 mmol) was added to the reaction mixture after stirred for 30 min at room temperature, the mixture was stirred for 2 days and the solvent was removed, the crude was purified by chromatography on silica gel (25% EA in hexane) giving 708 mg of 6 in 72% yield. $^1$H NMR (CDCl$_3$) δ 7.64 (d, 4H, J=16.7 Hz), 7.51-7.33 (m, 31H), 7.16 (d, 1H, J=8.2 Hz), 7.06 (d, 1H, J=8.4 Hz), 5.18 (d, 4H, J=7.0 Hz), 5.06 (d, 8H, J=11 Hz), 3.96 (s, 3H); $^{13}$C NMR (CDCl$_3$) δ 164.0, 163.6, 153.1, 152.8, 152.3, 144.1, 143.2, 137.6, 137.5, 136.5, 136.4, 132.3, 128.6, 128.4, 128.3, 128.2, 128.1, 128.0, 127.8, 127.7, 126.6, 123.9, 123.8, 115.4, 110.2, 109.7, 109.6, 75.3, 71.2, 56.4.

10% palladium on carbon (43 mg, 0.04 mmol) was added to a solution of 6 (500 mg, 0.51 mmol) in anhydrous THF (20.0 mL), the mixture was stirred under hydrogen gas atmosphere for 12 h at room temperature. Then the mixture was filtered through Celite, the filtrate was concentrated and purified by chromatography on silica gel giving 9.5 mg of 7. Most of compound 7 was decomposed on silica gel. $^1$H NMR (CDCl$_3$) δ 8.30 (brs, 6H), 7.31-7.13 (m, 5H), 7.04 (d, 1H, J=8.1 Hz), 6.95 (d, 1H, J=8.3 Hz), 3.83 (s, 3H).

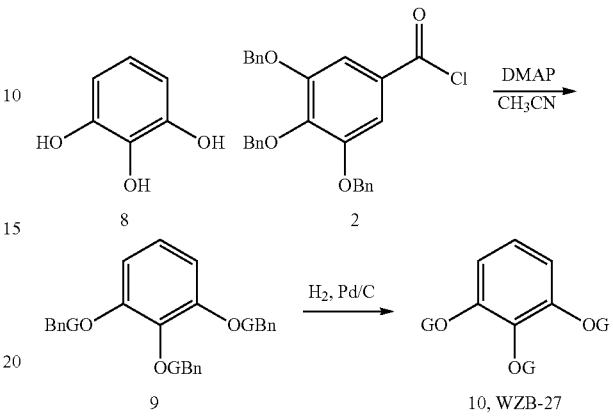

Acid chloride 2 (1.40 g, 3.05 mmol) was added to a solution of pyrogallol (126 mg, 1.00 mmol) in anhydrous acetonitrile (15 mL) at room temperature. DMAP (391 mg, 3.20 mmol) was added to the reaction mixture after stirred for 30 min at room temperature, the mixture was stirred for 24 h and the solvent was removed, the crude was purified by chromatography on silica gel (25% EA in hexane as eluent) giving 570 mg of 9 in 41% yield. $^1$H NMR (CDCl$_3$) 7.53 (s, 4H), 7.49-7.20 (m, 50H), 5.10 (s, 4H), 5.01 (s, 8H), 4.94 (s, 2H), 4.85 (s, 4H); $^{13}$C NMR (CDCl$_3$) δ 163.6, 163.0, 152.7, 144.2, 143.6, 143.3, 137.4, 137.3, 136.3, 136.1, 135.2, 128.6, 128.5, 128.4, 128.2, 128.1, 128.0, 127.9, 127.8, 126.3, 123.6, 123.1, 120.9, 109.6, 75.2, 75.1, 71.2.

10% palladium on carbon (16 mg, 0.024 mmol) was added to a solution of 6 (260 mg, 0.29 mmol) in anhydrous THF (15.0 mL), the mixture was stirred under hydrogen gas atmosphere for overnight at room temperature. Then the mixture was filtered through Celite, the filtrate was concentrated and purified by chromatography on silica gel (25% EA in hexane) giving 11.3 mg of 10. Compound 10 was decomposed on the column. $^1$H NMR (CDCl$_3$) δ 8.24 (brs, 4H), 7.47-7.41 (m, 1H), 7.34-7.32 (m, 2H), 7.17 (s, 4H), 7.09 (s, 2H), 2.92 (brs, 5H).

Evaluation of Generation 1 Compounds Derived from α-PPG

Compounds 1a and 2a were initially prepared as potential anti-diabetic analogs of α-PGG (FIG. 1). Given the tight SAR of this class of compounds, it was hypothesized that a more rigid scaffold (i.e., a benzene ring) might enhance the activity. Rather than possessing insulin-like activity, these two compounds were surprisingly and serendipitously found to inhibit basal glucose transport on cervical (HeLa), colon (RKO), and breast (MCF-7) cancer cells at a concentration of 30 μM (Table 1).

TABLE 1

Glucose transport inhibitory activity (%) of 1a and 2a in different cancer cell lines

| Compound | Hela | RKO | MCF-7 |
|---|---|---|---|
| 1a | 46.3 ± 3.3 | 57.2 ± 4.4 | 33.0 ± 0.5 |
| 2a | 36.0 ± 4.9 | 58.1 ± 0.1 | 60.4 ± 2.4 |

Compounds 1a and 2a also inhibited basal glucose transport in H1299 cells by 58.4±6.3% and 86.1±1.0%, respectively (Table 2); as measured by a standard glucose uptake assay compared to non-compound treated cells controls (considered as 0% inhibition). Tested in an MTT cell proliferation assay in H1299 cells, their inhibitory activities on cancer cell growth were found to be 36.0±6.1% and 39.9±5.0%, respectively (non-compound treated cell controls were considered as 0% inhibition).

Given the potential utility of the inhibition of glucose transport for development of novel anticancer agents, structure-activity relationship of these compounds as both inhibitors of glucose transport and cancer cell proliferation were investigated. Based on these two compounds a number of derivatives were prepared in order to understand the need for the trihydroxyphenyl ester and the need for three of these esters on the central aromatic ring.

The desired analogs were prepared by the acylation of a series of di- and tri-hydroxy benzenes with a group of substituted benzoyl halides. A group of mono-, di-, and trihydroxybenzoyl halides as well as methoxybenzoyl halides were chosen as acylating agents. The synthesis of the hydroxybenzoyl halides is outlined in Scheme 1. Commercially available phenols 3a-f were perbenzylated and the resulting esters hydrolyzed and the acid converted to the acid chlorides 5a and benzyloxybenzoyl chlorides 5b, 5c, 5d, 5e, and 5f. The requisite methoxy-substituted benzoyl halides were prepared from the commercially available carboxylic acids.

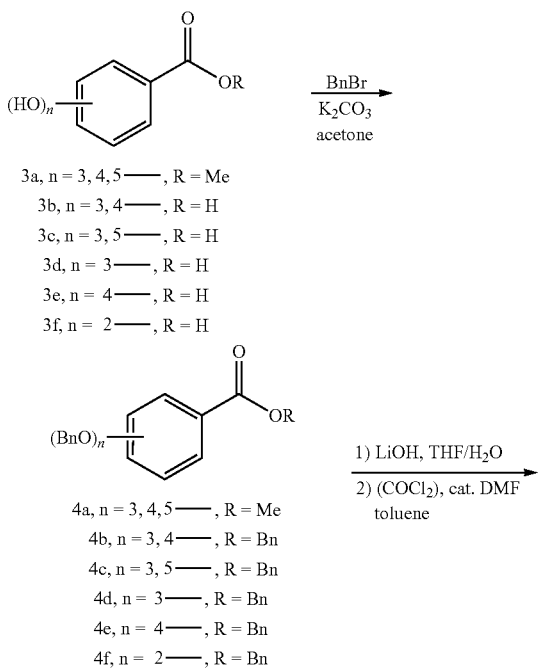

Scheme 1. Synthesis of the benzyloxybenzoyl chlorides 5

TABLE 2

Compounds prepared, their induced inhibitory activities in basal glucose transport and cell growth in H1299 lung cancer cells

| Compound # | Ar/Ar' | X | Y | Yield[a] (%) | Glucose transport inhibition[b] (%) | Cell growth inhibition[b] (%) |
|---|---|---|---|---|---|---|
| 1a | 3,4,5-(OH)$_3$—C$_6$H$_2$ | OMe | H | 69 | 58.4 ± 1.0[c] | 36.0 ± 6.1 |
| 2a | 3,4,5-(OH)$_3$—C$_6$H$_2$ | — | — | 78 | 86.1 ± 1.0 | 39.9 ± 5.0 |
| 1b | 3,4,5-(OH)$_3$—C$_6$H$_2$ | H | Cl | 69 | 84.4 ± 0.1 | — |
| 1c | 3,4,5-(OH)$_3$—C$_6$H$_2$ | F | H | 78 | 81.1 ± 1.1 | — |
| 1d | 3,4,5-(OH)$_3$—C$_6$H$_2$ | H | H | 65 | 32.1 ± 6.2 | — |
| 9a | 3,4,5-(OMe)$_3$—C$_6$H$_2$ | — | — | 86 | 41.1 ± 1.5 | — |
| 7a | 3,4,5-(OMe)$_3$—C$_6$H$_2$ | OMe | H | 90 | 33.3 ± 3.6 | 22.2 ± 3.4 |
| 7b | 3,4,5-(OMe)$_3$—C$_6$H$_2$ | H | Cl | 89 | 1.7 ± 1.1 | 20.6 ± 2.1 |
| 7c | 3,4,5-(OMe)$_3$—C$_6$H$_2$ | F | H | 87 | 7.9 ± 2.6 | 19.6 ± 3.6 |
| 9b | 2,6-(OMe)$_2$—C$_6$H$_3$ | — | — | 69 | 75.8 ± 4.2 | — |
| 9c | 3,4-(OMe)$_2$—C$_6$H$_3$ | — | — | 78 | 0 ± 3.9 | 10.0 ± 1.1 |
| 9d | 3-(OMe)—C$_6$H$_4$ | — | — | 92 | 66.2 ± 1.8 | — |
| 7d | 3-(OMe)—C$_6$H$_4$ | OMe | H | 96 | 32.1 ± 0.2 | 18.3 ± 4.3 |
| 2b | 3,5-(OH)$_2$—C$_6$H$_3$ | — | — | 81 | 98.7 ± 0.8 | 41.0 ± 5.5 |
| 1e | 3,5-(OH)$_2$—C$_6$H$_3$ | OMe | H | 78 | 69.4 ± 3.0 | — |
| 1f | 3,5-(OH)$_2$—C$_6$H$_3$ | H | Cl | 87 | 95.2 ± 0.2 | 38.8 ± 6.9 |
| 1g | 3,5-(OH)$_2$—C$_6$H$_3$ | F | H | 81 | 94.0 ± 0.8 | 35.0 ± 7.6 |
| 2c | 3,4-(OH)$_2$—C$_6$H$_3$ | — | — | 81 | 94.7 ± 0.4 | 42.2 ± 6.1 |
| 1h | 3,4-(OH)$_2$—C$_6$H$_3$ | OMe | H | 78 | 0 | 32.4 ± 2.7 |
| 1i | 3,4-(OH)$_2$—C$_6$H$_3$ | H | Cl | 87 | 94.4 ± 0.4 | 45.2 ± 7.6 |
| 1j | 3,4-(OH)$_2$—C$_6$H$_3$ | F | H | 81 | 88.7 ± 1.8 | 41.5 ± 5.5 |
| 2d | 2-(OH)—C$_6$H$_4$ | — | — | 88 | 74.7 ± 2.0 | — |
| 1k | 2-(OH)—C$_6$H$_4$ | OMe | H | 91 | 50.5 ± 7.6 | 18.0 ± 4.4 |
| 1l | 2-(OH)—C$_6$H$_4$ | H | Cl | 92 | 51.6 ± 5.9 | 26.6 ± 2.3 |
| 1m | 2-(OH)—C$_6$H$_4$ | F | H | 89 | 51.0 ± 6.6 | — |
| 2e | 4-(OH)—C$_6$H$_4$ | — | — | 81 | 88.7 ± 2.5 | 34.8 ± 7.7 |
| 1n | 4-(OH)—C$_6$H$_4$ | OMe | H | 78 | 86.5 ± 2.8 | 36.6 ± 6.7 |
| 1o | 4-(OH)—C$_6$H$_4$ | H | Cl | 87 | 79.0 ± 8.7 | — |
| 1p | 4-(OH)—C$_6$H$_4$ | F | H | 84 | 92.6 ± 0.7 | 35.9 ± 4.7 |
| 1q | 4-(OH)—C$_6$H$_4$ | H | H | 82 | 57.5 ± 2.9 | — |
| 2f | 3-(OH)—C$_6$H$_4$ | — | — | 81 | 99.7 ± 0.1 | 59.3 ± 4.9 |
| 1r | 3-(OH)—C$_6$H$_4$ | OMe | H | 78 | 79.0 ± 8.7 | — |
| 1s | 3-(OH)—C$_6$H$_4$ | H | Cl | 87 | 93.1 ± 1.7 | 44.5 ± 5.2 |
| 1t | 3-(OH)—C$_6$H$_4$ | F | H | 81 | 92.8 ± 0.1 | 40.8 ± 5.6 |

[a]Overall yield from 6 to 8.
[b]Untreated cells served as negative controls (0% inhibition).
[c]Data were presented as mean ± standard deviation.

-continued

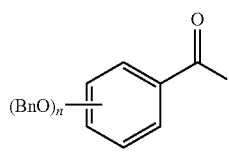

5a, n = 3, 4, 5 ——, 68%
5b, n = 3, 4 ——, 74%
5c, n = 3, 5 ——, 75%
5d, n = 3 ——, 82%
5e, n = 4 ——, 81%
5f, n = 2 ——, 77%

In terms of the core aromatic ring, pyrogallol 8 (present in 2a) and 3-methoxycatechol 6a (X=OMe, Y=H, present in 1a) were chosen. Two halogen substituted phenols, 6b (X=H, Y=Cl) and 6c (X=F, Y=H) were chosen to provide a p-donor (similar to the methoxy group) but electron withdrawing group. An unsubstituted catechol 6d (X, Y=H) was included. As shown in Scheme 2, each of these phenols was then coupled to each of the acid chlorides 5a-f and several methoxy-substituted benzoyl chlorides. After coupling, the benzyloxy esters were deprotected via catalytic hydrogenation. The overall yields are shown in Table 2.

Scheme 2. Synthesis of analogs 1, 2, 7, and 9

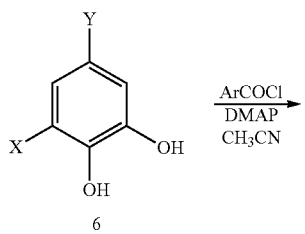

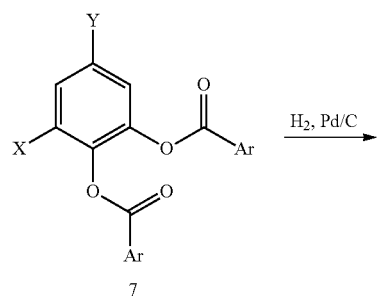

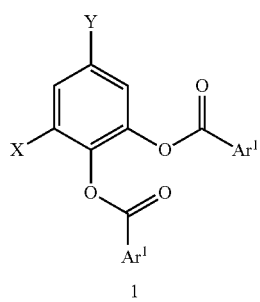

-continued

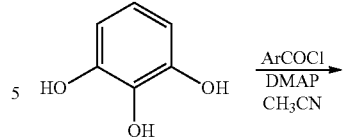

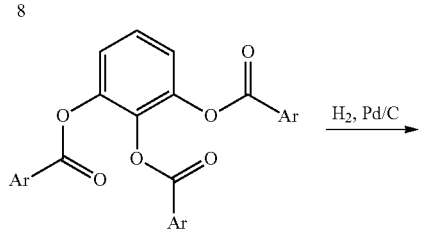

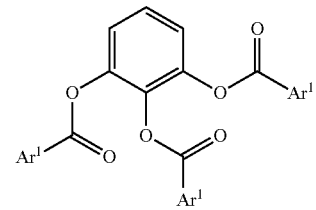

As shown in Table 2, compounds were tested in a standard glucose uptake assay. Briefly, H1299 cancer cells were treated with or without the compounds (30 µM) in triplicates for 10 min before the glucose uptake assay. Cellular glucose uptake was measured by incubating cells in the glucose-free KRP buffer with 0.2 Ci/mL [$^3$H]2-deoxyglucose (specific activity, 40 Ci/mmol) for 30 min in the absence or presence of compounds. After the cells were washed with ice-cold PBS and lysed by 0.2 N NaOH, the cell lysates were transferred to scintillation counting vials and the radioactivity in the cell lysates was quantified by liquid scintillation counting. Cell growth measurements were performed using an MTT assay in hexads in a 96-well tissue culture plate with 5,000 cells plated in each well. The cells were incubated in presence or absence of the compounds (30 µM) for 48 h. After incubation, cell viabilities were assayed using a 96-well SPECTRAMAX™ absorbance/fluorescence plate reader (Molecular Devices).

In some embodiments, comparison of compounds 1a and 2a to derivatives in which the core aromatic ring was substituted with a fluorine or chlorine (1b and 1c), revealed that both of these compounds have similar activity in the glucose transport inhibition assay as compound 2a and were significantly better than 1a. Clearly the halogen substitution on the core aromatic ring is important. An unsubstituted core aromatic ring 1d showed lower levels of inhibition relative to 1a and 2a. In order to determine the necessity of the phenolic hydroxyl groups we prepared several derivatives of 1a and 2a in which the OH group was replaced with a methoxyl group (9a-d, 7a-d). These compounds showed uniformly lower levels of inhibition of glucose transport. Only compounds 9b and 9d (2,6-dimethoxybenzoyl and 3-methoxybenzoyl) showed moderate levels of inhibition.

In some embodiments, the phenolic hydroxyl groups were systematically removed preparing a series of di-hydroxyl and mono-hydroxyl derivatives. The 3,5-dihydroxy and 3,4-dihydroxyl derivatives overall showed good levels of glucose transport inhibition. In both series the tribenzoyl derivatives (2b and 2c) as well as the fluoro- and chloro-substituted derivatives showed >90% inhibition while the methoxy-substituted derivatives (1e and 1h) showed little to no inhibition. All of the compounds showing >90% glucose transport inhibition also show ~40% decrease in cancer cell growth rate.

In some embodiments, removing an additional hydroxyl group provided a set of monohydroxyl compounds at the 2-, 3-, and 4-positions. The 2-hydroxyl series showed uniformly poorer inhibition of glucose transport. The 4-hydroxyl series while showing poorer inhibition of glucose transport did provide compounds with >85% inhibition of glucose transport. These compounds showed a >35% decrease in cancer cell growth rate. The 3-hydroxyl series showed excellent inhibition of glucose transport with the tribenzoyl derivative 2f showing >99% inhibition of glucose transport. This compound also showed the highest level of cell growth inhibition at ~60%. By analyzing all data in Table 2, it was found that the linear correlation coefficient R=0.817 (R2=0.667), indicating that approximately ⅔ (66.7%) of the inhibitory activity of cancer cell growth came from the inhibitory activity of basal glucose transport.

In general, the presence of a hydroxy group at the 3-position of the pendant benzoyl group is important for both inhibitions of glucose transport and cancer cell growth. This 3-hydroxy group can be attached to a chloro- or fluoro-substituted core benzene ring or be part of a tribenzoyl system. Unsubstituted or electron-donating substituents lead to significant decreases in the inhibition of glucose transport activity.

In other embodiments, the hydrolysis products (8, 6c, 10, 11, and 12) of the phenolic esters may exhibit glucose uptake inhibition activity. As shown in FIG. 2, none of these compounds had any glucose uptake inhibition activity. Similarly, none of these compounds showed any activity in anticancer screens. In summary, a library of multiphenolic ester compounds as novel inhibitors of basal glucose transport and anticancer agents with a potential new target, basal glucose transport, were synthesized.

Potent and Selective Inhibitors of Basal Glucose Transport have been Identified Through an SAR Study During a structure activity relationship (SAR) study in which more than 80 PGG analogs were synthesized and analyzed by glucose uptake assay and functional assays, a group of inhibitors for glucose uptake, which had an opposite activity as PGG, were also identified. It was serendipitously discovered that these inhibitors caused inhibition of cancer cell growth and cancer cell death. With these new findings, it was decided to chemically synthesize more potent and selective inhibitors and use them for cancer study.

Figure 16:
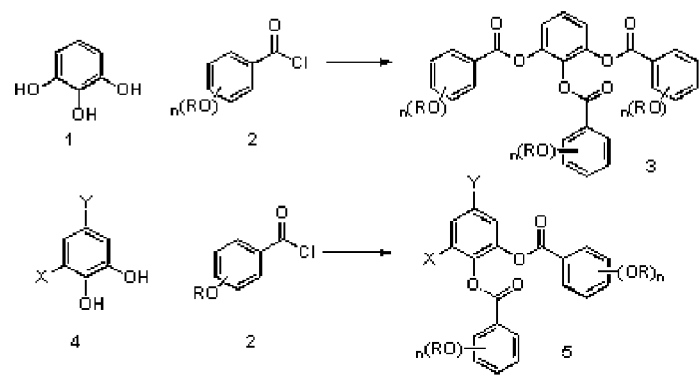
FIG. 16 shows new PGG derivatives.
Figure 17:
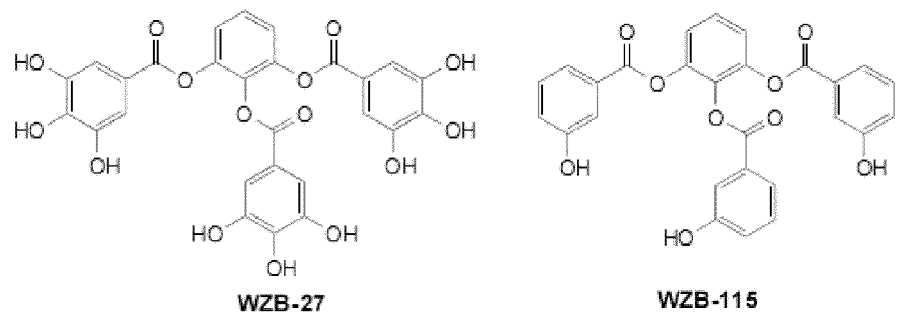
FIG. 17 shows the structure of two tested compound inhibitors. Compounds WZB-27 and WZB-115 are polyphenolic compounds derived from PGG. Unlike PGG, they do not have insulin-like glucose uptake stimulatory activity. On the contrary, they only possess potent glucose transport inhibitory activity and anticancer activity as demonstrated in glucose uptake and MTT cell viability assays.

Given the tight SAR of the initial set of PGG analogs, it was hypothesized that a more rigid scaffold upon which the galloyl group was appended might provide enhanced potency and selectivity. Several new analogs of the PGG class of compounds were prepared. Two compounds were based upon an aromatic nucleus (as opposed to the glucose nucleus). The hypothesis for all compounds was that the rigid central core would prevent any conformational mobility associated with the glucose nucleus. When these compounds (WZB-26 and WZB-27) were assayed, it was found that they possessed basal glucose transport inhibitory activity without any insulin-like activity. Thus, these compounds are selective inhibitors of basal glucose transport of animal cells. When these compounds were used to treat different cancer cell lines, they were found to also inhibit basal glucose transport in cervical (HeLa), colon (RKO), and breast (MCF7) cancer cells. This result suggests that these compounds are general basal glucose transport inhibitors; inhibiting all three cancer cell lines tested. Based on these two compounds a number of derivatives were prepared in order to understand the need for the trihydroxyphenyl ester and the need for three of these esters on the central aromatic ring (FIG. 16). In brief, a series of di- or trihydroxybenzenes were acylated with a protected hydroxybenzoic acid. After coupling the protecting group (benzyl) was removed to provide the target compounds, either a tribenzoyl derivative (3) or a phenyl substituted dibenzoyl derivative (5).

Compounds WZB-26 and WZB-27 were the first compounds prepared. Both compounds showed similar inhibition of basal glucose transport (~85%). Initially, the substitution pattern on the central aromatic ring was of interest. As WZB-27 has three galloyl group while WZB-26 has only 2 but an additional methoxy group. Preparation of multiple compounds was completed to explore the impact other substituents on the central aromatic ring would have upon the levels of inhibition. In some embodiments, the compounds prepared may be designated WZB-89 (F substitution), WZB-90 (C1 substitution), and WZB-110 (H substitution). Both WZB-89 and WZB-90 showed similar levels of activity to WZB-26 and -27 while the unsubstituted WZB-101 showed dramatically decreased levels of activity. Clearly some type of π-donor group in the 3- or 4-position as seen in WZB-26, -27, -89, and -90 is beneficial to activity. Both WZB-26 and WZB-27 have three phenolic hydroxyl groups. In order to determine if these hydroxyl groups were acting as H-bond donors or H-bond acceptors, 4 analogs in which the OH group was replaced with an OMe group (WZB-76, -81, -101, -102) were prepared. The activity of these compounds was dramatically decreased, clearly indicating the need for an H-bond donor (i.e. a phenolic OH). Next, the need for the galloyl group (i.e. 3,4,5-trihydroxybenzoyl) was examined by a systematic removal of the hydroxy group. A series of dihydroxy (3,5-dihydroxy and 3,4-dihydroxy) and monohydroxy (2-OH, 3-OH, and 4-OH) derivatives were prepared. In all cases analogs with a methoxy group or no substitution on the central aromatic ring provided significantly lower levels of inhibition regardless of the number or position of hydroxyl groups on the pendant benzoyl ester. Of the analogs prepared the 3,5-dihydroxy (WZB-111, WZB-113, WZB-114), the 3,4-dihydroxy (WZB-119, WZB-121, WZB-112) and the 3-monohydroxy (WZB-115, WZB-117, WZB-118) derivatives showed inhibition levels of 95-99%. As there is an interest in the pharmaceutical industry to develop simpler, lower molecular weight inhibitors, compounds WZB-27 and WZB-115 were used for biological studies first and better compounds would be employed in later synthesis and assays. Table 3 indicates that we have systematically synthesized more than 100 different compounds to study SAR of the compounds with an objective of making more potent and selective inhibitors to basal glucose transport. As shown in Table 3, some of these inhibitors are the best basal glucose transport inhibitors reported to date and may be useful for future clinical studies.

TABLE 3

Analogs prepared and basal glucose transport inhibition

| Compound # | X | Y | (OR)$_n$ | % inhibition$^a$ |
|---|---|---|---|---|
| WZB-26 | OMe | H | 3,4,5-(OH)$_3$ | 84.0 ± 1.9 |
| WZB-27 | NA, tribenzoyl analog 3 | | 3,4,5-(OH)$_3$ | 86.1±1.0 |
| WZB-89 | F | H | 3,4,5-(OH)$_3$ | 81.0 ± 1.1 |
| WZB-90 | H | Cl | 3,4,5-(OH)$_3$ | 84.4 ± 0.1 |
| WZB-110 | H | H | 3,4,5-(OH)$_3$ | 32.1 ± 6.2 |
| WZB-76 | NA, tribenzoyl analog 3 | | 3,4,5-(OMe)$_3$ | 41.1±1.5 |
| WZB-81 | OMe | H | 3,4,5-(OMe)$_3$ | 33.3 ± 3.6 |
| WZB-101 | F | H | 3,4,5-(OMe)$_3$ | 7.9 ± 2.6 |

TABLE 3-continued

Analogs prepared and basal glucose transport inhibition

| Compound # | X | Y | (OR)$_n$ | % inhibition[a] |
|---|---|---|---|---|
| WZB-102 | H | Cl | 3,4,5-(OMe)$_3$ | 1.7 ± 1.1 |
| WZB-111 | NA, tribenzoyl analog 3 | | 3,5-(OH)$_2$ | 99.5±0.3 |
| WZB-112 | OMe | H | 3,5-(OH)$_2$ | 69.4 ± 3.0 |
| WZB-112 | OMe | H | 3,5-(OH)$_2$ | 69.4 ± 3.0 |
| WZB-113 | F | H | 3,5-(OH)$_2$ | 96.7 ± 1.6 |
| WZB-114 | H | Cl | 3,5-(OH)$_2$ | 96.1 ± 0.1 |
| WZB-119 | NA, tribenzoyl analog 3 | | 3,4-(OH)$_2$ | 94.7±0.4 |
| WZB-120 | OMe | H | 3,4-(OH)$_2$ | 0 |
| WZB-121 | F | H | 3,4-(OH)$_2$ | 88.7 ± 1.8 |
| WZB-122 | H | Cl | 3,4-(OH)$_2$ | 94.4 ± 0.4 |
| WZB-91 | NA, tribenzoyl analog 3 | | 4-OH | 88.7±2.5 |
| WZB-92 | F | H | 4-OH | 92.6 ± 0.7 |
| WZB-93 | OMe | H | 4-OH | 86.5 ± 2.8 |
| WZB-94 | H | Cl | 4-OH | 79.0 ± 8.7 |
| WZB-103 | H | H | 4-OH | 57.5 ± 2.9 |
| WZB-115 | NA, tribenzoyl analog 3 | | 3-OH | 99.7±0.1 |
| WZB-116 | OMe | H | 3-OH | 79.0 ± 8.0 |
| WZB-117 | F | H | 3-OH | 98.3 ± 8.0 |
| WZB-118 | H | Cl | 3-OH | 96.5 ± 0.4 |
| WZB-127 | NA, tribenzoyl analog 3 | | 2-OH | 74.7±2.0 |
| WZB-128 | OMe | H | 2-OH | 50.5 ± 7.6 |
| WZB-129 | F | H | 2-OH | 51.0 ± 6.6 |
| WZB-130 | Cl | H | 2-OH | 51.6 ± 5.9 |

Figure 5A:
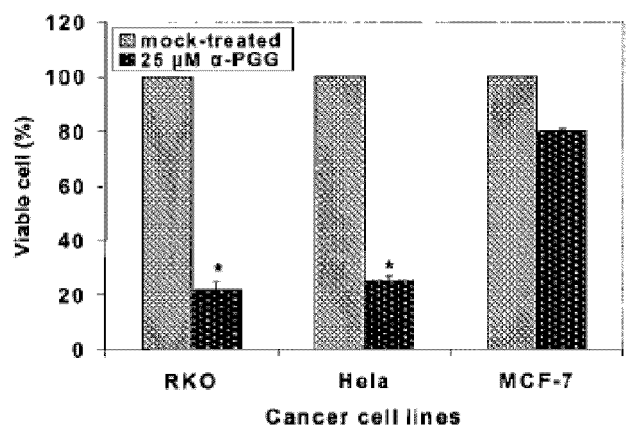
FIG. 5 shows α-PGG treatment induces cell death in cancer cells and the cell death was primarily mediated by apoptosis. Panel A shows α-PGG treatment led to 70-80% reduction of cell viability as measured by a cell viability (MTT) assay. Panel B shows α-PGG treatment resulted in more than 2-fold increase in apoptosis in HeLa cells as measured by an apoptosis (ELISA) assay. Panel C shows α-PGG treatment of HeLa cells led to a decrease in G1 phase cells but a significant increase (~3-fold) in apoptotic cells as determined by an antibody-coupled flow cytometry study.
Figure 5B:
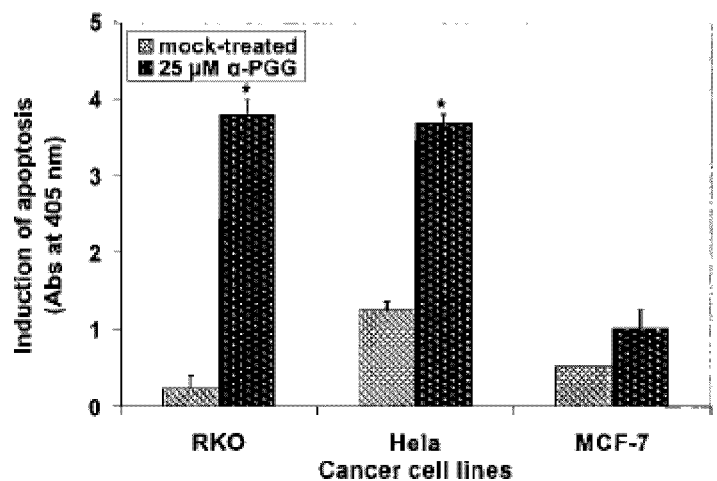
Figure 5C:
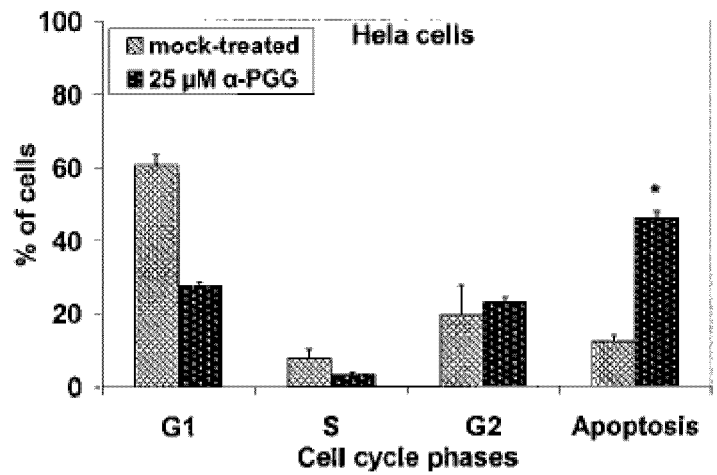

[a]Compounds were tested at 30 µM in H1299 cells by the glucose uptake assay. Cells without being treated by any compound served as negative controls (0% inhibition).
α-PGG induces apoptosis in human colon, cervical, and breast cancer cells When α-PGG was used to treat RKO (colon), HeLa (cervical), and MCF-7 (breast) human cancer cells, it was found that the treatment resulted in pronounced cell death (FIG. 5A), and the cell death was caused primarily, if not exclusively, by apoptosis (FIGS. 5B & 5C). α-PGG does not cause much apoptosis in normal (non-cancer) cells (data not shown), indicating the compound shows increased cytotoxicity more towards cancer cells.

PGG-Derived Compounds Induce Cell Death Preferentially in Cancer Cells than their Normal Counterparts Cancer cells heavily depend on glucose as their preferred energy source and glucose deprivation has been proposed as an anti-cancer strategy. In order for these compounds to be effective anti-cancer agents, they must be able to kill more cancer cells than normal cells. Cell killing (or cell viability) assays revealed that some of these compounds, particularly WZB-27 (=W27), preferentially kill cancer cells (NSCLC H1299 and breast carcinoma MCF7) than their non-cancerous cell counterparts (NL20 or MCF12A cells, Table 3). These results suggest that these compounds have excellent potential to be anti-cancer agents. Based on this observation, it was speculated that optimal compounds and drug concentration can be determined that will minimally impact normal cells while causing maximal damage to cancer cells.

Comparative assays using WZB-27, WZB-115, as well as two known anticancer drugs, cisplatin and taxol, were completed. In Table 4, the percent cell death in cancer cell lines as well as normal cell lines is shown. Compounds WZB-27 and WZB-115 kill approximately the same percent of lung cancer cell line H1299 as taxol while killing significantly less of the normal lung cell line, NL20. Comparing the breast cancer cell line MCF7, WZB-27 and WZB-115 kill somewhat fewer cells relative to taxol but more than cisplatin. Both WZB-27 and WZB-115 kill fewer of the normal breast cell line MCF12A than taxol or cisplatin. WZB-27 kills fewer of the normal breast cell line MCF12A than taxol or cisplatin while WZB-115 kills no more normal cells than either cisplatin or taxol. The results shown in table 4 suggest that compounds have cytotoxicities in cancer cells comparable or better than cisplatin and/or taxol while they exhibit less cytotoxicities in non-cancerous ("normal") cells than the anticancer drugs.

TABLE 4

Comparison of % cell death in cancer vs. normal cells induced by compounds[a, b, c]

| Compound | H1299 | NL20 | MCF7 | MCF12A |
|---|---|---|---|---|
| Cisplatin | 26.4 ± 3.8 | 58.4 ± 7.0 | 27.0 ± 1.9 | 69.6 ± 2.9 |
| Taxol | 45.6 ± 4.9 | 53.8 ± 4.2 | 61.4 ± 7.1 | 73.7 ± 5.6 |
| WZB-27 | 52.3 ± 9.4 | 0 | 48.9 ± 5.7 | 21.1 ± 8.9 |
| WZB-115 | 61.3 ± 3.6 | 34.1 ± 8.7 | 51.6 ± 8.3 | 66.0 ± 8.6 |

[a]This test is done using a standard MTT assay to measure viable cells after compound treatment.
[b]Concentration used in the test was the IC$_{50}$ for each compound.
[c]Non-compound treated cells were used as controls (0% death)

Figure 6:
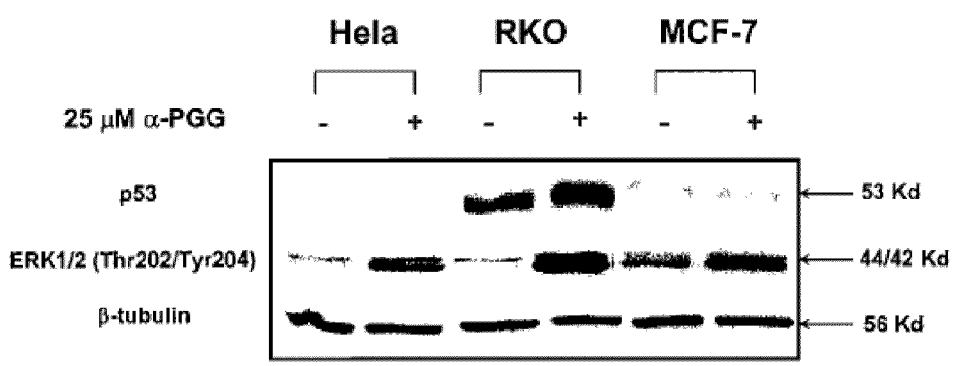
FIG. 6 shows p53 activation and inactivation as determined by Western blot analyses. When HeLa, RKO, or MCF-7 cells were treated with 25 µM α-PGG, p53 protein was found not to be activated in HeLa cells but was activated in RKO cells.
Figures 19A, 19B:
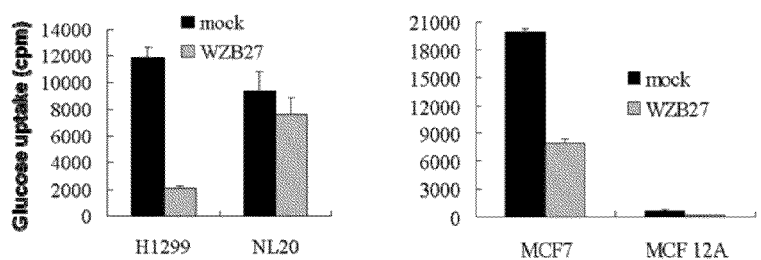
FIG. 19 shows cancer cells express more GLUT1 protein and are inhibited more by compounds in glucose uptake more their non-cancerous counterparts. Cancer cells and their non-cancerous counterparts were treated with or without compounds and then measured for their respective glucose uptakes. A. glucose uptake assay of H1299 lung cancer cells and their non-cancerous NL20 cells treated with or without WZB-27. B. Glucose uptake assay of MCF7 cancer cells and their non-cancerous MCF12A cells. C. Western blot analysis of GLUT1 protein expression in cancer and non-cancerous cells using antibody specific against GLUT1 (H43 fragment). β-actin served as protein loading control.
Figure 19C:
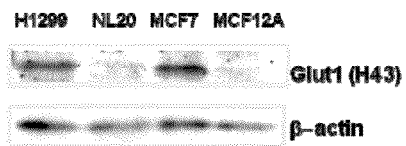

Cancer Cell Lines Overexpress GLUT1 and Compounds Inhibit More Glucose Uptake in Cancer Cells than their Non-Cancerous Cell Counterparts To determine the possible causes for increased killing in cancer cells than in their non-cancerous cell counterparts, comparison studies were conducted to determine the effect of compound treatment on glucose uptake. It was found that compound WZB-27 produced larger reductions in glucose uptake in cancer cell line H1299 and MCF7 as compared to the reduction in non-cancerous cell lines NL20 or MCF12A (FIGS. 19A and 19B). Western blot analysis revealed that these same cancer cell lines express significantly higher levels of GLUT1 protein than their non-cancerous counterparts (FIG. 19C). The larger reduction in glucose uptake observed in cancer cell lines was correlated with higher GLUT1 levels in these cells.

α-PGG Activates p53 in RKO (Colon) Cells but not in HeLa (Cervical) or MCF-7 (Breast) Cancer Cells After it was found that α-PGG induced apoptosis in the three cancer cell lines, knowledge of the mechanism of apoptosis was sought (i.e., is apoptosis related to p53 status or not). Western blot analysis using anti-p53 antibody revealed that α-PGG led to activation of p53 in RKO cells but not in HeLa or MCF-7 cells (FIG. 6). This result suggests that the apoptosis induced in HeLa and MCF-7 cells was p53-independent. This result is both interesting and important in that it shows that α-PGG can induce apoptosis in certain cancer cells using a p53-independent mechanism, which should be effective in inducing apoptosis in more than 50% of all human cancers in which p53 is mutated and non-functional.

This result suggests that, unlike in RKO cells, the apoptosis induced by α-PGG in HeLa cells and MCF-7 was not mediated by p53 or p53 signaling pathway. Thus, apoptosis induced by α-PGG in HeLa cells is p53-independent.

Figure 7:
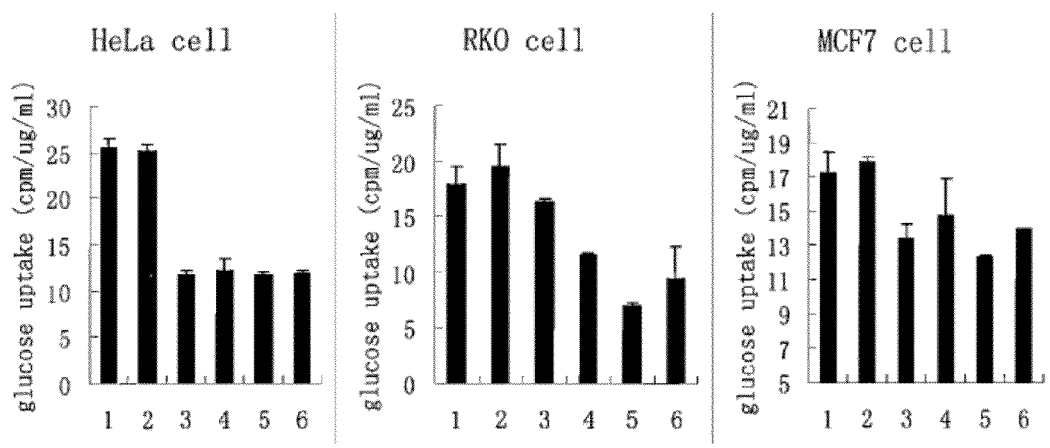
FIG. 7 shows α-PGG and its derivatives inhibit glucose uptake in HeLa, RKO, and MCF-7 cancer cells. Cells were treated with α-PGG for 20 minutes before $^3$H-labeled 2-DG. Thirty minutes after the addition of 2-DG, cells were harvested, lysed, and counted for their respective glucose uptake. Samples: 1. Mock; 2. Insulin (100 nM); 3. α-PGG (30 µM); 4. WZB-25 (30 µM); 5. WZB-26 (30 µM); and 6. WZB-27 (30 µM).

PGG and its Derivatives Inhibit Basal Glucose Transport in Human Cancer Cell Lines Inhibition of basal glucose transport was speculated as a cause for cancer cell death induced by α-PGG. PGG derivatives were synthesized and tested along with α-PGG in different human cancer cell lines. These derivatives were found to inhibit basal glucose transport in cervical, colon, and breast cancer cell lines (FIG. 7).

Figure 8A:
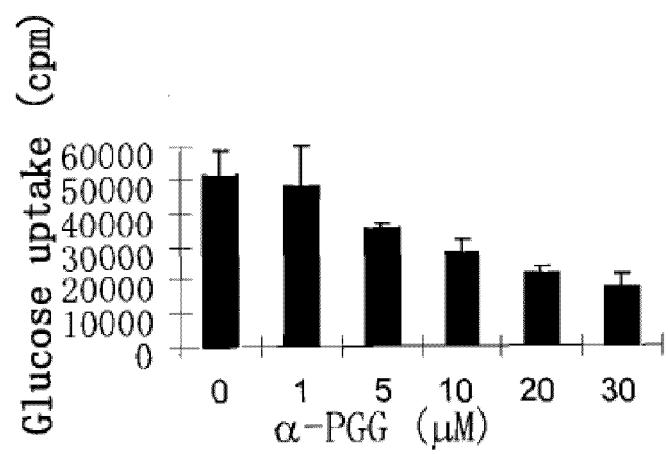
FIGS. 8A-C show α-PGG and its derivatives inhibit basal glucose transport in HeLa cells in dose-dependent manners.
Figure 8B:
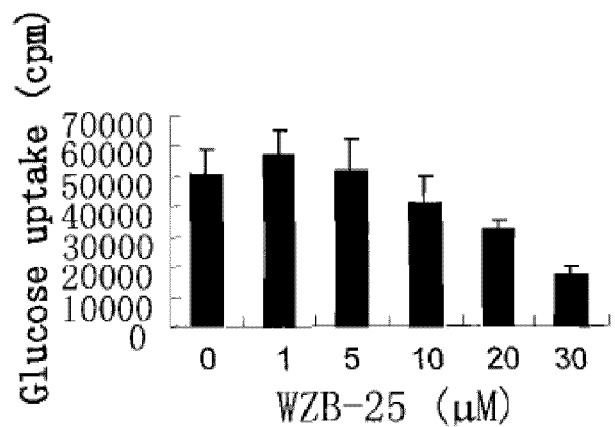
Figure 8C:
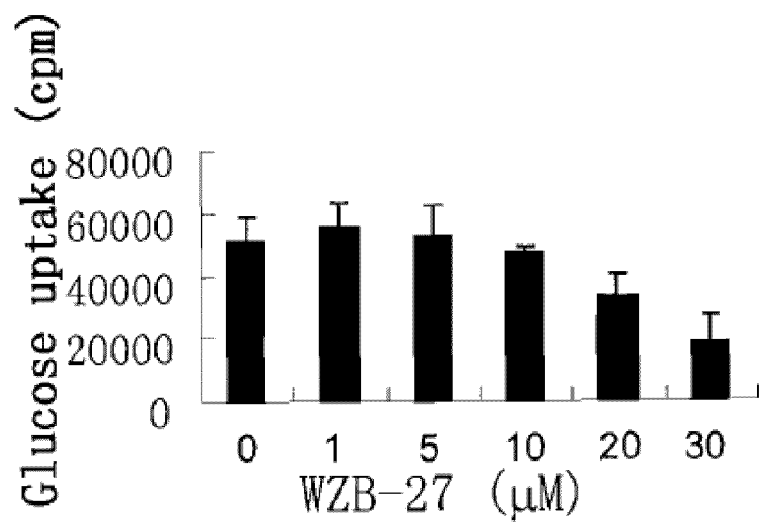
Figure 9:
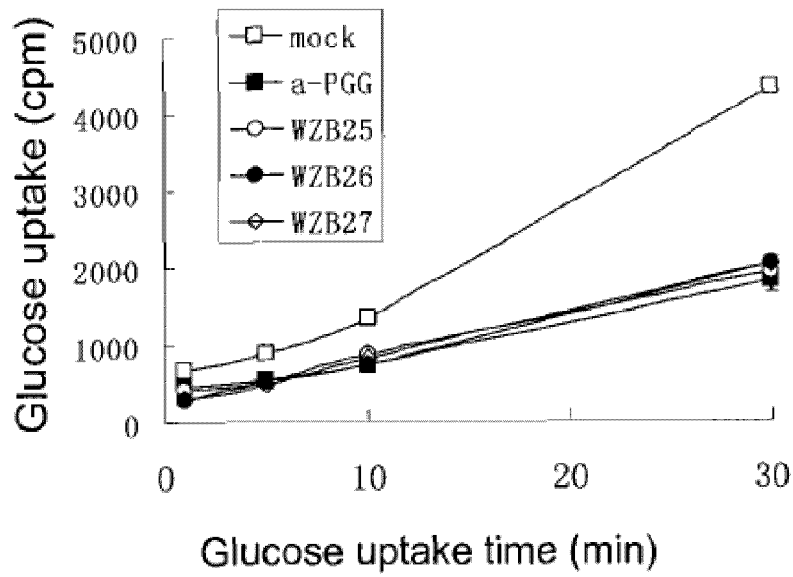
FIG. 9 shows a time course of glucose transport inhibition induced by α-PGG or α-PGG derivatives. The glucose uptake assay was conducted the same way as previously described except that the glucose uptake was terminated at different times (from 1, 5, 10, and up to 30 minutes).

Insulin had no effect on the glucose uptake, suggesting that the glucose measured was basal glucose transport, not insulin-mediated glucose transport. Based on this observation, we further hypothesized that the pronounced glucose transport inhibition might be the cause of apoptosis, particularly in HeLa cells.

α-PGG and its Derived Compounds Inhibit Basal Glucose Transport in Hela Cells in a Dose-Dependent Manner Different concentrations of α-PGG or its derived compounds, WZB-25 and WZB-27, were used to determine if the inhibition of the basal glucose transport was dose-dependent. The experimental results indicated that α-PGG and its derivatives inhibited the basal glucose transport in a dose-dependent manner and α-PGG appears to be slightly more potent than its derivatives in inhibiting the transport (FIG. 8). It was also found that 30 μM of any compound led to approximately 50% inhibition of basal glucose transport in HeLa cells (FIG. 8), suggesting that all 4 compounds were about equally effective in inhibiting basal glucose transport in HeLa cells. This result led us to conclude that we could either use α-PGG or substitute α-PGG with its derivatives to do the glucose transport inhibition study. We have also found that reducing glucose concentration in cell culture media also reduces cell growth rates and induces apoptosis in HeLa and MCF-7 cells in a glucose concentration-dependent manner (data not shown). These results clearly show that α-PGG and its derivatives WZB-25 and WZB-27 inhibit basal glucose transport and the inhibition is dose-independent.

HeLa cells were incubated with α-PGG or its derivatives (WZB-25 or WZB-27) at various concentrations for 20 min before $^3$H-labeled 2-DG was added to the cells for 30 min. After 30 min of 2-DG incubation, cells were harvested, lysed, and counted for their respective glucose uptake (intracellular 2-DG counts) with a scintillation counter. The results show that α-PGG starts to inhibit glucose transport at 5 μM, while other derivatives start to inhibit the transport at about 10 μM and all three compounds show dose-responsive inhibition profiles. Error bars in FIG. 8 represent standard deviations of the measurements. Samples were done in triplicates and the experiment was repeated three times.

Figure 10:
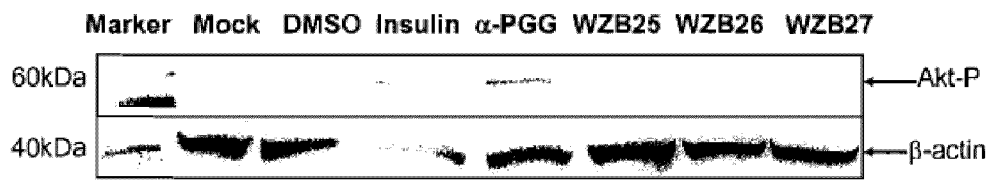
FIG. 10 shows α-PGG induces Akt while α-PGG derivatives do not induce Akt. CHO cells overexpressing the insulin receptor were treated with α-PGG or its derivatives. After treatment, cells were lysed and proteins were analyzed by the antibody specific for phosphorylated Akt.

Unlike α-PGG (an Insulin Mimetic), α-PGG Derivatives do not Induce Akt Phosphorylation So far, it has been shown that α-PGG and its derivatives inhibited basal glucose (FIG. 7) and exhibited very similar dose-response (FIG. 8). However, these derivatives are much smaller than α-PGG in molecular weight and it is expected that these derivatives will be cleaner than α-PGG in that they are more selective and do not have as many activities unrelated to the basal glucose transport inhibition. Previous data showed that α-PGG binds and activates the insulin receptor (IR), and induces the phosphorylation of Akt, a protein factor involved in IR signaling. Since the derivatives are simpler in structure and smaller in size than α-PGG, it was speculated that these derivatives would not induce Akt phosphorylation, which was confirmed by Western blot analyses on compounds-treated CHO cells that overexpress IR (FIG. 10).

Akt is a key factor in the insulin receptor signaling pathway. Therefore, α-PGG derivatives WZB-25 through WZB-27 appear to be more selective than α-PGG in that they do not induce activities unrelated to basal glucose transport. They should generate glucose transport inhibition and apoptosis data that are even easier to analyze and interpret than those of α-PGG.

Figure 12A:
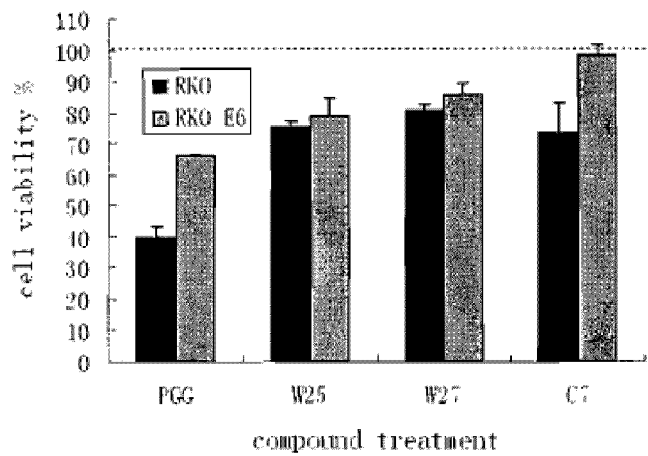
FIG. 12 shows cell viability and apoptotic assays. Panel A shows a cell viability assay in RKO colon cancer cells. RKO cells contain high levels of p53 while RKO E6 cells contain much lower levels of p53. Panel B shows an apoptosis assay in H1299 lung cancer cells using cleaved PARP protein (89 kDa) as an indicator for Caspase 3 since PARP is a substrate of activated Caspase 3.
Figure 12B:
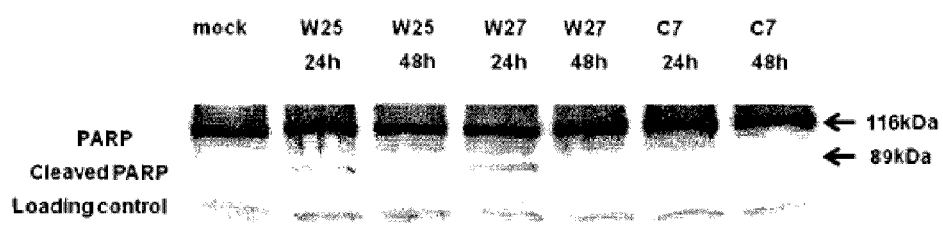

Basal Glucose Transport Inhibitors Induce Apoptosis and Cell Death Using a p53-Independent Signaling Pathway To determine if anti-cancer compounds W25 and W27 kill cancer cells using a p53 dependent or a p53-independent pathway, a cell killing assay was performed in RKO and RKO E6 cell lines. The difference between the two cell lines is that RKO cells contain much higher levels of p53 than RKO E6 cells. The fact that W25 and W27 killed about the same amounts of RKO cells and RKO E6 cells in the assay (FIG. 12A) suggests that p53 in the cancer cell lines did not play any important roles in the cell killing. Furthermore, the PARP assay revealed that, in the W25 and W27 treated H1299 cells, the intact 116 kDa PARP protein was cleaved into a 89 kDa protein (FIG. 12B), indicating that the caspase 3 was activated and caspase 3 apoptosis pathway is active in the compound treated lung cancer cells. These results suggest that the compounds kill cancer cells using a p53-independent and caspase 3-dependent apoptosis pathway.

Figure 18A:
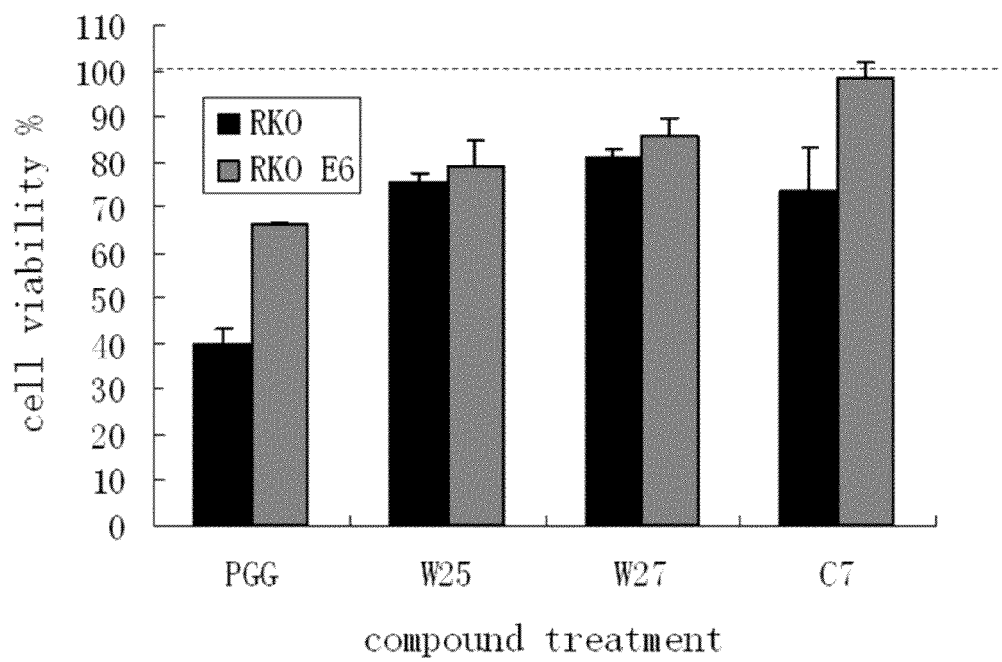
FIG. 18 shows cell viability and apoptosis assays (W25=WZB-25, W27=WZB-27). A. Cell viability assay in RKO colon cancer cells. RKO cells contain high levels of p53 while RKO E6 cells contain much lower levels of p53. B. α-PGG induces stronger viability-lowering effect in RKO than in RKO-E6 cells. RKO cells have higher level of p53 while RKO-E6 is p53 deficient. *p<0.001, p<0.01. C. Apoptosis assay in A549 lung cancer cells using cleaved PARP protein (89 kDa) as an indicator for Caspase 3 since PARP is a substrate of activated Caspase 3. Low glucose (5% of normal) treated samples served as positive controls.
Figure 18B:
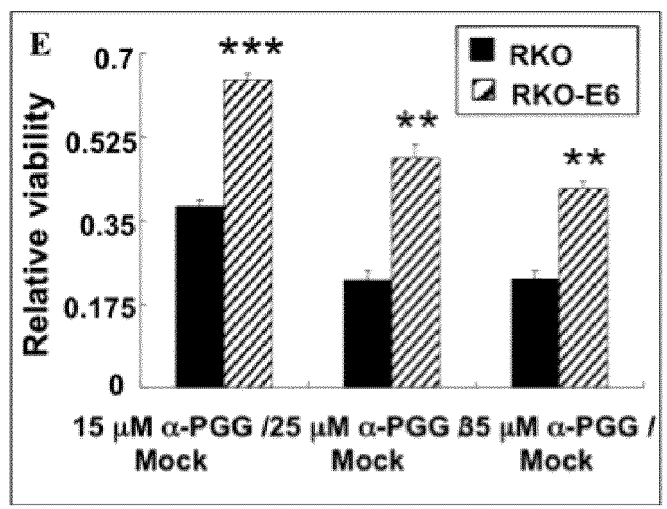

Although it was found that there was no significant difference between the viability of RKO and RKO-E6 cells after they were treated with compound WZB-25 or WZB-27 (FIG. 18A), a significant difference in viability between the two cell lines was observed when they were treated by α-PGG (FIGS. 18A and 18B), suggesting that the apoptosis induced by WZB-25 or WZB-27 is p53-independent, since p53 levels in the two cell lines did not affect cell viability. In contrast, the apoptosis induced by α-PGG is p53-dependent since its treatment led to very different cell viability in the same two cell lines (FIG. 18B). This finding is important because it is known that more 50% of all human cancers harbor p53 mutations. These inhibitors should be able to exert their anticancer effects on all human cancers regardless their p53 status.

Furthermore, a Western blot analysis revealed that, in the WZB-27 and WZB-115 treated A549 cells, the intact 116 kDa PARP protein was cleaved into a 89 kDa protein (FIG. 18C), indicating that the caspase 3 was activated and caspase 3 apoptosis pathway is active in the compound treated lung cancer cells. More interestingly, cells growing in cell culture media containing 5% of normal glucose concentration (1.25 mM vs. 25 mM normal) also demonstrated the cleaved 89 kDa band (FIG. 18C), indicating the glucose withdrawal resulted in the same PARP cleavage. These results suggest that the compounds WZB-27 and WZB-115 induce apoptosis in these cancer cell lines using a p53-independent and caspase 3-dependent apoptosis pathway while α-PGG does this in a different p53-dependent mechanism. It also reveals that cell treatments by the compound inhibitors produced the same PARP cleavage as glucose withdrawal, providing initial experimental evidence that compound treatment mimics the effects produced by glucose withdrawal. This is important since it suggests that the methods of inhibition of basal glucose transport by inhibitors and glucose withdrawal by reducing glucose concentration in cell growth media may be interchangeable when in producing certain biological effects in cells.

Mechanism of Compounds in Cancer Cell Killing

Figure 11:
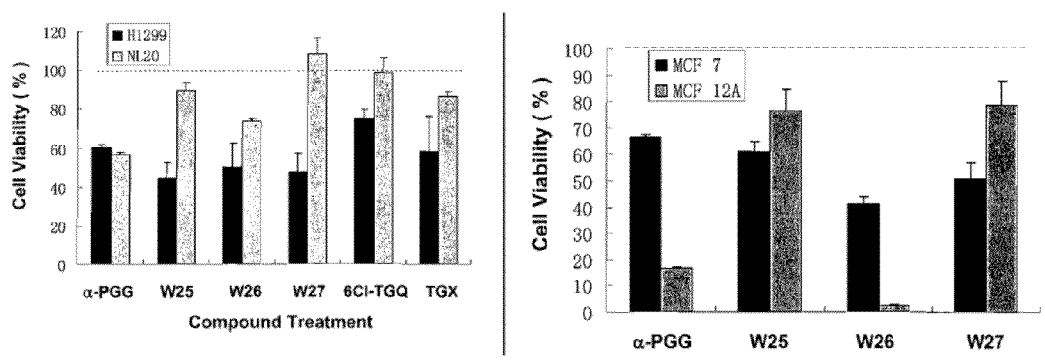
FIG. 11 shows PGG-derived compounds induce more cell death in cancer cells than in their normal cell counterparts. The left panel shows compounds were used to treat human lung cancer cells (H1299) or normal lung cells (NL20) at 25 mM. Forty-eight hours after the treatment, cell viability assay was performed to determine percentage of cell killing. Cells without compound treatment were used as controls (100% baseline). The right panel shows compounds used to treat human breast cancer cells (MCF-7) and normal breast cells (MCF-12A). Cell viability assay was performed at the same conditions as for the lung cancer cells in the left panel.
Figure 13:
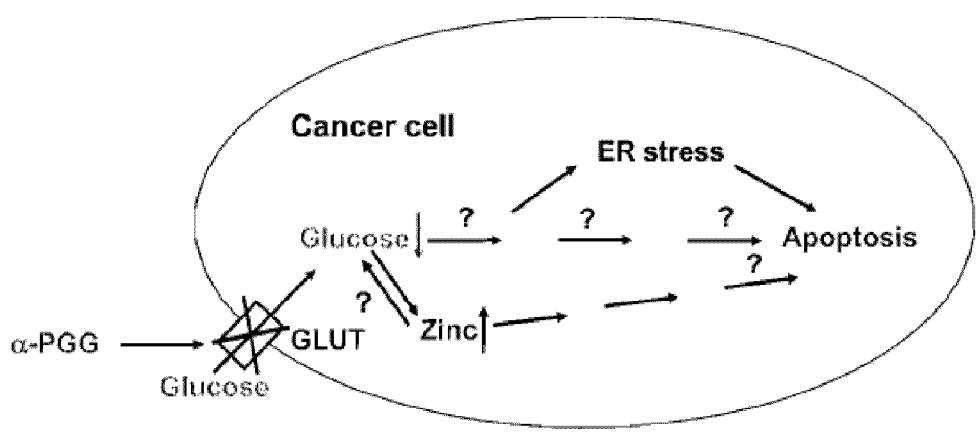
FIG. 13 shows a schematic presentation of glucose transport.

Potential mechanisms for cancer cell killing are graphically presented in FIG. 13. According to the hypothesis, extracellular glucose is taken up by cancer cells through glucose transporter 1 (GLUT1). Compound α-PGG and its derivatives inhibit basal glucose transport by inhibiting GLUT (most likely to be GLUT1). The inhibition of basal glucose transport results in reduction of intracellular glucose concentration and an increase of intracellular free $Zn^{2+}$; these changes, through an unknown mechanism(s), induces ER stress and eventually apoptosis (FIG. 11).

Figure 20:
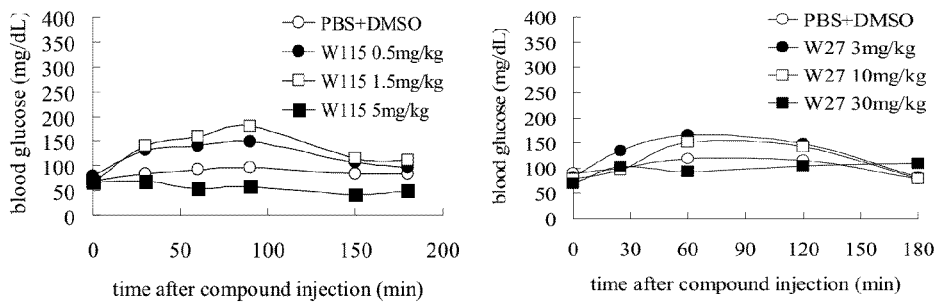
FIG. 20 shows blood glucose levels after compound injection. Compound W27 (=WZB-27) or W115 (=WZB-115) was injected IP into fasting Balb/c healthy mice and blood glucose levels were measured multiple times post injection. N=5 per group. PBS+DMSO group was the vehicle control.

Glucose Transport Inhibitors Induced Mild and Temporary Hyperglycemia in Fasting Mice Inhibitors to basal glucose transport are likely to increase blood glucose level when used in animals because the movement of blood glucose into target cells, primarily muscle and fat cells, is partially blocked by the inhibitors. To find out the intensity and duration of the induced hyperglycemia and other potential side effects in animals, we performed animal studies by injecting two lead compounds WZB-27 and WZB-115 separately and intraperitoneally (IP) into fasting mice and observing blood glucose changes, movement, and behaviors of the compound injected animals. As expected, the compound-injected mice showed mild and temporary hyperglycemia compared to the vehicle-injected group (PBS+DMSO) and the hyperglycemia went away approximately 3 hrs after the compound injection (FIG. 20). Both compounds WZB-27 and WZB-115 showed very similar blood glucose profiles (FIG. 20). At $IC_{50}$ (10 mg/kg for WZB-27 and 1.5 mg/kg for WZB-115), both compounds induced mild and temporary hyperglycemia. Interestingly, at a concentration of $3 \times IC_{50}$, neither compound induced higher hyperglycemia. Instead, injection of $3 \times IC_{50}$ (30 mg/kg for WZB-27 and 5 mg/kg for WZB-115) resulted in blood glucose levels very similar to that of the vehicle injected group (FIG. 20). This experiment was repeated once and similar results were obtained. Although the mechanism for normoglycemia at higher compound concentrations was currently unclear, it was concluded that these compounds do not produce severe hyperglycemia in mice. No Other noticeable changes in animal movement, activity, and behavior were observed in this experiment.

To further address the concerns of animal side effects, a longer-term multiple compound injections at higher concentration were performed. Animals were injected once a day at a concentration of $6 \times IC_{50}$ or $10 \times IC_{50}$ for one week. Similar to the single day experiment, no noticeable side effects were observed except mild and temporary hyperglycemia in both groups and some weight loss for the $6 \times IC_{50}$ group ($\leq 10\%$ of total body weight). There was no significant difference between blood glucose of the compound treated group at the end of the one week study and that of the vehicle treated group. These results strongly suggest that inhibition of basal glucose transport may not be very toxic and are relatively safe to mice. The anticancer animal studies disclosed herein can be carried out to determine the in vivo anticancer efficacy of the compounds.

Comparison of Intracellular Glucose Levels in Glucose Deprivation Induced by Either Glucose Removal or by Inhibition of Basal Glucose Transport Glucose deprivation experiments, in which glucose in the cell culture media is partially removed, have been frequently done. However, the intracellular glucose level changes have not been measured often during or after the deprivation. In order to compare the effects of glucose withdrawal and basal glucose transport inhibition on intracellular glucose levels, a comparison study will be conducted.

H1299 and MCF7 will be incubated in 24-well plates in their regular media with a glucose concentration of 25 mM overnight and intracellular glucose concentrations of the cells should be in equilibrium with the extracellular glucose concentration. The glucose concentration in cell growth media of some wells is reduced by mixing regular glucose-containing medium with glucose-free medium at different ratios to achieve the following final glucose concentrations 25 mM, 10 mM, 2.5 mM, 1 mM, 0.25 mM (1% of the original concentration). The media will be supplemented with of $^3$H-deoxyglucose at 1/50 of the cold glucose concentration and then added to cells. The cells will be incubated for 30, 60, and 120 min, and the intracellular $^3$H-DG will be measured by scintillation counter after media removal and cell lysis as in a standard glucose uptake assay. These samples treated by glucose removal can be considered as positive controls of the experiment. For comparison, cancer cells in wells with regular growth medium supplemented with $^3$H-DG will be treated with different concentrations of known glucose transport inhibitors fasentin, apigenin, or anti-GLUT1 antibody and then have their intracellular $^3$H-DG levels measured at the same times post treatment as the glucose removal samples. Dose response and time response curves can be generated from these data and then compared. These curves will reveal if the glucose removal and inhibition of basal glucose transport lead to the same or different intracellular glucose concentrations. Our in house glucose transport inhibitor WZB-27 and WZB-115 will also be used in the experiment and will be compared to those samples treated by fasentin, apigenin, or anti-GLUT1 antibody. Cells not treated by either glucose withdrawal or compound (but with same amount of radioactive $^3$H-DG) will serve as untreated baseline (negative) controls.

Measurement of GLUT1 Protein and mRNA Levels During Glucose Removal or Inhibition of Basal Glucose Transport It is known that GLUT1 protein and mRNA are down-regulated when glucose is withdrawn. However, it is not known if the inhibition of basal glucose transport induced by fasentin or our inhibitor compounds also results in GLUT1 down-regulation. To answer this question, cancer cells H1299 and MCF7 cells are treated with (1) glucose withdrawal (removal from cell culture media) at multiple glucose concentrations, and (2) inhibition of basal glucose transport by the compounds (fasentin, apigenin, anti-GLUT1 antibody, and compounds WZB-27 and WZB-115) at multiple compound concentrations. After treatments for 1, 2, 4, 8, 12, 24 or 48 hrs, the cells are harvested and total cellular proteins are isolated. A western blot analysis is carried out using anti-GLUT1 antibody (from Santa Cruz) to compare GLUT1 protein levels in the samples of two different treatments. Each GLUT1 protein band will be quantified using densitometry and then normalized with its own β-actin protein loading control, and compared to GLUT1 level in the untreated control samples. The comparison between treated samples and untreated samples will tell us whether the treatments lead to down-regulation of GLUT1 protein. The comparison between samples of glucose removal and samples treated by compounds will show whether these two treatments result in differences in GLUT1, while the comparison between fasentin/apigenin/anti-GLUT1 antibody treated samples and those treated by WZB-27/WZB-115 will reveal the similarity and difference among these compounds.

In the same experiment, total RNA will also be isolated. Commercially available primers unique to GLUT1 will be purchased and used in real-time PCR to quantify GLUT1 mRNA levels in each treatment conditions. GAPDH and/or β-actin mRNA will be used as internal RNA control. Comparisons will be made among these treatments with untreated samples (control) and between glucose removal and inhibition of basal glucose transport by compounds. These comparisons will show whether GLUT1 is also down-regulated at the mRNA level and whether these two treatments lead to different GLUT1 mRNA expression results.

Measurement of Glycolysis Rates Under Different Experimental Conditions

H1299 lung cancer and MCF7 breast cancer cells will be treated with or without glucose removal or inhibitor of basal glucose transport. Glycolysis rates of each treatment condition will be measured by monitoring the conversion of 5-$^3$H-glucose to $^3$H$_2$O, as described previously. Briefly, $10^6$ of H1299 and MCF7 cells are washed once in PBS prior to re-suspension in 1 ml of Krebs buffer and incubation for 30 min at 37° C. Cells are then pelleted, re-suspended in 0.5 ml of Krebs buffer containing glucose (10 mM, if not specified), and spiked with 10 μCi of 5-$^3$H-glucose. Following incubation for 1 h at 37° C., triplicate 50 μl aliquots are transferred to uncapped PCR tubes containing 50 μl of 0.2 N HCl (for stopping the reaction), and a tube is transferred to a scintillation vial containing 0.5 ml of H$_2$O such that the water in the vial and the contents of the PCR tube are not allowed to mix. The vials will be sealed, and diffusion is allowed to occur for a minimum of 24 h (to reach equilibrium). The amounts of diffused and undiffused $^3$H are determined by scintillation counting. Appropriate $^3$H-glucose-only (no cell) and $^3$H$_2$O-only controls will be included in the assay, enabling the calculation of $^3$H$_2$O in each sample and thus the rate of glycolysis. Glucose utilization rate will be calculated as $^3$H H$_2$O formed from $^3$H-glucose, expressed in the term of pmol of glucose utilized/$10^6$ cancer cells from the formula:

$$\text{Glucose utilized}(pmol) = \frac{[^3\text{H}]\text{water formed}(d.p.m.)}{sp.\ \text{radioactivity of } [5-^3\text{H}]\text{glucose}(d.p.m./pmol)}$$

These measurements will enable us to determine how glucose withdrawal and compound inhibition affect glycolysis rates in cancer cells. Untreated cancer cells will be used as baseline controls. Non-cancerous cell counterparts NL-20 (normal lung) cells and MCF12A (normal breast) cells will also be used as controls for comparison.

Glycolytic Enzymes Alteration During Glucose Withdrawal or Basal Glucose Transport Inhibition It has been shown that glucose withdrawal resulted in down-regulation of glycolytic enzymes such as hexokinase and pyruvate kinase (PK). PKM2 has been found to be very important for tumorigenesis and exclusively expressed in cancer or proliferating cells. It is still unclear if inhibition of basal glucose transport by fasentin or our compound inhibitors also leads to similar results. To answer this question, H1299 and MCF7 cancer cells growing in 24-well cell culture plates will be treated with or without anti-GLUT1 antibody, fasentin and our inhibitor compounds WZB-27 and WZB-115 at their respective IC$_{50}$ and IC$_{70}$. After 24 and 48 hr treatment, cells will be harvested and total protein is isolated. Western blot analyses will be performed to compare the levels of PKM2 in the treated and untreated samples using PK antibodies (Cell Signaling). This study will enable us to know exactly what happens to PKM2 when cancer cells are treated with compound inhibitors. Same cancer cells treated with or without glucose withdrawal will be included in the study for comparison.

The activity of hexokinase, the first enzyme in glycolysis, will also be studied by a similar method described for PK. Antibodies against hexokinase are commercially available. In addition, the enzymatic activity of hexokinase will also be measured and used as an indication of changes in glycolysis as hexokinase is the enzyme catalyzing the first rate-limiting step of glycolysis. Hexokinase activity will be measured using a published protocol. Briefly, the activity will be determined spectrophotometrically at 30° C. by coupling the formation of glucose 6-phosphate with its removal via glucose-6-phosphate dehydrogenase, during which the absorbance of NADPH at 340 nm changes. Activity is expressed in mUs, 1 mU defined as the formation of 1 nmol NADPH/min. Enzyme was dissolved in Tris MgCl$_2$ buffer, pH 8.0 to obtain a rate of 0.02-0.04 $\Delta$A/min. The assay medium contained 0.05M Tris MgCl$_2$ buffer, pH 8.0, 15 mM MgCl$_2$, 16.5 mM ATP, 6.8 mM NAD, 0.67 mM glucose, and 1.2 units/ml glucose-6-phosphate dehydrogenase. Incubate in the spectrophotometer at 30° C. for 6-8 minutes to achieve temperature equilibration and establish blank rate, if any. At zero time, add 0.1 ml of diluted hexokinase solution and mix thoroughly. Record increase in absorbance at 340 nm for 3-4 minutes. Determine $\Delta$A/min from initial linear portion of curve.

Calculation will be performed using the formula shown below:

$$\text{Units/mg protein} = \frac{\Delta A_{340}/\text{min}}{622 \times \text{mg enzyme/ml reaction mixture}}$$

Studies Related to Protein Factors Signal Transduction During Glucose Deprivation Induced by Inhibition of Basal Glucose Transport The activation of Akt was found to increase the rate of glycolysis partially due to its ability to promote the expression of glycolytic enzymes through HIF$\alpha$. This was speculated as a major factor contributing to the highly glycolytic nature of cancer cells. It would be also interesting to find out how changes in glucose transport and glycolysis affect expression of Akt. In this experiment, cancer cell H1299 and MCF7 will be treated with or without anti-GLUT1 antibody, fasentin, WZB-27, or WZB-115 at their respective IC$_{50}$. Differentially treated cells will be harvested 1, 2, 4, 8, 24 hrs after the treatment. Total proteins from each sample will be isolated and analyzed by western blots using antibodies specifically against Akt. Akt has multiple phosphorylation sites and different antibodies will be used to distinguish Akt phosphorylated at different sites. Treated samples will be compared to untreated samples and samples with different treatments will also be compared. Changes in intensity of total Akt protein as well as changes in different phosphorylated forms of Akt will specify how inhibition of basal glucose transport affects expression and phosphorylation of Akt. Another protein factor involved cell growth signaling pathway, AMPK, which has been found to affect glycolysis, will also be studied the same way as Akt.

Figure 21:
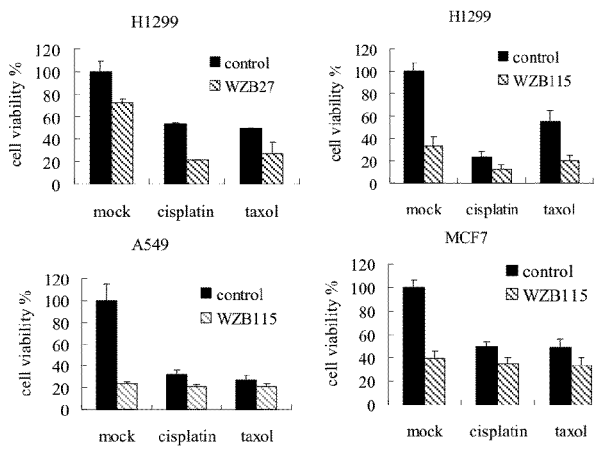
FIG. 21 shows a combination of glucose inhibitors and anticancer drugs further reduces cancer cell viability. Anticancer drugs cisplatin (2.5 µM for W27 (=WZB-27) study or 5 µM for W115 (=WZB-115) study) or taxol (2.5 µM) was used to treat either H1299, A549 lung cancer cells or MCF7 breast cancer cells in the absence or presence of 10 µM of WZB-115 or 30 µM of WZB-27. Cell viability was measured by the MTT assay. The presence of the compounds significantly increased cancer cell death induced by either cisplatin or taxol. This experiment was repeated three times and the results were presented as means±standard deviations.

Inhibitors to Glucose Transport Sensitize and Synergize with Anticancer Drugs in Cancer Cell Killing The inhibitors disclosed herein target basal glucose transport while other anticancer drugs target pathways or processes not directly related to glucose transport. As a result, it was speculated that glucose transport inhibitors could potentiate or synergize with other anticancer drugs in their cancer activity when used together. This would be consistent with the recent finding that anti-GLUT1 antibody sensitizes and enhances the anticancer activity of anticancer drugs and our inhibitors should do the same. This has been shown to be the case in a compound study in H1299 or A549 cells lung cancer cells, which were treated with WZB-115 or (WZB-115+cisplatin) or (WZB-115+taxol) (FIG. 21). Addition of WZB-115 to either cisplatin or taxol led to significantly, more cancer cell killing than that induced by drugs alone. Similar results have been obtained for WZB-27 as well (FIG. 21).

This result suggests that glucose inhibitors such as WZB-115 or WZB-27 could significantly enhance the cytotoxic activity of anticancer drugs. This is accomplished by the compound's independent anticancer activity or the sensitizing activity of the compound to anticancer drugs or both. Further mechanistic study should be able to determine the real mechanism(s). This result, similar to what others found in their glucose transport inhibitor studies, strongly suggests that these compounds can be used alone to inhibit cancer growth or used together with other anticancer drugs to further increase the anticancer efficacy of the drugs. This also suggests that we may not have to use these inhibitors at very high concentrations as long as they are co-administered along with other anticancer drugs.

Figure 22A:
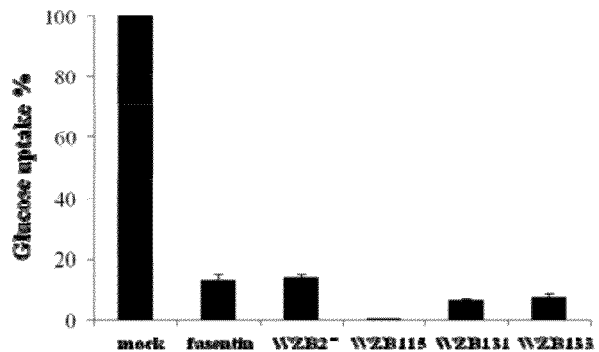
FIG. 22 shows a comparison study between in house compound inhibitors with fasentin in glucose uptake inhibition and cell viability in cancer cells. Known basal glucose compound fasentin and compound inhibitors generated in house were compared side by side in both glucose uptake assay and cell viability (MTT) assay. Glucose uptake or cell viability of mock treated samples was arbitrarily assigned a value of 100%. A. Glucose uptake assay in H1299 cancer cells. Concentration for all compounds was 30 µM. B. Cell viability assays in three different cancer cell lines. Concentration for all compounds was 60 µM.

Inhibitors are More Potent than Known Inhibitor Fasentin in Both Glucose Uptake Inhibition and in Reducing Cancer Viability Fasentin is a published inhibitor of basal glucose transport and known GLUT1 inhibitor. A comparison of reported inhibitors with fasentin was completed to determine if the compounds of interest exhibited similar biological activities to fasentin. It has been found that, similar to fasentin, our inhibitors induce reduction of glucose uptake. Some compounds such as WZB-115, 131, and 133 demonstrated stronger inhibition than fasentin in cancer cells (FIG. 22A). In addition, addition of these compounds (WZB-131 and 133) to different cancer cell lines resulted in more cancer cell death than fasentin at the same concentration (FIG. 22B).

These results demonstrated that (a) these compounds exhibit biological activities similar to fasentin, they are true inhibitors of basal glucose transport like fasentin, (b) they are more potent than fasentin in both activities tested. All these results indicate that these compounds are fasentin-like and are inhibitors of glucose transport but they possess more potent anticancer activities. As a result, they can be used in studies of glucose transport, glycolysis, and apoptosis of cancer cells as potentially superior inhibitors than fasentin.

Anticancer Activity Screening of Compound WZB-115 in 59 Cancer Cell Lines Done by NCI In order to further evaluate the lead compound WZB-115, the compound was sent to the National Cancer Institute (NCI) for screening its anticancer activities in a total of 59 cancer cell lines (FIG. 23). The screening results indicate that, (a) among 59 cancer cell lines and at 10 µM, the compound reduced the growth rates of 51 cell lines by more than 10% (<90% of the growth rates of the controls). (b) The compound reduced the growth rates of 21 cancer cell lines by more than 50% (or 35.6% of the 59 lines tested, FIG. 23). This result suggests that, in these 21 lines, the $IC_{50}$ of WZB-115 is lower than 10 µM. (c) The compound shows anticancer activities in all cancer types although it may be more effective in certain cancer types than others. (d) Large variations in activities are observed among cancer cell lines both within a single cancer type or among different cancer types. As a result, this compound is less likely to be very cytotoxic to normal cells than those compounds that are equally cytotoxic to all cancer cell lines. This is also consistent to our observation in animal injection tests (FIG. 20). Because of these promising results, the compound is recommended by NCI for a second round of screening using 5 different concentrations to determine its $IC_{50}$s in all these different cancer cell lines.

Figure 18C:
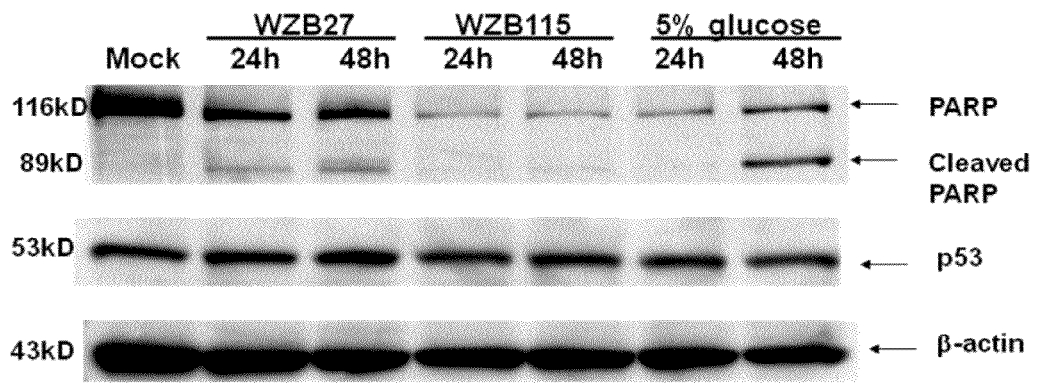

In summary, the preliminary results indicate that these compounds are inhibitors of basal glucose transport in all cancer cell lines tested (Table 3 and FIG. 19). The compound treatment led to apoptosis that is p53-independent and caspase 3-dependent (FIG. 18). The compound treatment caused significantly more cell death in cancer cells than in their normal cell counterparts (Table 4). Their preferential cancer cell killing also indicates that these cancer cell lines are more sensitive to the compound treatment than their normal cell counterparts, strongly suggesting these compounds are significantly more toxic to cancer cells to normal cells. They only cause mild and temporary hyperglycemia in animals (FIG. 20) without other noticeable side effects. Furthermore, they potentiate and synergize with existing anticancer drugs (FIG. 21). The addition of the compounds led to phenotypic changes in cancer cells as induced by glucose deprivation (FIG. 18C). These compounds form a novel group of molecular tool and anticancer agents since they inhibit a new target, basal glucose transport. Fasentin and these compounds can be used for studying how glucose deprivation affects glycolysis and how changes in glycolysis affect other changes such as apoptosis.

Initial Animal Efficacy and Safety Study

The ability of compounds WZB-27 and WZB-115 to inhibit/reverse tumor growth in nude mice, as well as the clinical safety of the compounds will be determined. Compounds will be use to treat nude mice (Jackson Labs) with cancer grown from H1299 (lung cancer) and MCF-7 (breast cancer) cells. Five millions of cancer cells will be injected subcutaneously into the flank of each of 30 nude mice. The tumor cell-injected mice will be randomly split into three groups: ten for compound treatment, ten for drug (e.g. WZB-117) treatment (positive controls) and another ten receive vehicle (solvent) treatment. After tumors become palpable and visible (~5-7 days), the compound treatment will begin. A molar concentration of $IC_{50}$ will be chosen for each compound for the treatment. Compounds will be dissolved in DMSO or other compatible solvent right before injection. The solvent that dissolve the compounds will be used in the solvent treatment group. The animal study design is shown in Table 5.

TABLE 5

Design of initial animal study
(same study in both H1299 and MCF-7 tumor mice)

| Group/group function | N= | Treatment | Treatment duration | Parameters measured |
|---|---|---|---|---|
| 1. Negative control | 10 | Solvent, once a day | 4-5 wks | Tumor size, blood glucose, body weight |
| 2. Fasentin, positive control | 10 | Fasentin at $IC_{50}$*, as above | 4-5 wks | Same as above |
| 3. WZB-27 | 10 | WZB-27 at $IC_{50}$, as above | 4-5 wks | Same as above |
| 4. WZB-115 | 10 | WZB-115 at $IC_{50}$, as above | 4-5 wks | Same as above |

*$IC_{50}$ is determined from cancer cell viability study. $IC_{50}$ is different for each cancer cell line The IP injection of compounds will be performed once every day for 4-5 weeks depending upon tumor growth rates. Tumor sizes will be measured with calipers twice a week and recorded as $LW^2/2$=volume in $mm^3$ (L=length, W=width) and compared to those of tumors on solvent injected control mice. Body weight of the mice is measured once a week. Body weight is an indication of the health status of the treated mice. In order to determine how compound treatment affects blood glucose levels, blood glucose will also be measured immediately prior to the compound injection and 1, 2, and 4 hr after the injection and the blood glucose levels will be compared to those of the solvent injected mice. Once the glucose levels are measured, a decision will be made on if the blood glucose monitoring should be continued or can be terminated. The compound treatment lasts 3-5 weeks until the tumors grown in the solvent treated mice become large (>5% but <10% of the body weight, or ≥20 mm in the largest length measurement). The animal study will be carried out and terminated in accordance to the rules and regulations of NIH and of our university IACUC. Tumor-bearing mice will be euthanized at the end of the study, according to the related rules by NIH and DOA. The average size of the tumors in the treated groups will be compared to the untreated control group to show treatment efficacy and statistical differences. The better of the two compounds, based on combined consideration of anticancer efficacy and toxicity to mice (primarily its effect on blood glucose levels and body weight changes and/or other unexpected side effects), will be chosen for the dose response animal study described below.

Determination of Dose Response of Compound Treatment in Animals

Although anticancer efficacy may be shown in the initial animal study, the dose used in the study is definitely not optimal for each compound. In order to further determine the better dose, at which anticancer efficacy is maximized but the side effects are still tolerable, a dose response animal study will be conducted (Table 6).

TABLE 6

Determination of compound dose response

| Group/group function | N | Treatment | Treatment duration | Parameter measured |
|---|---|---|---|---|
| 1. Negative control | 10 | Solvent | 4-5 wks | Tumor size, blood glucose levels, body weight |
| 2. Fasentin low dose | 10 | Fasentin at $IC_{50}$ | 4-5 wks | Same as above |
| 3. Fasentin high dose | 10 | Fasentin at $3 \times IC_{50}$ | 4-5 wks | Same as above |
| 4. WZB-27 low dose | 10 | WZB-27 at $IC_{50}$ | 4-5 wks | Same as above |
| 5. WZB-27 high dose | 10 | WZB-27 at $3 \times IC_{50}$ | 4-5 wks | Same as above |
| 6. WZB-115 low dose | 10 | WZB-115 at $IC_{50}$ | 4-5 wks | Same as above |
| 7. WZB-115 high dose | 10 | WZB-115 at $3 \times IC_{50}$ | 4-5 wks | Same as above |

For compounds Fasentin, WZB-27 and WZB-115, two doses will be tried: $IC_{50}$ and $3 \times IC_{50}$. After this experiment, The dose response for these compounds will be known. We will also know which compound performs the best in terms of reduction of tumor size and side effects, and if the $3 \times IC_{50}$ dose can be well tolerated by nude mice or not. This study will be done using both H1299 and MCF-7 cancer cell models. From the results of this experiment, one of the two compounds, WZB-27 or WZB-115 designated as compound to be determined (Compound$_{tbd}$), and its better dose, will be selected for the next round of animal study.

Does Inhibitor of Basal Glucose Transport Potentiate and Synergize with Cancer Drugs in the Anticancer Activity Synergistic and potentiating effects were found between fasentin and anticancer drugs (Ref). In our preliminary studies, the similar effects were also observed (FIG. 21). However, it is unclear if such synergistic effects can also be found in animals. To that end, a large animal study will be conducted (Table 7).

TABLE 7

Design of animal study for determination of synergy between inhibitors and cancer drugs

| Group/group function | N | Treatment | Treatment duration | Parameter measured |
|---|---|---|---|---|
| 1. negative control | 10 | Solvent | 4-5 wks | Tumor size, blood glucose levels, body weight |
| 2. Fasentin | 10 | Fasentin at $C_{tbd}$* | 4-5 wks | Same as above |
| 3. Compound | 10 | Compound$_{tbd}$** at $C_{tbd}$ | 4-5 wks | Same as above |
| 4. Cisplatin | 10 | Cisplatin at $IC_{70}$ | 4-5 wks | Same as above |
| 5. Taxol | 10 | Taxol at $IC_{70}$ | 4-5 wks | Same as above |
| 6. Fasentin + cisplatin | 10 | Fasentin at $C_{tbd}$ + Cisplatin at $IC_{70}$ | 4-5 wks | Same as above |
| 7. Compound + cisplatin | 10 | Compound at $C_{tbd}$ + Cisplatin at $IC_{70}$ | 4-5 wks | Same as above |
| 8. Fasentin + taxol | 10 | Fasentin at $C_{tbd}$ + taxol at $IC_{70}$ | 4-5 wks | Same as above |
| 9. Compound + taxol | 10 | Compound at $C_{tbd}$ + taxol at $IC_{70}$ | 4-5 wks | Same as above |

*$C_{tbd}$ = concentration to be determined as described herein;
**Compound$_{tbd}$ = compound to be determined as described herein.

How Compound Inhibitor Treatment Affects Levels of Proteins/Enzymes Involved in Glycolysis, Cell Growth Signal Transduction, and Apoptosis To better understand how inhibitors of basal glucose transport inhibit tumor growth in vivo, tumors treated with or without compound inhibitors will be removed from tumor mice euthanized at the end of animal studies described above and are immediately frozen by liquid nitrogen for late analysis. For tumor analysis, proteins will be extracted from removed tumors and quantified. Protein samples will then be subjected to PAGE followed by western blotting analysis using antibodies specifically against p53, Akt, PKM2, hexokinase, and caspases. The intensities of these proteins from compound treated samples will be compared to those of tumor samples that are treated by solvent (vehicle). Protein β-actin and/or GAPDH will be used as protein loading controls for normalizing protein bands. These western blots will enable us to gain the protein expression changes in the compound treated tumors, which can potentially facilitate the final elucidation of anticancer mechanism(s) of these compound inhibitors in vivo.

Synthesis of Generation 2 Compounds

Disclosed herein is the design and synthesis of a second generation of basal glucose transporters based upon alteration of the linkage between the parent aromatic ring and the phenolic aromatic substituents. Previously, a small library of polyphenolic esters were synthesized and evaluated. The generation 1 compounds were shown to inhibit basal glucose transport in H1299 lung cancer cells, and also inhibited cancer cell growth in H1299 cells. WZB-115 was selected as the lead compound from this library. Unfortunately, WZB-115 failed long-term stability assays in animal models. The degradation rate of WZB-115 and WZB-117 in human serum was established, both compounds degraded completely after 48 hours. Thus, more stable analogs need to be designed and synthesized.

Figure 37:
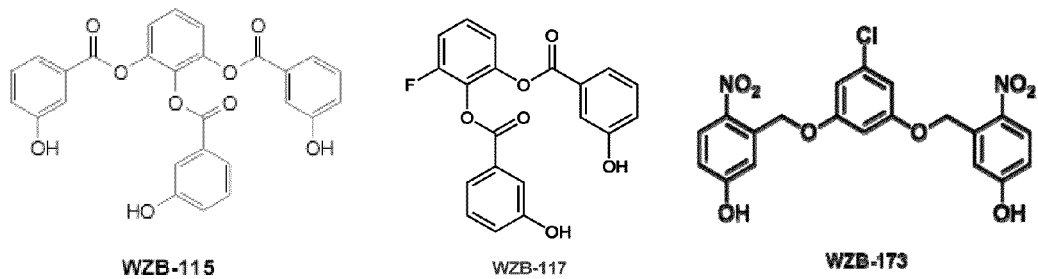
FIG. 37 shows the structures of several novel glucose transport inhibitors WZB-115, 117, and 173. Compound 117 is an analog of 115 while 173 is an ether-bond analog. Compounds WZB-117 and WBZ-173 are derived from compound WZB-115, which is a polyphenolic model compound used in our previous cancer studies. WZB-115 was derived from a natural anticancer and antidiabetic compound called penta-galloyl-glucose (PGG). WZB-117 and WZB-173 are very similar structurally to 115 but are both structurally simplified and functionally optimized compared to WZB-115. As a result, WZB-117 and WZB-173 are more potent in their anticancer activities than WZB-115 and are also structurally more stable than 115 in solution and cell culture media.

Disclosed herein are the structures of novel glucose transport inhibitors WZB-115, WZB-117, and WZB-173 (FIG. 37). Compound WZB-117 is an analog of WZB-115 while WZB-173 is an ether-bond analog. Compounds WZB-117 and WBZ-173 (FIG. 37) are derived from compounds WZB-115, which is a polyphenolic model compound used in our generation 1 cancer studies. WZB-115 was derived from a natural anticancer and antidiabetic compound called pentagalloyl-glucose (PGG). WZB-117 and WZB-173 are very similar structurally to WZB-115 but are both structurally simplified and functionally optimized compared to WZB-115. As a result, WZB-117 and WZB-173 are more potent in their anticancer activities than WZB-115 and are also structurally more stable than WZB-115 in solution and cell culture media.

Synthesis of Multi-Phenolic Ether Derivatives 3-(Methoxymethoxy)benzyl chloride, the precursor for predesigned polyphenolic derivatives, was synthesized in high yield over four steps. Commercially available 3-hydroxybenzoic acid was treated with sulfuric acid in methanol to elicit a Fischer esterification. Protection of the phenol was accomplished by treatment of the phenolate with MOMCl. Reduction of the ester followed by a modified Appel reaction afforded the desired compound in greater than 65% over four steps (Scheme 2).

Scheme 2. Synthesis of 3-(methoxymethoxy)benzyl chloride

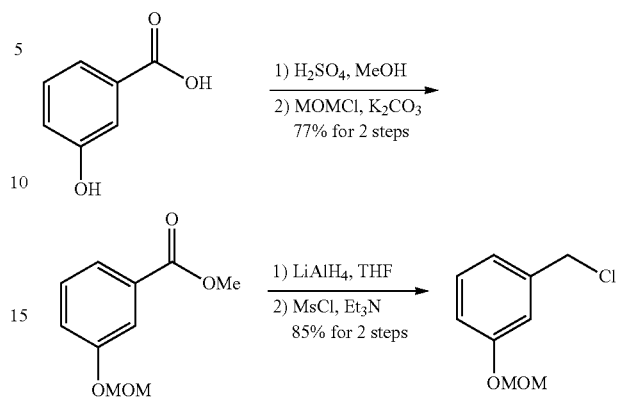

The synthesis of the polyphenolic ethers, amines, and amides were accomplished via $S_N2$-type reactions or nucleophilic acyl substitution reactions (Scheme 3 and 4). Synthesis of the second generation basal glucose transport inhibitors could be accomplished by one who is skilled in the art without further description or disclosure of further experimental detail.

Scheme 3. Synthesis of polyphenolic ether derivatives

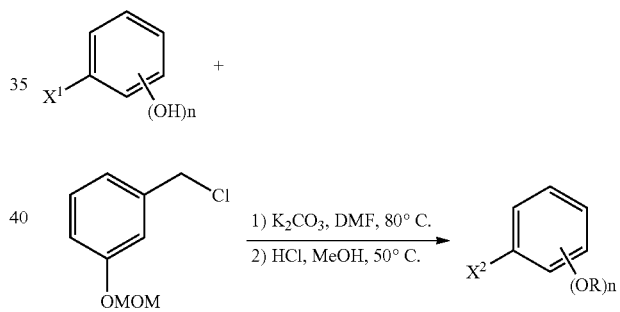

| Compd # | $X^1$ | (OH)n | $X^2$ | (OR)n | Yield[a] |
|---|---|---|---|---|---|
| WZB-131 | OH | 1,2-(OH)$_2$ | 3-OH—C$_6$H$_4$CH$_2$O | 1,2-(3-OH—C$_6$H$_4$CH$_2$O)$_2$ | 54 |
| WZB-132 | OMe | 1,2-(OH)$_2$ | OMe | 1,2-(3-OH—C$_6$H$_4$CH$_2$O)$_2$ | 70 |
| WZB-133 | Cl | 3,4-(OH)$_2$ | Cl | 3,4-(3-OH—C$_6$H$_4$CH$_2$O)$_2$ | 65 |
| WZB-134 | F | 1,2-(OH)$_2$ | F | 1,2-(3-OH—C$_6$H$_4$CH$_2$O)$_2$ | 46 |
| WZB-137 | Cl | 1,3-(OH)$_2$ | Cl | 1,3-(3-OH—C$_6$H$_4$CH$_2$O)$_2$ | 57 |
| WZB-141 | Cl | 2,4-(OH)$_2$ | Cl | 2,4-(3-OH—C$_6$H$_4$CH$_2$O)$_2$ | 72 |

[a]yield is based on two steps

SCHEME 4

Synthesis of polyphenolic amine and amide derivatives

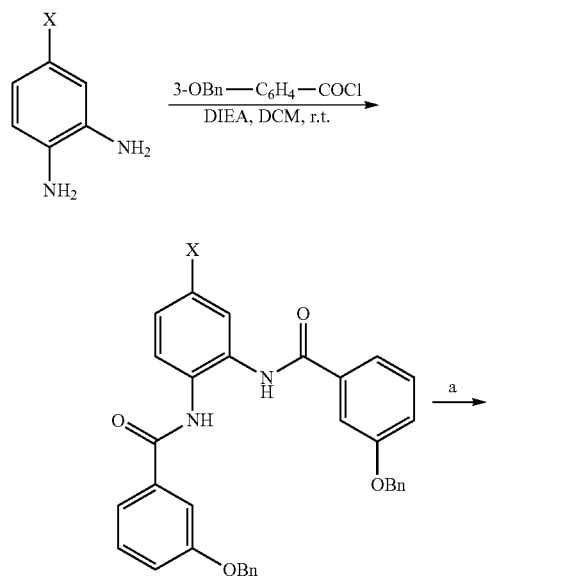

| Compd # | X | R² | a | Y | Yield |
|---|---|---|---|---|---|
| WZB-125 | Cl | H | H₂, Pd/C | CO | 83 |
| WZB-138 | Cl | H | 1) H₂, Pd/C; 2) LAH | CH₂ | 75 |
| WZB-142 | Cl | Me | 1) MeI, NaH; 2) H₂, Pd/C | CO | 71 |
| WZB-145 | Cl | Me | 1) MeI, NaH; 2) H₂, Pd/C; 3) LAH | CH₂ | 66 |
| WZB-124 | F | H | H₂, Pd/C | CO | 86 |
| WZB-139 | F | H | 1) H₂, Pd/C; 2) LAH | CH₂ | 78 |
| WZB-143 | F | Me | 1) MeI, NaH; 2) H₂, Pd/C | CO | 70 |
| WZB-144 | F | Me | 1) MeI, NaH; 2) H₂, Pd/C; 3) LAH | CH₂ | 65 |

The separate yield is based on the step(s) shown in reaction conditions above

Evaluation of Generation 2 Compounds

Compounds WZB-134, WZB-141 and WZB-144 inhibited basal glucose transport in H1299 cells by 92.5±2.2%, 96.5±0.5%, and 78.2±1.4%, respectively (Table 12), as measured by a standard glucose uptake assay compared to non-compound treated cells controls (considered as 0% inhibition). Tested in an MTT cell proliferation assay in H1299 cells, their inhibitory activities on cancer cell growth were found to be 10.6±2.0%, 39.5±1.8%, and 14.5±7.6%, respectively (non-compound treated cell controls were considered as 0% inhibition).

TABLE 12

Polyphenolic ethers, amine, and amide induced inhibitory activities in basal glucose transport and cell growth in H1299 lung cancer cells

| Compound # | Glucose transport inhibition[a] (%) | Cell growth inhibition[b] (%) |
|---|---|---|
| WZB-124 | 89.7 ± 2.5[b] | 5.7 ± 2.1 |
| WZB-125 | 83.7 ± 0.7 | 5.9 ± 1.4 |
| WZB-131 | 95.0 ± 1.6 | 12.9 ± 2.6 |
| WZB-132 | 60.0 ± 7.7 | 6.0 ± 2.2 |
| WZB-133 | 91.2 ± 0.8 | 14.3 ± 2.7 |
| WZB-134 | 92.6 ± 2.2 | 10.6 ± 2.0 |
| WZB-137 | 86.2 ± 1.6 | — |
| WZB-138 | 52.2 ± 9.7 | — |
| WZB-139 | 39.2 ± 0.8 | — |
| WZB-141 | 96.5 ± 0.5 | 39.5 ± 1.8 |
| WZB-142 | 82.7 ± 6.8 | 14.2 ± 9.0 |
| WZB-143 | 85.7 ± 3.6 | 31.1 ± 7.9 |
| WZB-144 | 78.2 ± 1.4 | 14.5 ± 7.6 |
| WZB-145 | 73.2 ± 3.8 | 38.2 ± 6.6 |

[a]Untreated cells served as negative controls (0% inhibition).
[b]Data were presented as a mean ± standard deviation.

Figure 30:
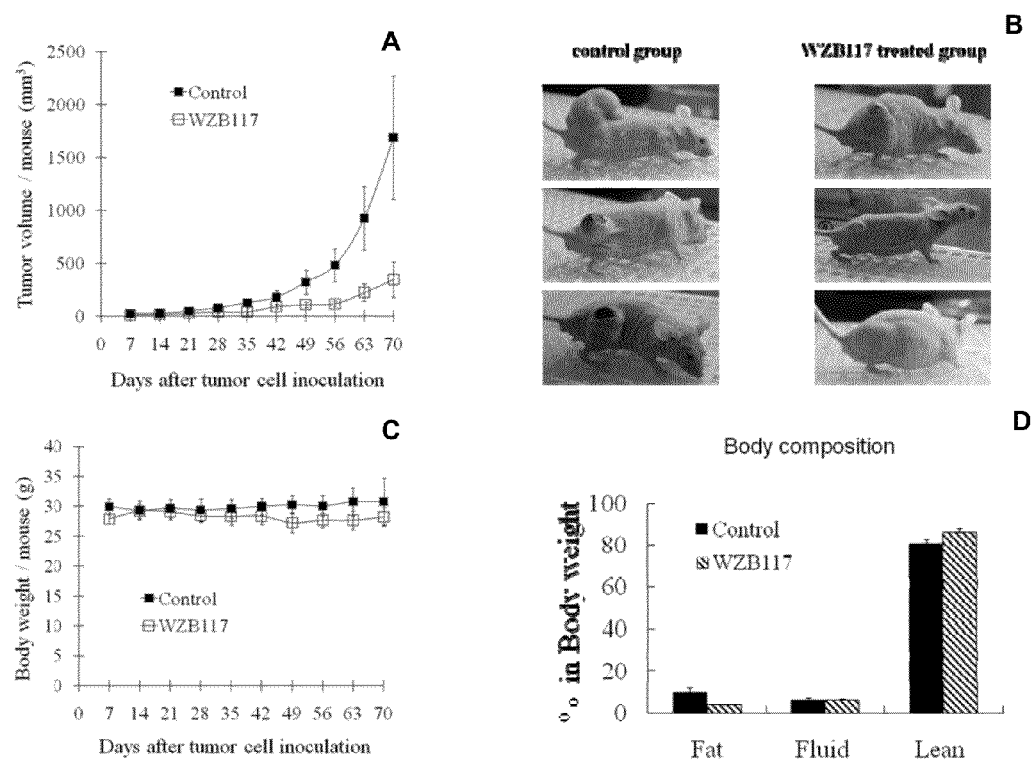
FIG. 30 shows a comparison of tumor sizes of human lung cancer A549 grafted on nude mice. Photos were taken 8 weeks after the treatment. Male NU/J, nude mice (7-8 weeks old) were used and purchased from The Jackson Laboratory (Bar Harbor, Me.) and provided the Irradiated Teklad Global 19% protein rodent diet from Harlan Laboratories (Indianapolis, Ind.). To determine the in vivo efficacy of compound WZB-117 against human NSCLC tumor xenograft growth, exponentially growing A549 cells were harvested and re-suspended in PBS to achieve a final concentration of $5 \times 10^6$ cells in 25 μl suspension. Each mouse was injected subcutaneously in the right flank with 25 μl cell suspension. At this time, mice were randomly divided into two groups: control group (n=10) treated with PBS/DMSO (1:1, v/v), and WZB-117 treatment group (n=10), treated with WZB-117 (15 mg/kg). Compound WZB-117 was dissolved in PBS/DMSO (1:1, v/v). Mice were given intraperitoneal injection with either PBS/DMSO mixture or compound WZB-117 (15 mg/kg) daily since the day of tumor cell inoculation. A. Tumor growth curve. Animal tumor study indicated that, by daily injection of WZB-117 at the dose of 10 mg/kg body weight, the tumor size of the compound treated tumors were on average approximately 75% smaller than that of the mock treated mice. B. Mouse tumor photos. Tumor-bearing mice on the left were mock-treated while the mice on the right were treated with WZB-117. C. Mouse body weight measurements. D. Body weight compositions of the WZB-117 treated mice compared to those of mock-treated mice.

Antitumor Study. Anticancer Activity of WZB-117 Against Human Lung Cancer A549 Grafted on Nude Mice This animal tumor study indicated that, by daily injection of WZB-117, the tumor size of the compound treated tumors were on average approximately 75% smaller than that of the mock treated group although the variation of the tumor sizes were quite large (FIG. 30A). This result was qualitatively similar to that of a tumor study using antiglycolytics. Noteworthy, two of the ten compound treated tumors disappeared during the treatment and they never grew back even at the end of the study (FIG. 30B). Body weight measurement and analysis revealed that the mice treated with WZB-117 lost 2-3 grams of weight compared to the mock-treated mice with most of the weight loss in the fat tissue (Table 8). Blood counts and analysis showed that some key blood cells such as lymphocytes and platelets were significantly changed in the compound treated mice, but they were still in the normal ranges (Table 9). All these results indicate that the treatment of WZB-117 was effective in reducing tumor sizes and the treatment was relatively well tolerated by the mice. One of the concerns for using basal glucose transport inhibitors is that the inhibitor may cause hyperglycemia in the injected patient. It has been found that the injection of WZB-117 produced mild and temporary hyperglycemia that disappeared within a period of 2 hours after the compound administration, and it did not result in permanent hyperglycemia.

Anticancer Mechanism Study. Anticancer Compound WZB-117 Inhibition of Glut1

Figure 32:
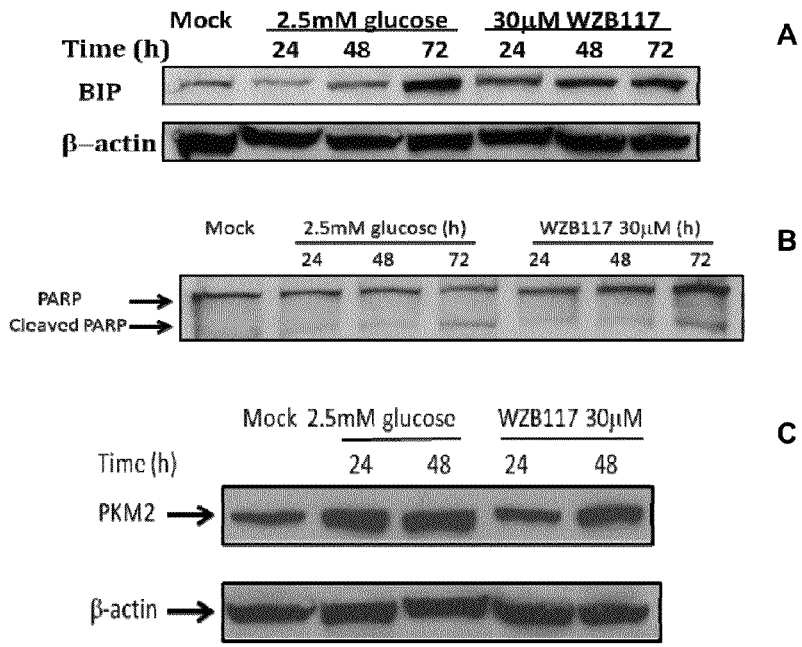
FIG. 32 shows WZB-117 treatment of cancer cells induce ER stress, apoptosis and change in glycolytic enzymes. A. WZB-117 treatment upregulates ER stress protein BiP in a similar way as glucose deprivation. B. WZB-117 treatment induces cleavage of PARP, suggesting the apoptosis induction mediated by p53. C. WZB-117 treatment upregulates the key glycolytic enzyme PKM2 in cancer cells in a similar manner as the glucose deprivation.
Figure 33:
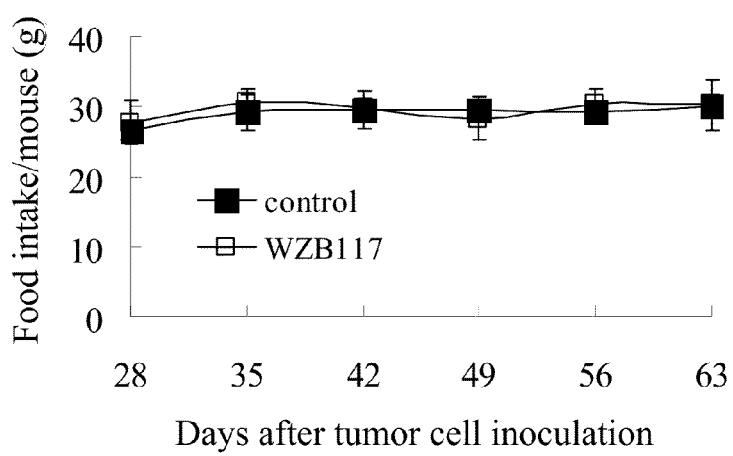
FIG. 33 shows food intake of mice treated with or without WZB-117. There was no change of food intake between the PBS/DMSO and the WZB-117 treated group during the study. Food intake of each group was measured every 7 days since tumor cell inoculation.
Figure 34:
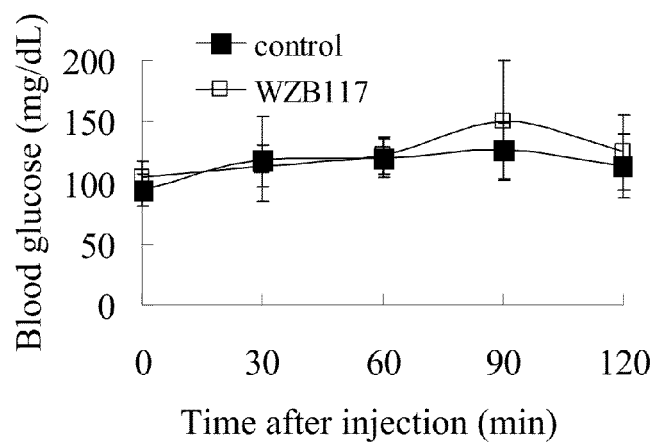
FIG. 34 shows blood glucose measurement of tumor-bearing nude mice treated with or without WZB-117. Blood glucose level of each mouse was measured by a blood glucose monitor, and it was measured right before the IP injection of WZB-117 (15 mg/kg) and every 30 minutes after injection. Food was available to mice during the measurement. Data was expressed in average±standard deviation. No significant difference in blood glucose levels was found between untreated and compound WZB-117 injection group immediately after the compound injection or during or after the animal study.

To demonstrate that inhibitors of glucose transport induce ER stress, 30 μM of inhibitor WZB-117 was used to treat A549 cells (with glucose deprivation being the control). The Western blot of the proteins isolated from the treated cells shows that glucose regulated protein-78 (GRP78, also called BiP), one of the key ER stress markers, was significantly upregulated at 48 and 72 hrs after the inhibitor treatment (FIG. 32), indicating that the inhibitor indeed induces ER stress in cancer cells. Glucose concentration in regular cell culture medium was 25 mM, and 2.5 mM (10% of the regular concentration) was used as the glucose deprivation control condition. The inhibitor also led to qualitatively similar results in BiP upregulation as glucose deprivation (FIG. 32).

Glucose deprivation induces upregulation of ER stress protein BiP. Lung cancer A459 cells were treated by either glucose deprivation or by inhibitor 117 for various times and then proteins of the cells were analyzed by using anti-BiP antibody. β-actin serves as a protein control (FIG. 32A).

Figure 31:
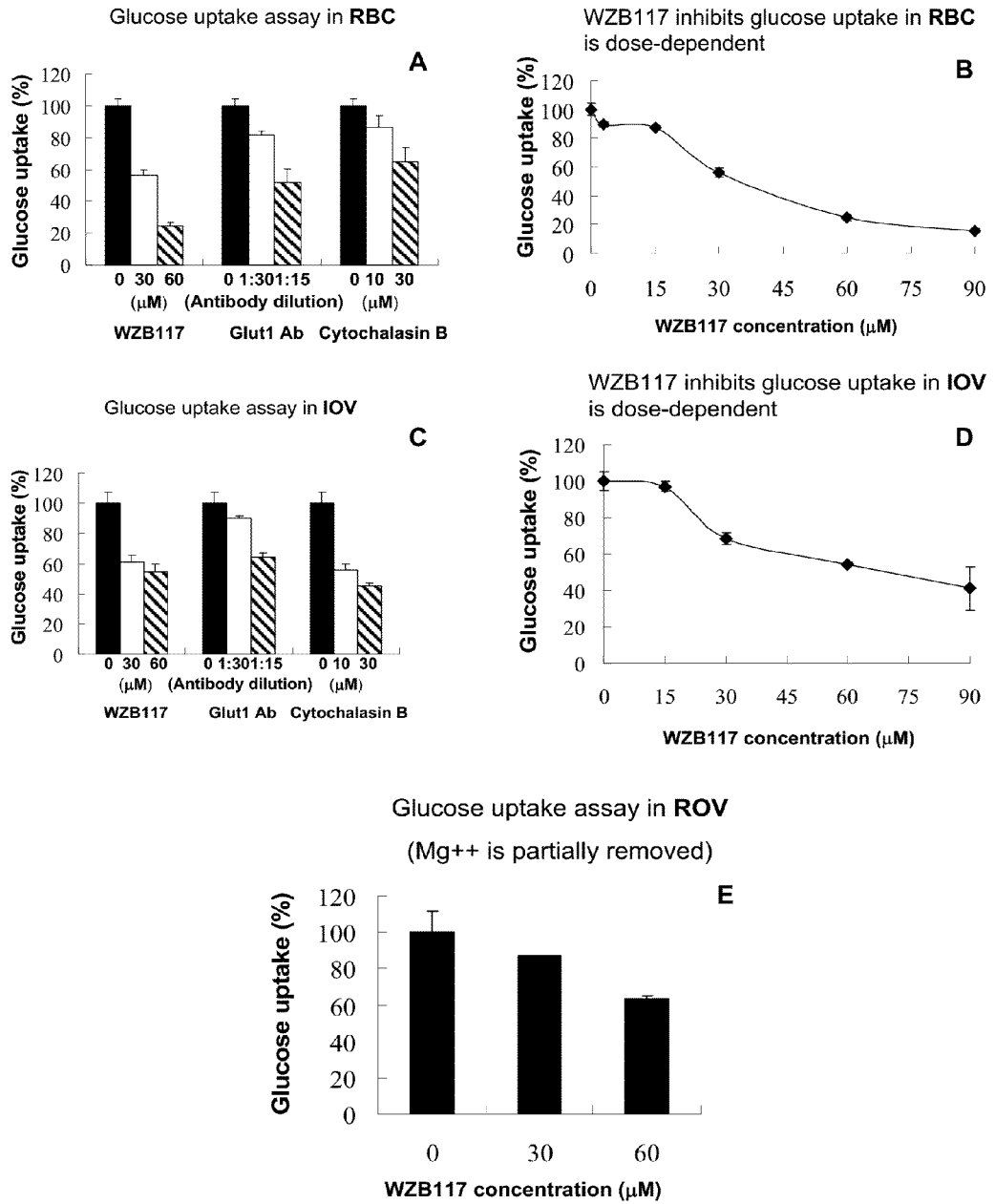
FIG. 31 shows WZB-117 inhibition of glucose transport by inhibiting Glut1. A. and B. WZB-117 inhibits glucose transport in red blood cells (RBC) in a dose-dependent fashion. C. and D. WZB-117 inhibits glucose transport in RBC derived "inside out" vesicles (IOV) in a dose-dependent fashion. E. WZB-117 inhibits glucose transport in RBC derived "right side out" (ROV) vesicles.

Previously, it was found that our anti-glucose transport compounds inhibited glucose transport in all the cancer cell lines tested. It was speculated that the target of these inhibitors is Glut1 since Glut1 is responsible for basal glucose transport in almost all cell types. In order to test this hypothesis, RBC was chosen as a cell model to study because RBC has been known to express only Glut1, not any other glucose transporters. The glucose uptake assays revealed that WZB-117 indeed inhibited the glucose transport in RBC (FIG. 31A), supporting the notion that WZB-117 inhibits glucose transport by inhibiting Glut1. To further eliminate other possibilities, the glucose uptake assays were repeated in RBC-derived vesicles, in which all the intracellular proteins and enzymes were removed and only membrane-bound and tightly associated proteins left. The assay result showed that WZB-117 continued to inhibit glucose transport in these vesicles, indicating that intracellular proteins are not needed for the inhibition and providing strong evidence that Glut1 is the target of the inhibition (FIG. 31C-E).

In order to determine the protein target of the inhibition of basal glucose transport by our compound, human red blood cells (RBC) were used. The selection of RBC was based on (1) Glut1 was hypothesized as the most probable target and RBC express Glut1 as their only glucose transporter, (2) RBC are an established model for and have been frequently used in studying glucose transport.

It was found that, in addition its inhibition of basal glucose transport in all the cancer cell lines, our compound inhibits glucose transport in RBC (FIG. 31), indicative that the compound acts on Glut1 for the inhibition and supportive that Glut1 is the target of the inhibition.

To further the target identification, vesicles were prepared from the ruptured RBC called ghosts. These small sealed vesicles were formed from plasma membrane of RBC under different salt conditions and they demonstrated two distinct orientations: inside out or right side out. The right side out vesicles (ROV) exhibit the same membrane orientation as RBC while inside out vesicles (IOV) show opposite membrane orientation as the membrane of RBC. However, since Glut1 is a glucose uniporter and can transport glucose in both directions, Glut1 located on either IOV or ROV should be able to transport glucose down the glucose gradient. As expected, the glucose uptake assays showed that our compound could inhibit Glut1-mediated glucose transport in both IOV and ROV (FIG. 31C-E), providing strong supporting evidence for our hypothesis that Glut1 is the target of the action of the inhibition by our compound. The reason that the compound showed more inhibition in IOV than in ROV was due to the presence of $Mg^{++}$ in the ROV preparation. $Mg^{++}$ is not previously known for its interference with Glut1 function.

The observation that the compound worked on both ROV and IOV also suggests that the compound may interact with the excellular portion of Glut1. The extracellular portion of Glut1 is located intracelluarly (intravesicularlly) in IOV. The compound is likely to cross the vesicle membrane and interact with the intravesicular part of Glut1, inhibiting the glucose transport down the gradient. This is consistent with the chemical properties of the compound, which indicates the hydrophobicity of the compound is likely to allow the compound to cross the vesicle membrane and function intravesicularlly in artificial vesicles or intracellularly in intact cells.

Figure 35:
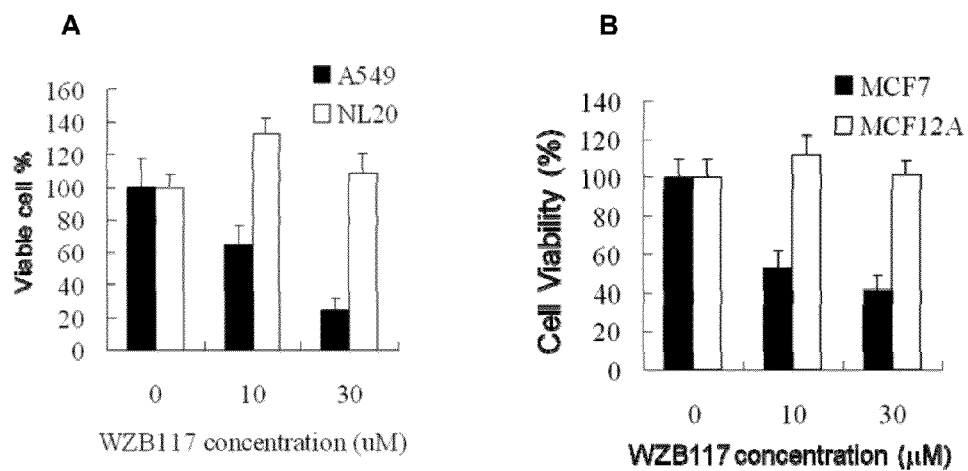
FIG. 35 shows that compound WZB-117 kills significantly more cancer cells than non-cancerous cells. A. A549 lung cancer and B. MCF7 breast cancer cells were treated with or without WZB-117 for 48 hr, and then measured for their respective viability rates with the MTT assays. Mock-treated cells served as controls (100% viability) for comparison. Noncancerous NL20 and MCF12A cells were treated the same way for comparison.
Figure 36:
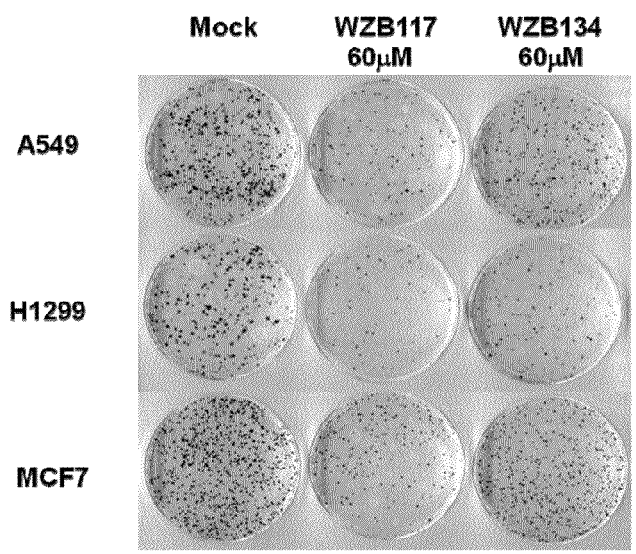
FIG. 36 shows the anticancer activity of WZB-117 as demonstrated by clonogenic assays. Three cancer cell lines A549, H1299 (lung cancers) and MCF7 (breast cancer) grown in culture dishes were treated with WZB-117 or a weaker inhibitor WZB-134 or no compound (mock) for 48 hrs. Then the treated cells were allowed to grow back in compound-free normal cell culture medium for 2 weeks and then stained with crustal violet and counted for number of survived clones. The fewer and smaller the stained spots (clones), the higher the inhibition.

Generation 2 Compounds Induce Cell Death Preferentially in Cancer Cells Opposed to their Normal Counterparts Cancer cells depend on glucose as their energy source and basal glucose transport inhibition has been proposed as an anti-cancer strategy. In order for these compounds to be effective anti-cancer agents, they must be able to kill more cancer cells than normal cells. Compound WZB117 kills significantly more cancer cells than non-cancerous cells. A549 lung cancer and MCF7 breast cancer cells (FIG. 35) were treated with or without WZB117 for 48 hr, and then measured for their respective viability rates with the MTT assays. Mock-treated cells served as controls (100% viability) for comparison. Noncancerous NL20 and MCF12A cells were treated the same way for comparison. These results suggest that compound WZB-117 has potential to serve as an anti-cancer agent. FIG. 36 suggests that compound WZB-117 exhibits significantly more cytotoxicities towards cancer cells than towards non-cancerous (i.e., "normal") cells.

EXAMPLES

General Experimental Protocols

Experimental Protocols. Chemical and Synthetic.

General Scheme for Identifying Improved Basal Glucose Transport Inhibitors

Figure 24:
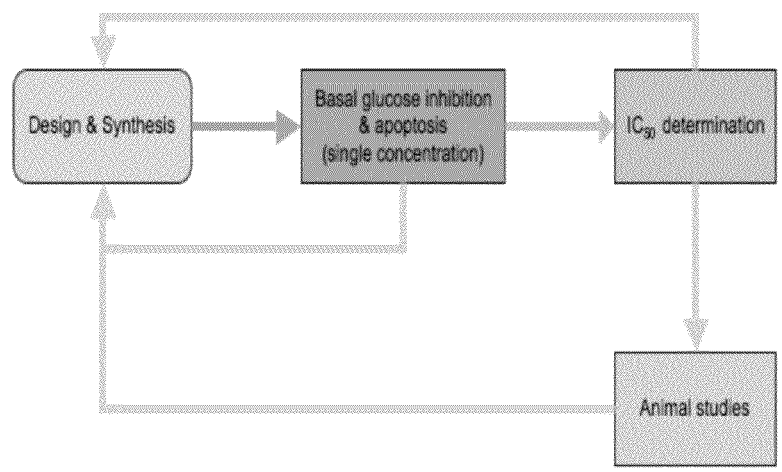
FIG. 24 shows a general scheme for identifying improved basal glucose transport inhibitors.

Identification of improved small molecule anticancer agents that act as inhibitors of basal glucose transport is outlined in FIG. 24. Upon design and synthesis of potential basal glucose uptake inhibitors, the compounds will be examined in both a basal glucose inhibition assay and an apoptosis assay at a single concentration. Compounds that exceed a baseline value will be further examined and $IC_{50}$ values determined. The results of these assays will be used to guide the design of additional agents.

Pharmacological Evaluation of Inhibitors of Basal Glucose Transport

All compounds will be evaluated in a series of pharmacological assays designed to ascertain the ability of the compounds to both inhibit basal glucose uptake and kill cancer cells. Initial evaluation of compounds will focus upon elimination of compounds that are unstable in serum or lack appropriate activity.

Compounds will be assayed for their ability to inhibit basal glucose uptake. All compounds will be tested at a concentration of 10 μM first and their inhibitory activity on basal glucose transport will be measured and compared to that of WZB-27. Cell lines H1299 (lung cancer) and MCF-7 (breast cancer) grown in 24-well cell culture plates will be treated with or without the compounds for 10 min before the glucose uptake assay. Cellular glucose uptake will be measured by incubating cells in glucose-free RPMI 1640 buffer with 0.2 Ci/mL [$^3$H]2-deoxyglucose (specific activity, 40 Ci/mmol) for 30 min in the absence and presence of compounds. After removal of the buffer, the cells are washed with ice-cold PBS, cells will be lysed and transferred to scintillation vials and the radioactivity in the cell lysates will be quantified by liquid scintillation counting. Only those compounds that show comparable or stronger inhibitory activity than that of WZB-27 will be selected for the next assay. Known glucose transport inhibitors Fasentin ($IC_{50} \geq 50$ μM) and apigenin ($IC_{50} \geq 60$ μM) will be used as positive controls for comparison.

Initial assays will also determine the ability of these compounds to kill cancer cells and to leave normal cells untouched. Those compounds that pass the criteria of the glucose uptake assay for inhibitory activity of basal glucose transport described above will be tested in a subsequent cell killing (viability) assay. Compounds will be individually added to H1299 (and its normal cell counterpart NL20) and MCF-7 (and its normal cell counterpart MCF-12A) cells grown in 24-well plates at a concentration of 30 µM and incubated at 37° C. in a cell culture incubator for 48 hrs. After incubation, the cells in each well will be measured for its viability by an MTT assay.

Further investigation of compounds will be conducted pending that the compounds of interest inhibit glucose uptake greater than WZB-27, cause a decrease in cancer cell viability of at least 50%, and cause no more than a 20% decrease in normal cell viability. Further assays for compounds meeting the minimal initial screening requirements will include determination of an $IC_{50}$ for glucose uptake inhibition and an $EC_{50}$ for cell killing by including multiple concentration assay points such as 0.1, 0.3, 1, 3, 10, 30, and 50 µM.

Synthesis of More Potent and Selective Inhibitors of Basal Glucose Transport

The general goal is to generate more potent and selective inhibitors of glucose uptake. These compounds should have a lower molecular weight, improved water solubility, and good stability. All compounds will be prepared on a 15-20 mg scale and will be purified to >90% purity as analyzed by HPLC, LCMS and $^1H/^{13}C$ NMR. Each compound will be stored in a bar-coded vial as a 50 mM solution in DMSO. This scale will provide ample material for initial screens, as well as follow-up screening if necessary.

Figure 25:
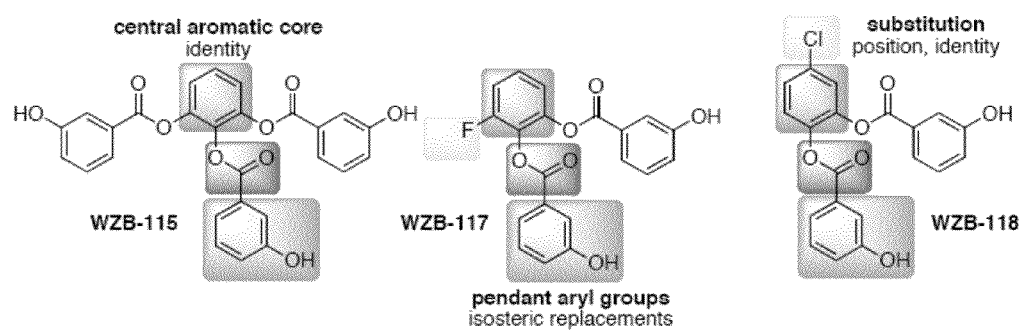
FIG. 25 shows several lead compounds and areas for structural modification.

As shown in FIG. 25, lead compounds (WZB-115, WZB-117, and WZB-118) have four distinct molecular areas of interest, the central aromatic core, the pendant aryl groups, the linker, and the substitution on the central aromatic core. Each of these four areas will be examined in order to determine its significance and to develop more potent analogs. Initial focus will be placed upon the development of non-hydrolyzable linkers that retain the activity of the parent ester. This will be key for carrying out in vivo efficacy studies. Concurrently, the replacement of the pendant phenol with bioisosteric replacements will be examined in an effort to improve bioavailability. The substitution and identity of the central aromatic core will also be examined in an effort to improve potency.

Linker Modifications

Figure 26:
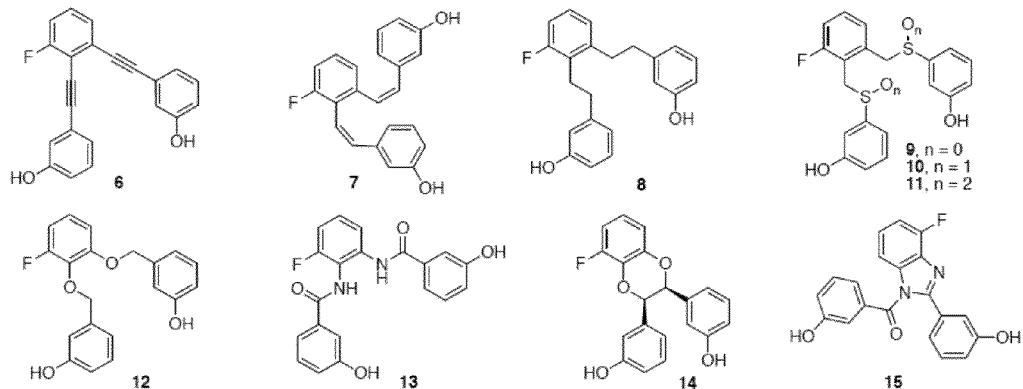
FIG. 26 shows an initial set of tether analogs.
Figure 27:
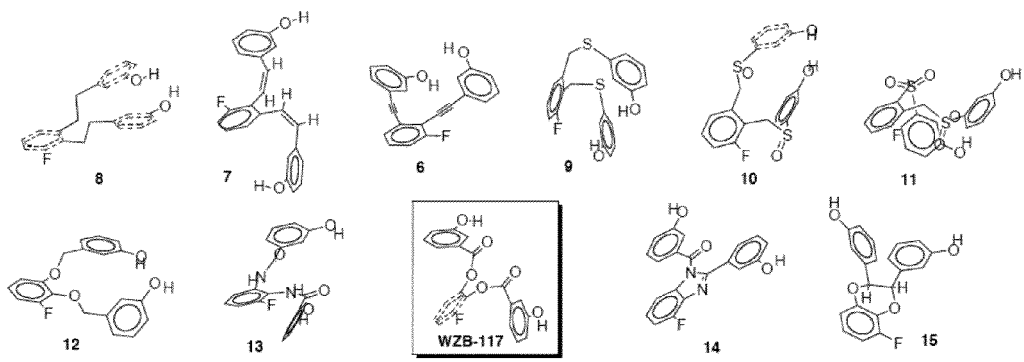
FIG. 27 shows energy-minimized structures of proposed linkage analogs.
Figure 28:
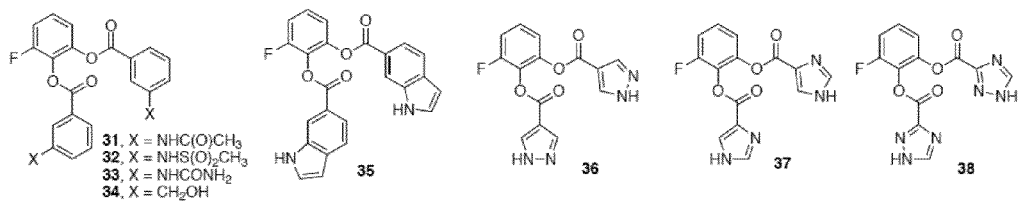
FIG. 28 shows biosteric analogs of the phenol group.

Contemplated herein are a series of analogs (FIG. 26) in which the linker between the central aromatic core and the pendant aromatic rings has been modified. These investigations into modifications of the linker are focused on the replacement of the potentially labile ester linkage. These studies are significant in that the linker may have a profound influence on the conformational relationship between the central aromatic core and the pendant aromatic ring. In addition more hydrolytically stable analogs will be of great utility in in vivo studies. Three analogs with all carbon linkages between the core aromatic ring and the pendant aromatic ring (6, 7, 8) will be prepared. Sulfur-linked amalogs will also be prepared, which will include a sulfide, sulfoxide, and sulfone linker (9, 10, 11). An ether analog with an oxygen linkage between the core aromatic ring and the pendant aromatic rings (12) will be prepared. Amide-linked analog 13 and two bicycle-linked derivatives (14, 15) will be prepared. All of these analogs are based upon the WZB-117 structure. This core has been chosen based upon the activity of the parent compound and the ease of synthesis based on the WZB-117 core relative to the WZB-27 core.

Figure 14:
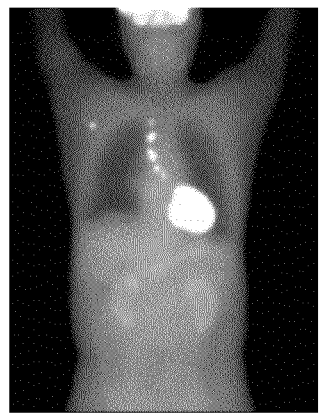
FIG. 14 shows a PET scan of primary and metastatic human cancer.
Figure 15:
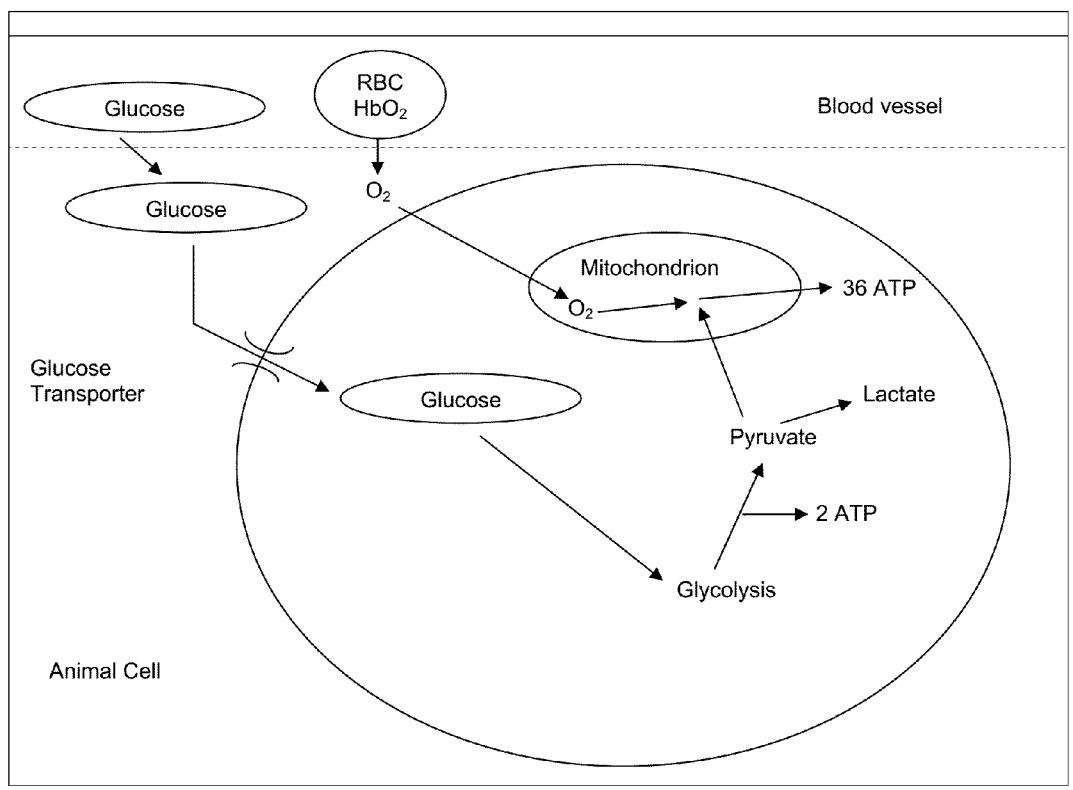
FIG. 15 shows insulin-like activities of α-PGG in 3T3-L1 adipocytes. A. The glucose transport stimulatory activity of α-PGG compared to that of insulin as measured by glucose uptake assays. B. α-PGG induces insulin-like GLUT4 membrane translocation as shown by fluorescence confocal microscopy using GLUT4 specific antibodies after cell induction by different agents. α-PGG induced an insulin-like GLUT4 translocation as in a ring structure surrounding the cells.

Contemplated herein are the energy-minimized structures of the proposed analogs are shown in FIG. 14. Several analogs stand out in their similarity to the parent WZB-117. These include alkene 7, sulfoxide 10, sulfone 11, and amide 13. All of these analogs have the pendant aromatic rings on opposite sides of the core aromatic ring. As might be expected alkane 8, sulfide 9, and ether 12 share strong similarities. The highly flexible nature of these analogs suggest that they can adopt a wide variety of conformers including that of the active WZB-117. Alkyne 6 and benzimidazole 14 are similar as they share a relatively planar overall structure. Dioxin 15 is unique, having a single well-defined conformation with both pendant aromatic rings on the same side of the core aromatic ring. Obviously, the alkyne and alkene derivatives with a very rigid linker provide unique structures unlike any of the others. The synthesis and assay of this set of analogs will provide information on optimal conformations and determine appropriate hydrolytically stable linkers.

The first set of analogs contemplated herein will contain a carbon linkage between the pendant hydroxyphenyl ring and the core fluoro phenyl ring and will be prepared using a single synthetic sequence. Starting from the known dibromo fluorobenzene 16, two Sonagashira couplings with terminal alkyne 17 will be achieved to provide an alkyne linked intermediate. Alkyne 17 can be prepared from the requisite aldehyde or via a Sonagashira coupling of the bromide. Deprotection of the hydroxyl group with acid should provide target analog 6. The alkyne will then be partially reduced to provide cis olefin analog 7. Finally, a complete hydrogenation of the olefin will be effected with $H_2$ and Pd to provide carbon-linked analog 8.

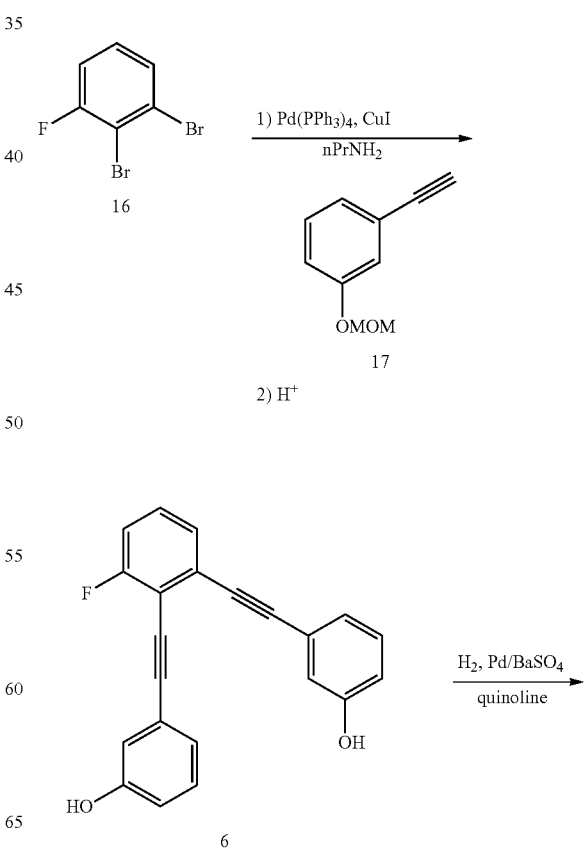

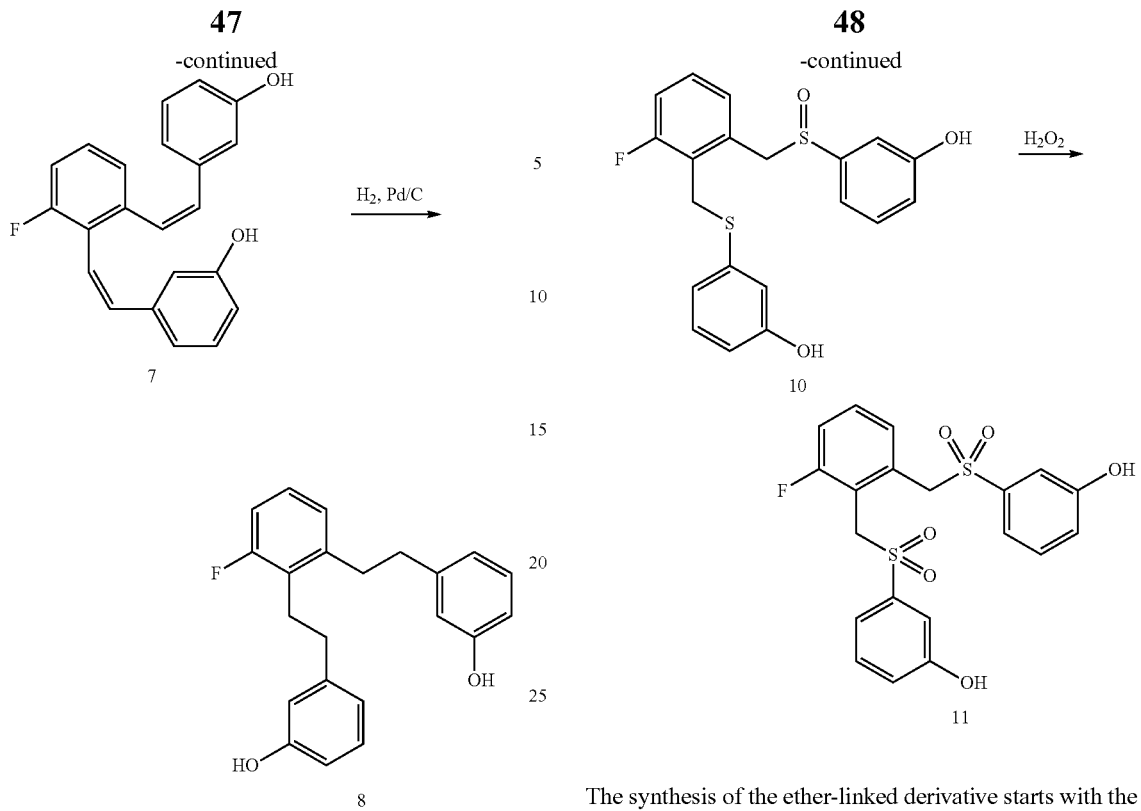

Also contemplated herein are a series of sulfur-linked analogs, including compounds 10 and 11, which will provide bioisosteric and hydrolytically stable analogs of the parent esters. Additionally, the three analogs (9-11) will alter the acidity of the phenol groups. The synthesis of this series starts with the dibromination of commercially available fluoride 18. The dibromide will then be used to alkylate thiophenol 19 to provide the first analog. Two sequential oxidations will then provide the sulfoxide (10) and the sulfone (11).

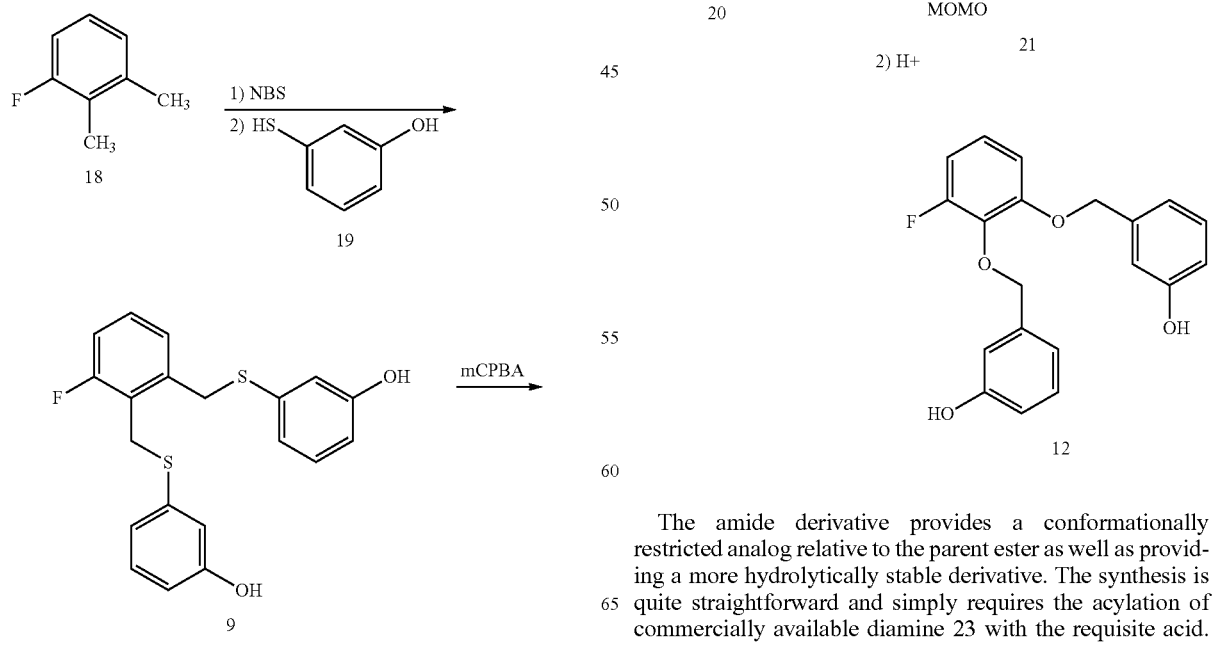

The synthesis of the ether-linked derivative starts with the dialkylation of diol 20 with benzyl bromide (21) to provide a protected bis ether. Bromide 21 can be readily prepared via the reduction/bromination of the corresponding acid. Deprotection of the phenolic hydroxyl groups with acid will then provide the target ether-linked analog 12.

The amide derivative provides a conformationally restricted analog relative to the parent ester as well as providing a more hydrolytically stable derivative. The synthesis is quite straightforward and simply requires the acylation of commercially available diamine 23 with the requisite acid. Removal of the MOM group will provide analog 13.

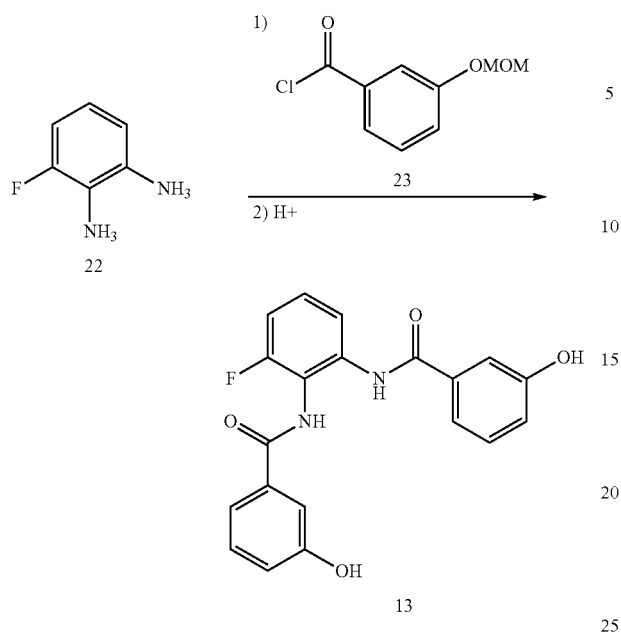

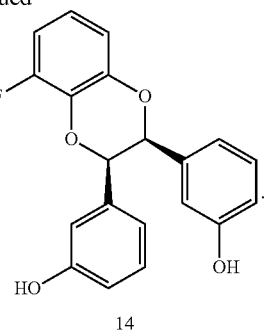

Benzimidazole analog 15 provides an alternate conformation relative to dioxin 14. In addition the benzimidazole ring should provide improved water solubility relative to the parent WZB-117. Compound WZB-117 has a ClogP of 2.96 (lower numbers indicating greater water solubility) while analog 15 has a ClogP of 2.72. Again, this compound should be hydrolytically stable. Diamine 22 will be condensed with aldehyde 28 to provide substituted benzimidazole 29. Acylation followed by removal of the benzyl protecting groups should provide the target compound 15.

Dioxin derivative 14 will provide a highly conformationally restricted analog. As shown below, this compound will be prepared via a condensation of α-bromoketone 27 and diol 20. Bromide 27 can be prepared via the coupling of Weinreb amide 24 with Grignard reagent 25. This will provide ketone 26, which can be readily brominated to provide key α-bromoketone 27. Condensation of 27 with diol 20 followed by stereoselective reduction of the intermediate oxonium ion provides the cis-disubstituted dioxin 14.

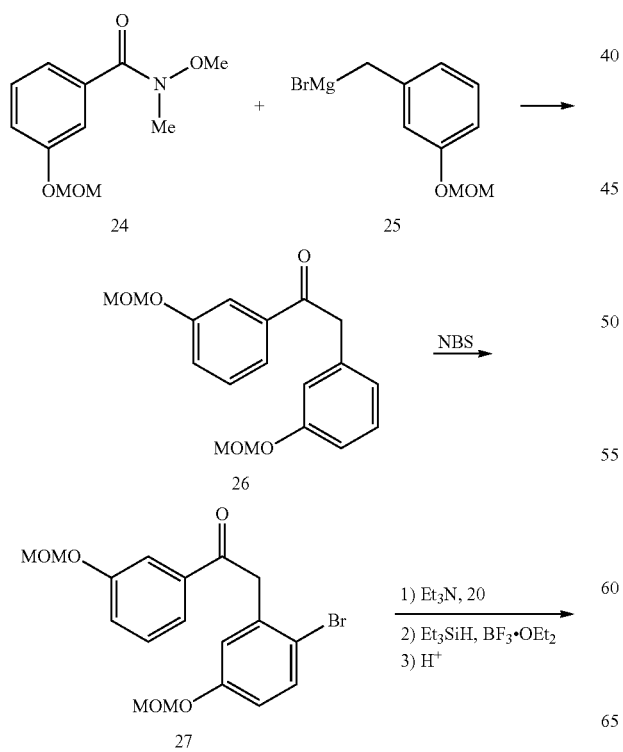

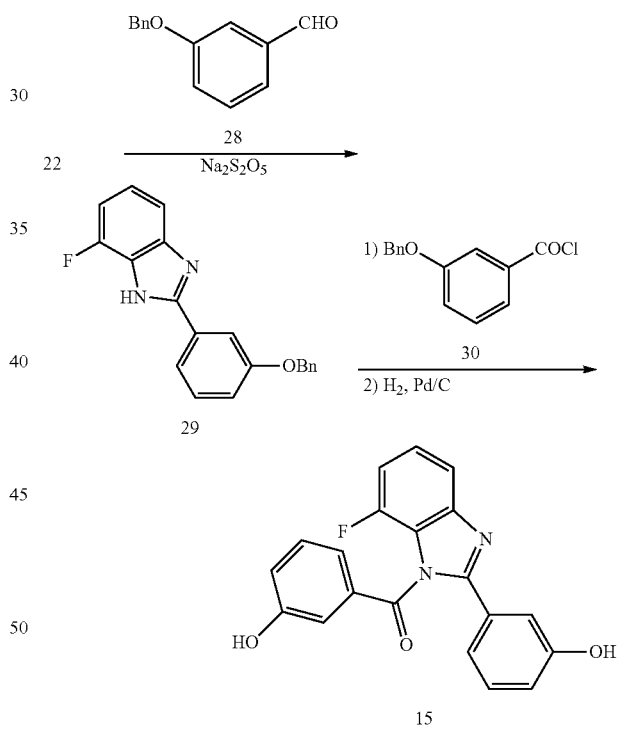

This set of compounds will provide an initial structure activity relationship for glucose uptake inhibition relative to the linker group. Several analogs have been proposed that address the stability of the ester group as well as the conformation of the pendant aromatic rings. These analogs represent only the initial targets for modification of the ester linkage and further modifications will be made to extend these studies as warranted by the pharmacological activity of this set.

Also contemplated herein are the following compounds, wherein R is selected from the group consisting of H, Me, Et, and iPr:

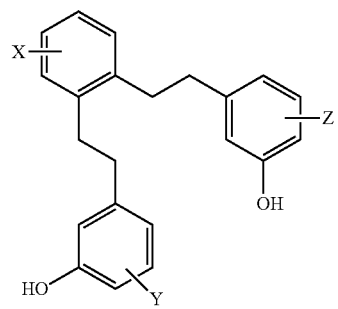

8

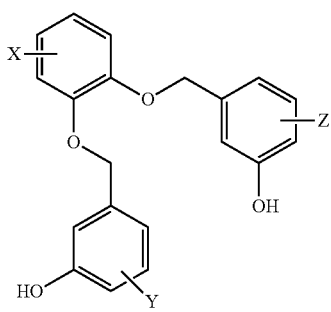

9, n = 0
10, n = 1
11, n = 2

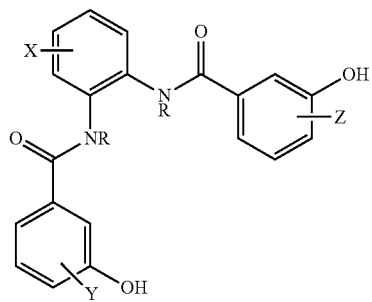

12

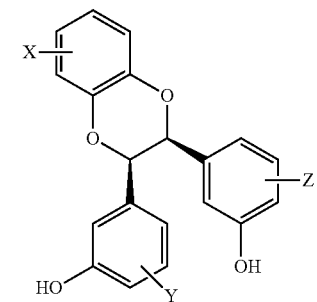

13

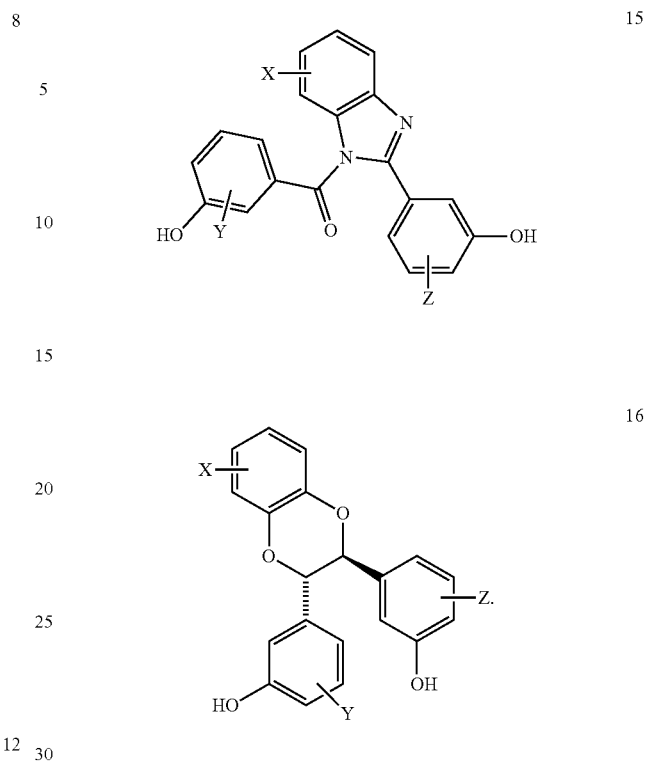

14

15

16

For all compounds X = H, 3-Cl, 3-F, 3-CN, 4-F
4-CN, 4-NO₂, 4-SO₂Me, 4,5-Cl₂

For all compounds Y or Z = H, 2-Cl, 2-F, 2-OMe, 2-CH₂OH
3-CH₂OH

Pendant Bioisosteric Replacements

The 3-hydroxyphenyl group has been identified as the optimal pendant aromatic group. Phenols are known to often have poor bioavailability and short duration of activity due the facile metabolism, conjugation and excretion of this group. Given the need to develop more metabolically stable analogs, a series of phenol bioisosteres will be examined. Dozens of such bioisosteres have been reported in the literature.

Contemplated herein are two general sets of analogs, the acetamido group and a series of heterocyclic bioisosteres. 3-Aminobenzoic acid will be converted to an acetamide, methansulfonamide, and a urea and then couple to diol 20 to provide analogs 31, 32, and 33, respectively. An additional analog (34), based on the replacement of a phenol with a hydroxymethyl group as seen in the β adrenergic blocker albuterol, will also be prepared. Four different heterocyclic derivatives (35-38) will be prepared by coupling the commercially available heterocyclic carboxylic acid with diol 20. This set of compounds will provide information on the ability to replace the phenolic group with potentially more metabolically stable moieties.

Also contemplated herein are the following compounds, wherein X is selected from the group consisting of H, 3-Cl, 3-F, 3-CN, 4-F, 4-CN, 4-NO₂, 4-SO₂Me, and 4,5-C₁₂:

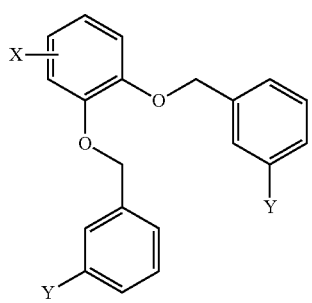

31, Y = NHC(O)CH₃
32, Y = NHS(O)₂CH₃
33, Y = NHCONH₂
34, Y = CH₂OH

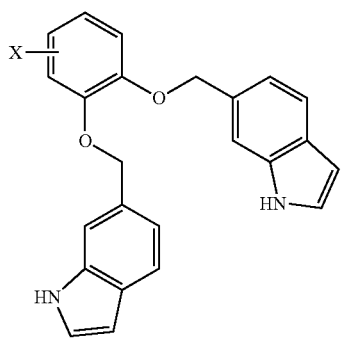

35

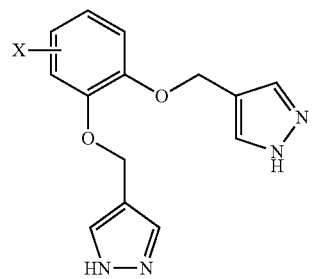

36

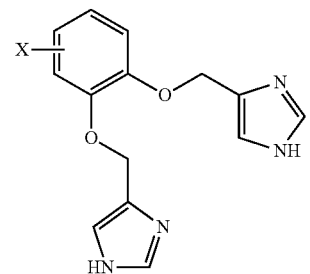

37

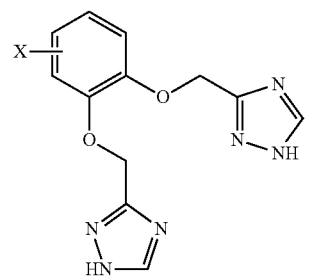

38

Optimization of the Central Aromatic Core

Figure 29:
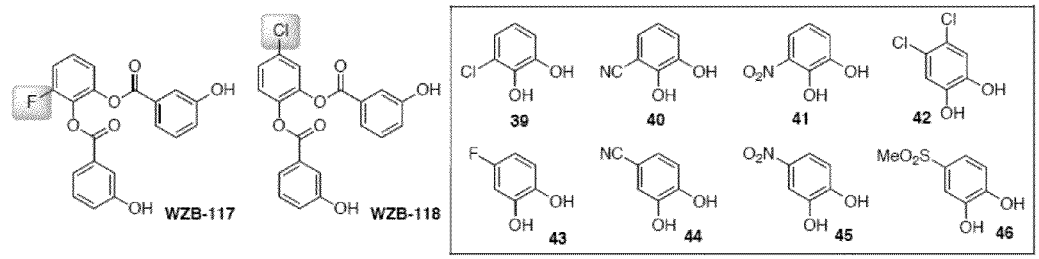
FIG. 29 shows an initial set of core aromatic rings.

Also contemplated herein is a third group of analogs, in which the central aromatic ring from WZB-117 and WZB-118 will be modified. This study will allow for the optimization of the activity of WZB-117 and WZB-118 analogs through changes in the substitution (i.e. the F or Cl group) on the aromatic ring. The introduction of a chloro- or fluoro- group to the aromatic core and the removal of one of the benzoyl groups has resulted in improved potency and a lower molecular weight. It has been demonstrated that the 3-fluoro and 4-chloro derivatives (when counting starting with the furthest O-benzoyl group) have the best activity. In terms of generating additional analogs, this means that the diols shown in FIG. 29 will be critical to further scaffold elaboration. A Topliss tree type approach has been employed to generate many of these derivatives. These derivatives will be acylated with acid chloride 23 and then deprotected as shown previously. These compounds are commercially available or may be easily prepared from a commercially available precursor by one who is skilled in the art. Compounds 39, 42, 46, and 43 are commercially available. Nitriles 40 and 44 can be prepared via an oxidative conversion of the corresponding aldehyde to the nitrile. Nitro derivatives 41 and 45 may be prepared by nitration with a zeolite supported copper nitrate reagent.

This set of compounds will provide valuable insight into optimal substitution on the central aromatic ring and provide directions for the synthesis of generation 4 and 5 analogs. This set of derivatives is a small sample of potential analogs that will be synthesized as a result of positive biological outcomes from generation 2 analogs, and further generations of analogs may be synthesized based upon the combination of, results from several specific modifications.

Experimental Protocols. Biological

Compounds.

Powders of compounds were stored at −20° C. and solutions were freshly prepared before each experiment. Compounds were dissolved in DMSO to make 10 mM stock solution. In most studies, 30 µM WZB-27 and 10 µM WZB-115 were used for cell treatment.

Cell Lines and Cell Culture.

Human non-small cell lung cancer (NSCLC) cell lines H1299 and A549, human duct epithelial breast cancer MCF7, and human non-tumorigenic NL20 lung and MCF12A breast cells were purchased from ATCC. H1299, A549 and MCF7 cells were maintained in Dulbecco's Modified Eagle Medium (DMEM) with 10% fetal bovine serum. NSCLC cell lines A549, H358, H226, and H1650 are grown in Ham's F12K containing 10% FBS. NL20 cells were maintained in a Ham's F12 medium, supplemented with 0.1 mM nonessential amino acids, 0.005 mg/ml insulin, 10 ng/ml epidermal growth factor, 0.001 mg/ml transferring, 500 ng/ml hydrocortisone, and 4% fatal bovine serum. MCF12A cells were cultured in a 1:1 mixture of DMEM and Ham's F12 medium, with 20 ng/ml human epidermal growth factor, 100 ng/ml cholera toxin, 0.01 mg/ml bovine insulin, 500 ng/ml hydrocortisone and 5% horse serum. All cells were grown at 37° C. in a humid atmosphere with 5% $CO_2$. Cells were treated with compound WZB-27 or WZB-115 at concentration of 30 µM or 10 µM, respectively, for 24 or 48 hours. Untreated cells were used as control.

Cell Lysate Preparation and Western Blot Analyses. Protocol 1.

Cells were harvested from plates, re-suspended with 3× sample buffer, and boiled for 5 min. Approximately 50 µg of protein extract was loaded after protein concentration measurement by Pierce bicinchoninic acid (BCA) protein assay (Pierce Biotechnology, Inc. Rockford, Ill.). Samples were run on a 10% Bio-Tris NuPAGE gel (Invitrogen) and transferred to a polyvinylidene difluoride membrane (PVDF, Biorad). The membrane was incubated with antibodies specific to p53, or PARP, or β-actin. Specific protein bands were visualized after the development of film. Antibodies for p53 were purchased from Santa Cruz Biotechnology, Inc. (Santa Cruz, Calif., USA). The PARP antibody and β-actin antibody were purchased from Cell Signaling Technology, Inc. (Danvers, Mass., USA).

Cell Lysate Preparation and Western Blot Analyses. Protocol 2.

Lysates from cells are prepared by NP40 lyses. Samples are boiled in equal volume of 2×SDS sample buffer, and separated on 8% polyacrylamide gels. After semi-dry transfer to supported nitrocellulose membranes, the blots are probed with monoclonal antibody to GLUT1 from R&D systems. The proteins are detected by using an enhanced chemiluminescence assay system from Amersham Biosciences.

Real Time RT-PCR Protocol.

Total RNA was isolated using Trizol® (Invitrogen, Carlsbad, Calif.). In order to eliminate any carryover of genomic DNA, total RNA was treated with DNAse using the DNA-free kit (Ambion, Austin, Tex.). cDNA was synthesized from total RNA using the Advantage RT for PCR (BD Biosciences, Palo Alto, Calif.). One mg of the total RNA was used in a 50 µl reaction mixture with the random hexamer primer. Real time primers and TaqMan® probes for GAPDH were purchased from Biosource (Camarillo, Calif.), and were used according to the manufacturer's instructions. Three ml of cDNA template were used in 25 µl of real time PCR reaction with ABI TaqMan® Universal Master Mix (Applied Biosystems, Branchburg, N.J.). The GLUT1 detection is done with Sybr® green dye and the Quntitect Sybr® Green kit according to the manufacturer's instructions, using 1 µl of cDNA template in a 25 µl reaction volume.

Glucose Uptake Assay.

Cancer cells are treated with or without the compounds for 10 min before the glucose uptake assay. Cellular glucose uptake will be measured by incubating cells in glucose-free RPMI 1640 with 0.2 Ci/mL [$^3$H]2-deoxyglucose (specific activity, 40 Ci/mmol) for 30 min in the absence and presence of compounds. After the cells are washed with ice-cold PBS and lysed, the cell lysates will be transferred to scintillation counting vials and the radioactivity in the cell lysates is quantified by liquid scintillation counting.

Cell Cycle Analysis.

After being treated by compounds or medium with low concentration of glucose, cells were harvested, washed with cold PBS, and re-suspended in 70% cold ethanol. After an overnight fixation, ethanol was removed and cells were treated with propidium iodide, DNase-free RNase A, and PBS mix (4:1:95) for 30 min at 37° C. The DNA content was analyzed by flow cytometry (FACS, BD). Modfit software (Verity Software House) was used to calculate the percentage of cells in each phase of the cell cycle. Each sample was repeated three times.

Cell Viability Assay.

MTT assays are performed by the following well-established method. In a 96 well tissue culture plate 10,000 cells are plated in each well. The cells are incubated in presence or absence of the compounds for 18 h. 3-(4,5-Dimethylthiazol-2-yl)-2,5-diphenyltetrazolium bromide (MTT) is dissolved in PBS (10 mg/ml) and filter sterilized. Three hours before the end of the incubation 20 µL of MTT solution is added to each well containing cells in a 96-well plate. The plate is incubated in an incubator at 37° C. for 3 h. Media is aspirated gently and 200 µL of DMSO is added to each well to dissolve formazan crystals. The absorbance is measured at 550 nm for cell viability.

Proliferation Assay.

MCF-7, H1299 and H1650 cells are plated onto poly-d-lysine (Sigma) coated 8-well glass chamber slides (10,000 cells per well). The cells are incubated with the compounds for 24 h or 48 hr. The cells are fixed and stained using 5-Bromo-2'-deoxyuridine labeling and Detection kit from Roche according to manufacturer's protocol.

Study for Anticancer Synergistic Effect.

H1299, and MCF7 cells were grown in 96-well plates. Cells were treated with either cisplatin or taxol at their $IC_{50}$s in presence or absence of compound WZB-27 (30 µM) or WZB-115 (10 µM) at 37° C. for 48 hours. Viability of the treated cells was measured by the MTT cell proliferation assay.

Apoptosis Assay.

MCF-7, H1299 cells are plated onto poly-d-lysine (Sigma) coated 8-well glass chamber slides (10,000 cells per well). The cells incubated with the compounds of various concentrations for 24 h. Cells without compound treatment serve as controls. After 24 h of incubation cells are fixed and stained according to manufacturer's instructions using Promega's DeadEnd Colorimetric TUNEL system. The cooperative effect of drugs will also be evaluated by adding 5 µM of cisplatin or paclitaxel or 10 µM gefitinib by the same procedure.

Immunofluorescence.

GLUT1 monoclonal antibody will be purchased from R&D Systems Inc (Minneapolis, Minn.). Cells are plated onto poly-d-lysine (Sigma) coated 8-well glass chamber slides (10,000 cells per well) for immunostaining. Cells are fixed in 3.5% paraformaldehyde for 25 min, permeabilized in 0.2% Triton X-100/PBS for 5 min, and blocked in 5% normal goat serum in PBS at room temperature for 1 h. Primary antibody incubation is performed overnight at 4° C. After washing, secondary antibody incubation is performed with goat anti-mouse IgG Alexa Fluor-488 for 30 min at room temperature. DAPI is detected using Vectashield Mounting Medium with DAPI (Vector Laboratories, Inc.). Staining by secondary antibodies only will be used as negative controls. Slides are observed by fluorescence microscopy using fluorescent microscope (40×/0.75 numerical aperture) with a camera.

Statistical Analyses.

Samples of same experimental conditions are in triplicate or more. Each experiment is repeated at least once (animal studies are exceptions). Data will be reported in mean±standard deviation or standard error of means. Data will be analyzed using unpaired Student t-test and with one-way or two-way ANOVA with Turkey's post-hoc test depending on the nature of the assays. Significance level was set at p≤0.05.

Experimental Protocols. Animal Studies

The ability of compounds to inhibit/reverse tumor growth in nude mice, as well as the clinical safety of the compounds will be determined. Only compounds that meet the following criteria will be considered for animal studies; $IC_{50}$ of <10 µM in the glucose uptake inhibition, and an $EC_{50}$ of <10 µM in cell killing assays as well as significant less killing in normal cells.

For the anticancer efficacy and safety animal study, each selected compound will be use to treat nude mice with cancer grown from H1299 (lung cancer) and MCF-7 (breast cancer) cells. Five millions of cancer cells will be injected subcutaneously into the flank of each of 15 nude mice. The tumor cell-injected mice will be randomly split into three groups: five for compound treatment, five for drug (e.g. WZB-117) treatment (positive controls) and another five receive vehicle (solvent) treatment. After tumors become palpable and visible (~2-3 weeks), the compound treatment will begin. A molar concentration of $EC_{50}$ will be chosen for each compound for the treatment. Compounds will be dissolved in DMSO or other compatible solvent.

The IP injection of compounds will be performed 3 times a week for 3-5 weeks depending upon tumor growth rates. Tumor sizes will be measured with calipers twice a week and recorded as W×L×H=volume in $mm^3$ and compared to those of tumors on non-compound injected control mice. Body weight of the mice is measured once a week. In order to determine how compound treatment affects blood glucose levels, blood glucose will also be measured immediately prior to the compound injection and 1 hr after the injection and the blood glucose levels will be compared to those of the non-compound injected mice. The compound treatment lasts 3-5 weeks until the tumors grown in the untreated mice become large (>5% but <10% of the body weight). The animal study will be carried out and terminated in accordance to the rules and regulations of NIH and of our university IACUC. Tumor-bearing mice will be euthanized at the end of the study, according to the related rules by NIH and DOA. The average size of the tumors in the treated groups will be compared to the untreated control group to show treatment efficacy and statistical differences.

The best compound(s), based on combined consideration of anticancer efficacy and toxicity (primarily its effect on blood glucose levels and body weight changes and/or other unexpected side effects), will be chosen for a larger scale animal study described below.

Investigation of the Molecular Mechanism of Action of Basal Glucose Transport Inhibitors Anticancer Activities in More Cancer Cell Lines Contemplated herein is a cancer cell line screen including multiple lung and breast cancer cell lines that will be tested with compounds to determine their anticancer activities via the MTT assay to demonstrate that the compounds' cancer cell killing activity is an activity that is cell line-independent. H1299 cells are derived from non-small cell lung cancers (NSCLC). Other NSCLC cell lines such as A549, H358, H226, and H1650 will also be tested. Similarly, the compounds will also be tested in breast carcinoma cell line T47D along with MCF-7 to determine if the compounds exhibit similar anti-cancer activity in the additional breast cancer cell lines. Normal cells of same tissues (NL20 for normal lung tissue and MCF-12A for normal breast tissue) will be included in the study to establish compounds' increased cytotoxicity and killing to cancer cells than to their normal counterparts. To correlate inhibition of basal glucose transport with cytotoxicity of the compounds, glucose uptake rates of cancer and normal cell lines will be measured and compared using the glucose uptake assay. The cancer cell lines are expected to exhibit higher glucose uptake rates than their normal cell counterparts due to their higher energy needs. Increased cell killing in cancer cells opposed to normal cells may be due to the inhibition of basal glucose transport that is crucial for cancer cell proliferation and survival. This study will also further strengthen the notion that the basal glucose transport is the target of the anticancer action of the compounds disclosed in this patent and related publications. The enzymatic activity of hexokinase, the first enzyme involved in glycolysis, will also be measured with standard assays in the compound treated cells using untreated cells as a control to determine how glycolysis is affected by the compound treatment in these cancer cells.

In addition to the cell lines described, select compounds will be submitted to the Developmental Therapeutics Program's NCI 60-Cell Line Screen.

Also contemplated herein is the theory that the basal glucose tansporters disclosed will potentiate the chemotherapeutic effects of other anti-cancer agents. In order to determine if the compounds can potentiate anti-cancer activity of other anticancer drugs, 5 µM of cisplatin or paclitaxel or 10 µM gefitinib will be added to H1299 and MCF-7 cells in the absence and presence of the compound for 48 hrs. After incubation, cell viability will be determined by both MTT and the cell proliferation assays (see general procedures at the end of this section for details). (Drug+compound) treated samples will be compared to those samples treated by drugs alone. Increased cell death in the (drug+compound) treated samples indicates that the compound could potentiate the anticancer activity of the drugs.

Additional Receptor Binding Assays

Contemplated herein are a series of receptor binding assays which will be used to determine the action target of the basal glucose transport inhibitor disclosed in this application. In order to investigate the action target of the compound, a binding competition study will be carried out. Anti-GLUT1 antibodies will be added to H1299 or MCF-7 cells in the absence and presence of increasing amount of the compound at 37° C. for 1 hr. After co-incubation, unbound antibodies and compound will be removed by washing. The treated cells will be incubated with a secondary antibody (goat anti-mouse IgG Alexa Fluor-488) that interacts with the bound anti-GLUT1 antibodies. A "chromogenic" reaction will be performed after the secondary antibody binding. The intensity of fluorescence generated by the bound secondary antibodies should be proportional to the GLUT1-bound primary antibodies. The intensity of the fluorescence of differently treated cells will be quantified and compared. The decrease of the intensity in the antibody/compound treated samples suggests that the presence of the compound decreases the binding of GLUT1 antibodies to GLUT1 and further strongly suggests that the compound bind to GLUT1 located on the cell membrane. On the other hand, if no competition is found, it does not necessarily mean that the compound does not bind to GLUT1. It may also mean that the compound binds to a place on GLUT1 that is different from the binding site of anti-GLUT1 antibody.

To further determine how compounds work, the anti-GLUT1 antibody of a fixed concentration will be added to cancer cells in a glucose uptake assay in the absence and presence of the compounds of various concentrations. In a similar study, the compound concentration can be fixed and the antibody's concentration can be varied. These glucose uptake assays are to determine whether the basal glucose transport inhibitory activities of anti-GLUT1 antibody and the compounds are additive or synergistic to each other. If the activities are additive to each other, it may suggest that these two agents act, probably but not necessarily, on the same target. If the activities are synergistic, it is more likely that these two molecules act on different targets. It is also possible that the effects may not change or even decrease when compounds are added with GLUT1 Ab.

Cotemplated herein is a method to directly show the binding of the compound to GLUT1, which will be accomplished by the inclusion of a fluorescent tag as a moiety on any lead compounds. It is anticipated that more potent and selective analogs will be identified prior to the preparation of fluorescent tracers. Two approaches will be used to identify the necessary fluorescent probes. As an illustrative example we will show a synthesis based on the current lead compounds. In the first approach we will replace a pendant aromatic ring with a fluorescent tag. Depending upon the SAR for these compounds this could be the optimal approach in that we can use fluorescent tags similar to the pendant aromatic rings. Thus a significant change in affinity to the biological target would be decreased. As shown below, we would monoprotect triol 1, and then introduce two esters onto the free hydroxyl groups. The protected hydroxyl would be deprotected to provide 48. The fluorescent coumarin 49 would be coupled to provide the target fluorescent probe 50.

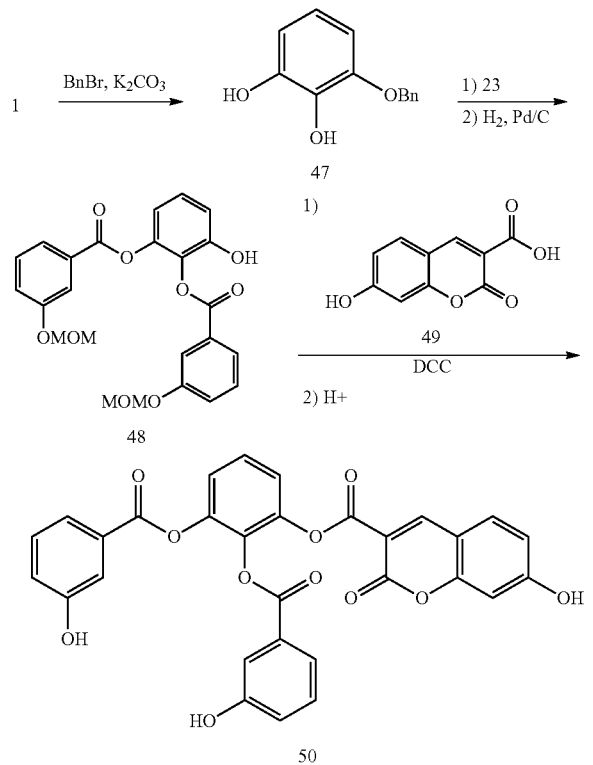

A second approach will be to simply label an active compound with a fluorescent tag. For example we would couple WZB-113 with any of a number of commercially available fluorescent carboxylic acids (flRCOOH=49 or rhodamine, or carboxynaphthofluorescein). Based on the activity of WZB-113 relative to WZB-117 only one of the two hydroxyl groups is likely involved in significant non-covalent interactions. Thus we can use one of these hydroxyl groups to attach the fluorescent tag.

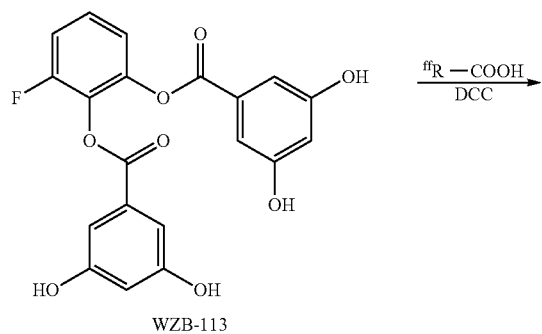

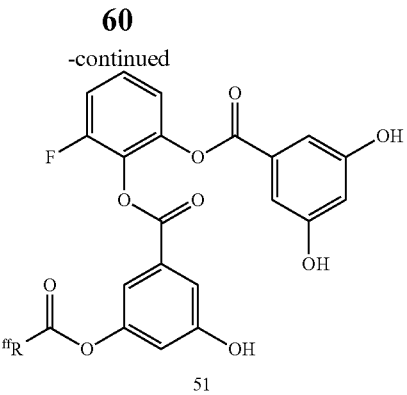

All fluorescently tagged compounds will first be evaluated for their ability to both inhibit basal glucose transport and induce apoptosis. If the fluorescent analogs do not act in a similar manner to the parent compound new derivatives will be prepared.

Varying concentrations of the fluorescent compound, will be used to incubate with GLUT1 pre-bound to the bottom of a 96-well plate with a protocol similar to that previously used for insulin receptor binding of the polyphenolic compound PGG. After an overnight incubation at 4° C. with shaking, the unbound compound will be washed off. The fluorescence intensity of different samples will be measured with a 96-well plate reader (SPECTRA Max M2, software: SoftMax Pro). A GLUT1 binding saturation curve can be generated from intensities corresponding to different compound concentration. The GLUT1 binding affinity ($K_a$) can also be generated from this binding experiment. A binding displacement curve can also be generated from an assay in which an increasing amount of regular compound is added to GLUT1 pre-bound to 96 well plates while fluorescent compound is kept at a fixed concentration. At higher concentrations, the regular compound will compete with fluorescent compound for the same binding site on GLUT1, reducing the fluorescent intensity proportionally to the increased concentrations of the regular compound. The binding affinity of the compound ($K_d$) can be derived from the displacement curve using computer software.

Relationships and Signaling Pathways Linking Inhibition of Basal Glucose Transport and Induction of Apoptosis in Cancer Cell Lines Although it has been shown that addition of compounds leads to inhibition of basal glucose transport inhibition and apoptosis (cancer cells), the cause-effect relationship between the inhibition and apoptosis has not been established. To determine the relationship, cell samples treated with anti-GLUT1 antibody will be used as a positive control. Since the anti-GLUT1 antibody has only one target, GLUT1, the apoptosis induced by the addition of the antibody is the "direct effect" caused by the antibody. In this study, the apoptosis induced by the compounds will be compared side by side with the apoptosis induced by the antibody. The parameters compared include: 1) onset time of the apoptosis induced; 2) dose responses of apoptosis; 3) apoptosis inducing mechanism. It has been disclosed that the apoptosis induced by compounds WZB-25 and WZB-27 is p53-independent (FIG. 24A). If the apoptosis induced by the antibody is also p53-independent (p53 is not significantly changed by the antibody treatment), then this evidence would support the fact that these compounds induce apoptosis in cancer cells using a mechanism similar to that of the antibody. If the apoptosis induced by the antibody is p53-dependent (p53 is activated), it indicates that the antibody uses a mechanism in apoptosis induction different than the one used by the compounds. This will strongly suggest that compounds inhibit a different target than GLUT1.

Also contemplated herein is a proteomic approach to study the link between inhibition of basal glucose transport and induction of apoptosis. The selected compound will be used to treat H1299 and MCF-7 cells for 24 hrs with untreated cells as negative controls. Total proteins will be isolated from the treated and the untreated cells. Protein samples will be treated with protease inhibitor, TBP and sample buffer which contains urea, thiourea, and CPHAS for 2 hours. Then IAA will be added. Twenty min later, IAA will be added to the samples again. After treatment, samples will be loaded to strips and the strips with samples will be kept in room temperature for 2 hours before they are placed in the first dimension gel electrophoresis instrument for the first dimensional protein separation. After finishing the first dimensional protein separation, the strip will be loaded on SDS-PAGE gels for the secondary protein separation. After the separation, gels will be fixed overnight with fixing buffer containing ethanol, acetic acid, and SDS. Then the gels will be washed with washing buffer containing acetic acid and SDS before they are stained with sypro orange for 2 hours for spot detection. The 2-D gel results will be analyzed with software of PDQuest.

Protein spots will picked automatically under control of a camera and transferred to a 96-well microtiter plate with holes in the bottom. The microtiter plate with all gel spots will be transferred to an automatic digester (Tecan GmbH) to wash the gel pieces, digest the protein with trypsin at 50° C. for 2 hrs. The digest will be done with 2 mM ammoniumhydrogen carbonate buffer (pH 7.8) to reduce the salt content and the and 0.5 µL of the extracted peptides are automatically spotted on a MALDI target, whereas the remaining 20 µL are stored in a microtiter plate. Usually about 90% of all protein spots can be already identified from the MALDI-TOF/TOF mass spectra by combining a peptide mass fingerprint with the tandem mass spectra of the top five peptide signals. Alternatively, the sample stored in the microtiter plate can be analyzed my nanoRP-HPLC-nano-ESIQqTOF-MS/MS, which usually gives a better sequence coverage and often a better confidence level. Overall proteins can be identified at the 100 fmol level.

Twenty up-regulated protein spots and twenty down-regulated spots on a single gel, as compared to the untreated control gel, will be selected for MS analysis and amino acid sequence determination. Considering the intrinsic variations of the system, only those spots that are either up-regulated by 2-fold or more or down-regulated by 2-fold or more will be chosen. After the amino acid sequence of the N-terminus of a protein is determined, the identity of the protein will be uncovered by comparing the sequence with the protein sequences in the data bank. By knowing which proteins are up-regulated or down-regulated by the compound treatment, these proteins will be categorized into different groups and different metabolic and/or signaling pathways, which should enable us to identify pathways that are activated or inactivated by the compound, providing clues for how the inhibition of basal glucose transport leads to eventual induction of cancer cell apoptosis.

In Vivo Anticancer Studies

Although the compounds' anticancer activity in cancer cell lines has been established in preliminary studies and in a recent GLUT1 antibody study in multiple cancer cell lines, it has also been tested in animal models, which is an intermediate step for moving cancer research from laboratory to clinics. Secondly, inhibiting basal glucose transport may induce hyperglycemia in the treated animals. To address the question of in vivo efficacy and safety, a compound selected based on its improved $IC_{50}$ (basal glucose transport), $EC_{50}$ (cancer cell killing), and maintained/improved target selectivity (improved killing in cancer cells without increased killing in normal cells), as well as anticancer efficacy and safety findings from animal study described above will be used in this animal study.

The objectives of the proposed animal study are to determine if the compound treatment reduces cancer growth and if the compound treatment is safe to the tumor-bearing mice. The effective and safe doses will be chosen based on cell killing assays on cancer cell lines and tolerable cytotoxicity in the normal counterparts of the cancer cells tested as well as in a short term pilot animal study similar to the one described above, in which the cell study-determined compound dose and 2× and 4× doses will be tested in nude mice (3 per group). In the pilot study, the compound will be administered to mice once a day for five days and the compound-injected mice will be monitored for signs of side effects (hyperglycemia immediately after compound treatment and with time, reduction and difficulty in movement, loss of body weight). A safe dose will be selected and an animal study will be performed as follows:

Because human cancer cell line(s) will be used, immune-deficient nude mice will be used. A total of 30 nude mice will be used, 10 mice per group. These mice will be randomly selected into each group. Group 1 is the negative control group, which will be inoculated with cancer cells but without receiving subsequent compound treatment; Group 2 will be the low dose compound treatment group and group 3 will be high dose compound treatment group. Five million cells of either H1299 or MCF-7 cell lines will be injected subcutaneously (SubQ) into the flank of nude mice. We decided to use H1299 NSCLC and MCF-7 cells as our cancer models were based on these considerations: (a) although the inhibitors showed anticancer activity in all the cancer cell lines we tested, they showed either the higher anticancer activity or higher cancer cell: normal cell killing ratios or both among all cell lines tested, (b) NSCLC and breast cancers are two cancers that have been considered major targets of current cancer research and therapeutic treatment. In addition, GLUT1 has been found over-expressed in these two cancer types.

The compound treatment will start when tumors become palpable and visible. The compound at a concentration of 10 mg/kg of body weight will be intraperitoneally (IP) injected, one injection for every other day (except the weekends) for the entire study. The negative control mice will be injected exactly the same way but with vehicle (the solution in which the compound is dissolved). Tumor size will be measured twice a week with calipers, and dimensions of length, width and height of the tumors will be measured and recorded (L×W×H) as tumor volumes. The compound treatment lasts 3-5 weeks until the tumors grown in the untreated mice become large (>5% but <10% of the body weight). The animal study will be carried out and terminated in accordance to the rules and regulation of NIH and our university IACUC. Tumor-bearing mice will be euthanized at the end of the study according to the related rules by NIH and DOA. The average size of the tumors in the treated groups will be compared to the untreated control group to show treatment efficacy and statistical differences. The tumor size will also be compared between the high dose group and the low dose group to show the dose response of the treatment. The food intake, body weight, as well as blood glucose levels will also be measured twice a week to monitor the animal health and to compare these health parameters with the untreated control group. At the end of the animal study, after animal euthanasia, tumors will be removed from the compound treated mice and from the untreated control mice. Total proteins will be isolated from the tumors and their respective p53 and caspase 3 will be measured to determine if more apoptosis is induced in the compound treated mice and if there is any change in the activated p53. This is to determine if the in vivo anticancer mechanism is the same as observed in cancer cell lines.

Animal Tumor Treatment Study. Protocol

1. Study from November 2009 to January 2010, 10 weeks; 2. Nude mice (immunodeficient), ten mice per group; 3. Tumor model—Human lung cancer A549 (NIH recognized and recommended), 5×10⁶ cells injected into the flank of each mouse subcutaneously; 4. Treatment with or without compound WZB-117, PI injection daily for all 10 weeks, dose=15 mg/kg body weight; 5. Weekly measurements: tumor size, body weight, food intake; and 6. Other indicators measured: blood glucose, serum insulin, body composition, and blood cell counts. FIGS. 30-34 and Tables 8-11 show the results of this study.

TABLE 8

Body mass composition

| Treatment | Body weight (g) | Fat g | Fat % | Fluid g | Fluid % | Lean g | Lean % |
|---|---|---|---|---|---|---|---|
| Control | 29.30 ± 1.55 | 2.84 ± 0.61 | 9.74 ± 2.29 | 1.78 ± 0.38 | 6.02 ± 1.07 | 23.61 ± 1.64 | 80.54 ± 2.22 |
| WZB117 | 28.48 ± 0.17 | 1.05 ± 0.17* | 3.69 ± 0.61* | 1.80 ± 0.12 | 6.32 ± 0.40 | 24.40 ± 0.72 | 85.69 ± 2.40 |

Minispec data indicated that the difference in body weight between the control and WZB-117 treated group was primarily due to decrease in fat tissue in the WZB-1,7-treated mice. Body mass composition of each mouse was measured by the Minispec NMR Analyzer mq7.5 (Bruker, Billerica, Mass.) after 70 days of compound WZB-117 treatment. Results were analyzed by an OPUS program (Bruker).

TABLE 9

Blood cell count analysis of differently treated mice

| CBC parameters | No tumor no treatment group | PBS + DMSO treatment group | WZB 117 treatment group | Normal range |
|---|---|---|---|---|
| WBC (K/µl) | 10.1 ± 3.3 | 9.1 ± 1.6 | 5.9 ± 0.3 | 1.8-10.7 |
| LYMPH (K/µl) | 7.2 ± 2.2 | 4.9 ± 1.6 | 2.0 ± 0.7 | 0.9-9.3 |
| RBC (M/µl) | 10.0 ± 0.3 | 8.7 ± 1.7 | 8.8 ± 2.0 | 6.36-9.42 |
| HGB (g/dL) | 15.9 ± 0.5 | 13.7 ± 2.0 | 13.8 ± 2.6 | 11.0-15.1 |
| PLT (K/µl) | 1522.5 ± 159.7 | 1427.9 ± 327.0 | 2214.0 ± 192.3 | 592-2972 |

Blood was collected after 70 days treatment through mouse tail vein using heparinized capillary tubes and then transferred to EDTA containing microfuge tubes. Blood was analyzed using Hemavet 950 hematology system from Drew Scientific (Dallas, Tex.). CBC analyses indicated that, compared to the PBS-DMSO-treated group, WZB-117 treated group showed reduced counts in WBC, lymphocyte, as well as increased platelet count. However, these changes for the treated group were still in the normal ranges.

TABLE 10

Serum insulin levels in differently treated mice.

| Treatment | Serum insulin (mg/l) |
|---|---|
| No tumor no treatment | 0.971 ± 0.373 |
| PBS + DMSO | 0.743 ± 0.104 |
| WZB117 | 0.572 ± 0.319 |
| Normal range | 0.5-10 |

Serum from each mouse was obtained by centrifuging the blood from mouse tail vein at 10,000 rpm for 10 minutes and keeping the supernatant. Serum insulin level of each mouse was measured using Mercodia Ultrasensitive Mouse Insulin ELISA (Uppsala, Sweden). Compared to the PBS-DMSO-treated group, WZB-117 treated group showed reduced circulating insulin in serum. However, the change was still in the normal range. Considering that there was no significant difference in blood glucose levels between untreated and compound WZB-117 injection group, the reduced but normal serum insulin level indicated the normal function of pancreas after 70 days treatment of compound WZB-117.

TABLE 11

HPLC analysis of compound stability in human serum

| | Compound concentration (%) Time after incubation with serum | | | | | | | |
|---|---|---|---|---|---|---|---|---|
| Compound | 0 h | 1 h | 2 h | 4 h | 8 h | 16 h | 24 h | 48 h |
| WZB-115 | 100 | 41.6 | 18.9 | 18.4 | 0.6 | — | 0 | 0 |
| WZB-117 | 100 | 25.1 | 15.2 | 10.1 | 7.7 | 7.8 | 5.4 | 5.0 |
| WZB-141 | 100 | 100.3 | — | 103.5 | — | — | 109.7 | 87.4 |
| WZB-149 | 100 | 86.4 | 50.7 | 43.9 | 50.9 | 65.0 | 51.0 | 62.4 |

A total of 2.5 ml of compound solution was added to 22.5 ml of human serum and the mixture was incubated at 37 C for various times. The final concentration of the compound in serum was 6.8 mM. After incubation, 200 ml of acetonitrile was added to the mixture, centrifuged to remove proteins before HPLC analysis. The relative concentration of samples at 0 h (in serum but without incubation) was arbitrarily assigned a value of 100% and all other samples were compared to the 0 h samples. Analysis indicated that ether bond-containing compounds WZB-141 and WZB-149 were much more stable in serum than ester bond-containing compounds WZB-115 and WZB-117.

The invention claimed is:

1. A basal glucose transport inhibitor compound of formula (III) or a salt thereof:

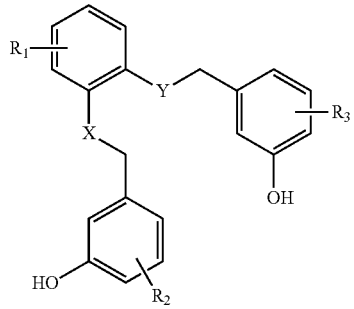

(III)

wherein R₁ is selected from the group consisting of halo, alkyl, benzyl, amino, nitro, cyano, and alkoxy;

wherein R₂ is selected from the group consisting of hydrogen, halo, alkyl, benzyl, amino, nitro, cyano, and alkoxy;

wherein R₃ is selected from the group consisting of hydrogen, halo, alkyl, benzyl, amino, nitro, cyano, and alkoxy;

wherein X is selected from the group consisting of —CH₂—, —NH—, —NCH₃—, and —O—;

wherein Y is selected from the group consisting of —CH₂—, —NH—, —NCH₃—, and —O—; and wherein said basal glucose transport inhibitor compound of formula (III) or a salt thereof inhibits basal glucose transport when administered to a subject.

2. The basal glucose transport inhibitor compound according to claim 1, wherein the basal glucose transport inhibitor compound is selected from any one of:

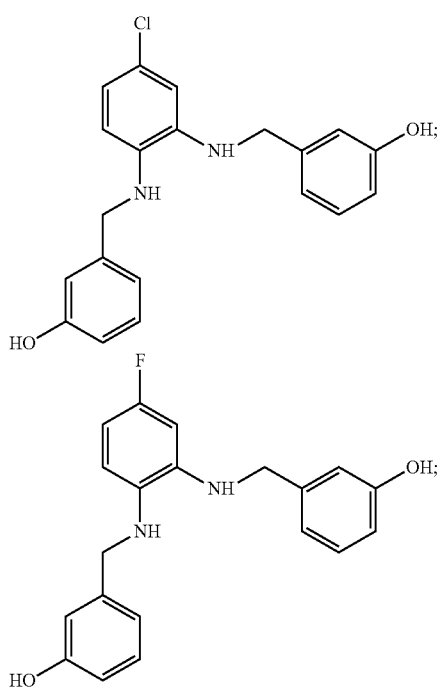

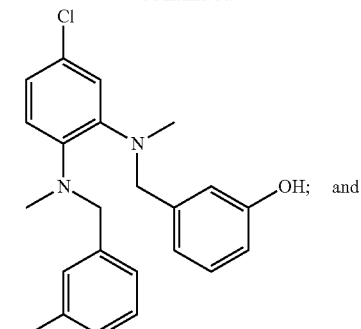

and

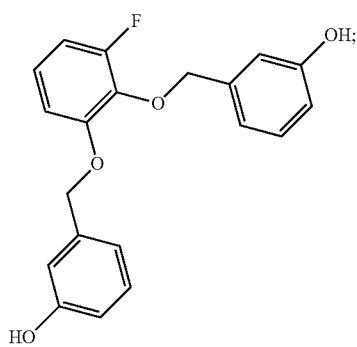

or a salt thereof.

3. The basal glucose transport inhibitor compound of formula (III) or a salt thereof according to claim 1, wherein R₁ is halo;

wherein R₂ is selected from hydrogen and alkyl;

wherein R₃ is selected from hydrogen and alkyl;

wherein X is —NH—; and wherein Y is —NH—.

4. A method of treating cancer comprising:

administering to a subject in need of such treatment a therapeutically effective amount of a basal glucose transport inhibitor compound of formula (III) or a pharmaceutically acceptable salt thereof:

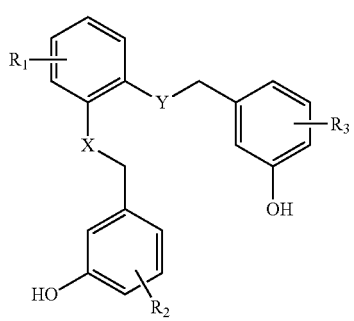

(III)

wherein R₁ is selected from the group consisting of halo, alkyl, benzyl, amino, nitro, cyano, and alkoxy;

wherein R₂ is selected from the group consisting of hydrogen, halo, alkyl, benzyl, amino, nitro, cyano, and alkoxy;

wherein R₃ is selected from the group consisting of hydrogen, halo, alkyl, benzyl, amino, nitro, cyano, and alkoxy;
wherein X is selected from the group consisting of —CH₂—, —NH—, —NCH₃—, and —O—;
wherein Y is selected from the group consisting of —CH₂—, —NH—, —NCH₃—, and —O—; and
whereby administration of said basal glucose transport inhibitor compound of formula (III) or a pharmaceutically acceptable salt thereof to the subject treats said cancer by inhibiting basal glucose transport in said subject, and wherein the cancer is selected from lung cancer, colon cancer, melanoma, leukemia, ovarian cancer, renal cancer, prostate cancer, breast cancer, or a glioma.

5. The method of claim 4, wherein the cancer upregulates basal glucose transport.

6. The method of claim 4, wherein the basal glucose transport inhibitor compound of formula (III) or pharmaceutically acceptable salt thereof is administered via at least one of the following methods: oral, topical, intraarterial, intrapleural, intrathecal, intraventricular, subcutaneous, intraperitoneal, intraveneous, intravesicular, and gliadel wafers.

7. The method of claim 4, wherein the subject is a human.

8. The method of claim 4, further comprising administering to the subject in need of such treatment a second cancer drug.

9. The method of claim 8, wherein the second cancer drug is selected from the group consisting of methotrexate, doxorubicin hydrochloride, fluorouracil, everolimus, imiquimod, aldesleukin, alemtuzumab, pemetrexed disodium, palonosetron hydrochloride, chlorambucil, aminolevulinic acid, anastrozole, aprepitant, exemestane, nelarabine, arsenic trioxide, ofatumumab, bevacizumab, azacitidine, bendamustine hydrochloride, bexarotene, bleomycin, bortezomib, cabazitaxel, irinotecan hydrochloride, capecitabine, carboplatin, daunorubicin hydrochloride, cetuximab, cisplatin, cyclophosphamide, clofarabine, ifosfamide, cytarabine, dacarbazine, decitabine, dasatinib, degarelix, denileukin difitox, denosumab, dexrazoxane hydrochloride, docetaxel, rasburicase, epirubicin hydrochloride, oxaliplatin, eltrombopaq olamine, eribulin mesylate, erlotinib hydrochloride, etoposide phosphate, raloxifene hydrochloride, toremifane, fulvestrant, letrozole, filgrastim, fludarabim phosphate, pralatrexate, gefitinib, gemcitabine hydrochloride, gemcitibinecisplatin, gemtuzumab ozogamicin, imatinib mesylate, trastuzumab, topotecan hydrochloride, ibritumomab tiuxetan, romadepsin, ixabepilone, palifermin, lapatinib ditosylate, lenalidomide, leucovorin calcium, leuprolide acetate, liposomal procarbazine hydrochloride, temozolomide, plerixafor, acetidine, sorafenib tosylate, nilotinib, tamoxifen citrate, romiplostim, paclitaxel, pazopanib hydrochloride, pegaspargase, prednisone, procarbazine hydrochloride, proleukin, rituximab, romidepsin, Talc, sorafenic tosylate, sunitinib malate, thalidomide, temsirolimus, toremifene, trastuzumub, pantiumumab, vinblastine sulfate, vincristine, vorinostat, zoledronic acid, and any combination thereof.

10. The method of claim 4, wherein the basal glucose transport inhibitor compound is selected from any one of:

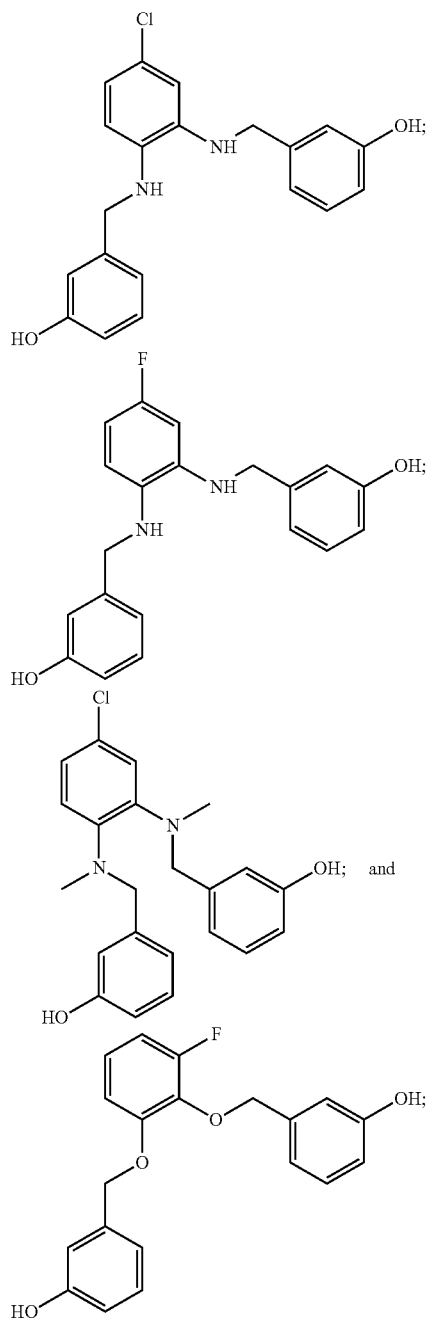

or a pharmaceutically acceptable salt thereof.

11. The method of claim 4,
wherein R₁ is halo;
wherein R₂ is selected from hydrogen and alkyl;
wherein R₃ is selected from hydrogen and alkyl;
wherein X is —NH—; and
wherein Y is —NH—.

* * * * *